(12) United States Patent
Bourke, Jr. et al.

(10) Patent No.: US 11,534,622 B2
(45) Date of Patent: Dec. 27, 2022

(54) NON-INVASIVE SYSTEMS AND METHODS FOR SELECTIVE ACTIVATION OF PHOTOREACTIVE RESPONSES

(71) Applicant: IMMUNOLIGHT, LLC, Detroit, MI (US)

(72) Inventors: Frederic A. Bourke, Jr., Aspen, CO (US); Zakaryae Fathi, Raleigh, NC (US); Harold Walder, Belville, NC (US)

(73) Assignee: IMMUNOLIGHT, LLC, Detroit, MI (US)

( * ) Notice: Subject to any disclaimer, the term of this patent is extended or adjusted under 35 U.S.C. 154(b) by 349 days.

(21) Appl. No.: 15/504,917

(22) PCT Filed: Aug. 17, 2015

(86) PCT No.: PCT/US2015/045500
§ 371 (c)(1),
(2) Date: Feb. 17, 2017

(87) PCT Pub. No.: WO2016/028680
PCT Pub. Date: Feb. 25, 2016

(65) Prior Publication Data
US 2017/0239489 A1  Aug. 24, 2017

Related U.S. Application Data

(60) Provisional application No. 62/038,674, filed on Aug. 18, 2014.

(51) Int. Cl.
*A61N 5/06* (2006.01)
*A61B 18/00* (2006.01)
(Continued)

(52) U.S. Cl.
CPC .............. *A61N 5/062* (2013.01); *A61N 1/40* (2013.01); *A61N 5/02* (2013.01); *A61N 5/0601* (2013.01);
(Continued)

(58) Field of Classification Search
CPC ........ A61N 5/062; A61N 5/02; A61N 5/0601; A61N 5/0616; A61N 5/0618;
(Continued)

(56) References Cited

U.S. PATENT DOCUMENTS 4,705,952 A * 11/1987 Lindmayer ........ C09K 11/7786
250/483.1
5,216,176 A * 6/1993 Heindel ............... C07D 493/04
549/287

(Continued)

FOREIGN PATENT DOCUMENTS

WO    WO 2012/019081 A2    2/2012

OTHER PUBLICATIONS

International Search Report dated Jan. 27, 2016, in PCT/US2015/045500 filed Aug. 17, 2015.
(Continued)

*Primary Examiner* — Nathan R Price
*Assistant Examiner* — Mark A Igel
(74) *Attorney, Agent, or Firm* — Oblon, McClelland, Maier & Neustadt, L.L.P.

(57) ABSTRACT

Products, compositions, systems, and methods for modifying a target structure which mediates or is associated with a biological activity, including treatment of conditions, disorders, or diseases mediated by or associated with a target structure, such as a virus, cell, subcellular structure or extracellular structure. The methods may be performed in situ in a non-invasive manner by application of an initiation energy to a subject thus producing an effect on or change to
(Continued)

the target structure directly or via a modulation agent. The methods may further be performed by application of an initiation energy to a subject in situ to activate a pharmaceutical agent directly or via an energy modulation agent, optionally in the presence of one or more plasmonics active agents, thus producing an effect on or change to the target structure. Kits containing products or compositions formulated or configured and systems for use in practicing these methods.

163 Claims, 35 Drawing Sheets

(51) Int. Cl.
    *A61B 18/18*     (2006.01)
    *B82Y 30/00*     (2011.01)
    *A61N 1/40*     (2006.01)
    *A61N 5/02*     (2006.01)
    *A61N 5/10*     (2006.01)
    *A61N 5/067*     (2006.01)

(52) U.S. Cl.
CPC ......... *A61N 5/0616* (2013.01); *A61N 5/0618* (2013.01); *A61N 5/0624* (2013.01); *A61N 5/0625* (2013.01); *A61N 5/10* (2013.01); *A61B 18/18* (2013.01); *A61B 2018/00351* (2013.01); *A61B 2018/00577* (2013.01); *A61N 5/067* (2021.08); *A61N 5/0622* (2013.01); *A61N 2005/0612* (2013.01); *A61N 2005/0659* (2013.01); *A61N 2005/0661* (2013.01); *A61N 2005/0663* (2013.01); *A61N 2005/1089* (2013.01); *B82Y 30/00* (2013.01)

(58) Field of Classification Search
CPC ...... A61N 5/0624; A61N 5/0625; A61N 5/10; A61N 1/40; A61N 5/067; A61N 5/0622; A61N 2005/0612; A61N 2005/0659; A61N 2005/0661; A61N 2005/0663; A61N 2005/1089; A61B 18/18; A61B 2018/00351; A61B 2018/00577; A61K 41/00; A61K 41/0057; A61K 41/0066
See application file for complete search history.

(56) References Cited

U.S. PATENT DOCUMENTS

| | | | | |
|---|---|---|---|---|
| 5,533,508 A * | 7/1996 | Doiron | A61B 5/0059 | 600/317 |
| 5,773,609 A * | 6/1998 | Robinson | A61P 9/10 | 540/122 |
| 5,829,448 A * | 11/1998 | Fisher | A61K 41/008 | 604/20 |
| 6,899,723 B2 * | 5/2005 | Chen | A61P 9/00 | 604/21 |
| 7,306,620 B2 * | 12/2007 | Cumbie | A61N 5/0616 | 606/9 |
| 7,422,598 B2 * | 9/2008 | Altshuler | A61B 18/203 | 607/93 |
| 7,575,589 B2 * | 8/2009 | De Taboada | A61N 5/0613 | 607/88 |
| 8,197,471 B1 * | 6/2012 | Tersigni | A61N 5/1001 | 606/27 |
| 2002/0127224 A1 * | 9/2002 | Chen | A61K 39/44 | 424/130.1 |
| 2005/0182461 A1 * | 8/2005 | Hubert | B82Y 10/00 | 607/88 |
| 2007/0218049 A1 * | 9/2007 | Chen | B82Y 5/00 | 424/130.1 |
| 2008/0139993 A1 * | 6/2008 | Bensaoula | A61K 41/0071 | 378/65 |
| 2008/0248001 A1 * | 10/2008 | Bourke | A61K 31/366 | 514/454 |
| 2009/0104212 A1 * | 4/2009 | Bourke | A61P 37/00 | 514/21.2 |
| 2010/0003316 A1 * | 1/2010 | Vo Dinh | A61K 41/0028 | 424/93.7 |
| 2010/0016783 A1 * | 1/2010 | Bourke, Jr. | A61P 27/02 | 378/65 |
| 2011/0021970 A1 * | 1/2011 | Vo-Dinh | A61P 9/04 | 424/490 |
| 2011/0117202 A1 * | 5/2011 | Bourke, Jr. | A61N 1/40 | 977/773 |
| 2011/0177007 A1 * | 7/2011 | Rajagopalan | C09B 57/00 | 546/281.1 |
| 2012/0059307 A1 * | 3/2012 | Harris | A61K 9/5146 | 977/773 |
| 2012/0064134 A1 * | 3/2012 | Bourke, Jr. | A61Q 1/04 | 106/287.18 |
| 2013/0289132 A1 * | 10/2013 | Greuel | C09K 11/0822 | 514/769 |
| 2013/0304162 A1 * | 11/2013 | Veres | A61N 5/0613 | 607/88 |
| 2014/0074010 A1 * | 3/2014 | Veres | A61N 5/06 | 604/20 |
| 2014/0323946 A1 * | 10/2014 | Bourke, Jr. | A61K 41/0085 | 604/20 |

OTHER PUBLICATIONS

Office Action dated Feb. 26, 2018 in European Patent Application No. 15 833 297.3.
Office Action dated Jun. 1, 2018 in European Patent Application No. 15833297.3, 1 page.
Extended European Search Report dated May 14, 2018 in Patent Application No. 15833297.3, 6 pages.
Office Action dated Jul. 30, 2020 in corresponding European Patent Application No. 15 833 297.3, 4 pages.

* cited by examiner

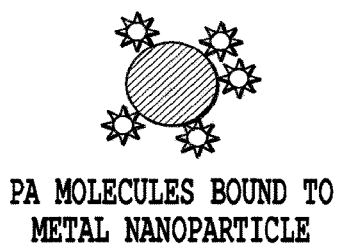
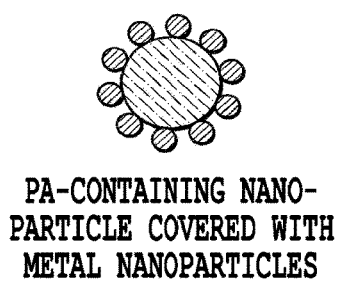

PA MOLECULES BOUND TO METAL NANOPARTICLE

*Fig. 7A*

PA-CONTAINING NANO-PARTICLE COVERED WITH METAL NANOPARTICLES

*Fig. 7B*

☼ PHOTO-ACTIVE (PA) MOLECULE (PHOTOSENSITIZER)

▧ METAL (e.g. Au,Ag)

▨ MATERIAL CONTAINING PA

▥ PROTECTIVE COATING

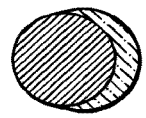
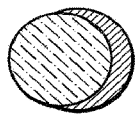

METAL NANOPARTICLE COVERED WITH PA NANOCAP

*Fig. 7C*

PA-CONTAINING NANO-PARTICLE COVERED WITH METAL NANOCAP

*Fig. 7D*

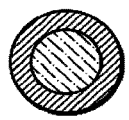

METAL NANOPARTICLE COVERED WITH PA NANOSHELL

*Fig. 7E*

PA-CONTAINING NANO-PARTICLE COVERED WITH METAL NANOSHELL

*Fig. 7F*

PA-CONTAINING NANO-PARTICLE COVERED WITH METAL NANOSHELL WITH PROTECTIVE COATING LAYER

*Fig. 7G*

NANOPARTICLE IMPROVES DELIVERY OF PA MOLECULES INTO TARGET DISEASED CELLS

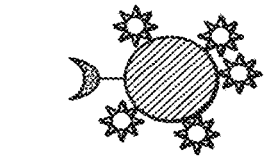

PA MOLECULES BOUND TO
METAL NANOPARTICLE

*Fig. 12A*
PRIOR ART

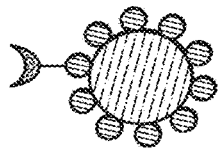

PA-CONTAINING NANO-
PARTICLE COVERED WITH
METAL NANOPARTICLES

*Fig. 12B*
PRIOR ART

☼ PHOTO-ACTIVE (PA) MOLECULE (PHOTOSENSITIZER)

⊂ BIORECEPTOR (Ab, DNA, etc.)

▨ METAL (e.g. Au, Ag)

▧ MATERIAL CONTAINING PA

▦ PROTECTIVE COATING

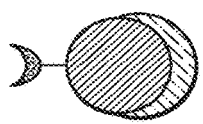

METAL NANOPARTICLE
COVERED WITH PA NANOCAP

*Fig. 12C*
PRIOR ART

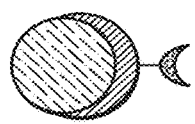

PA-CONTAINING NANO-
PARTICLE COVERED WITH
METAL NANOCAP

*Fig. 12D*
PRIOR ART

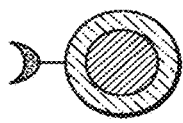

METAL NANOPARTICLE
COVERED WITH PA NANOSHELL

*Fig. 12E*
PRIOR ART

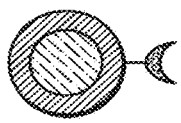

PA-CONTAINING NANO-
PARTICLE COVERED WITH
METAL NANOSHELL

*Fig. 12F*
PRIOR ART

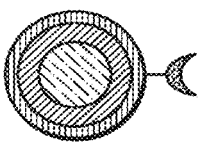

PA-CONTAINING NANO-
PARTICLE COVERED WITH
METAL NANOSHELL WITH
PROTECTIVE COATING LAYER

*Fig. 12G*
PRIOR ART

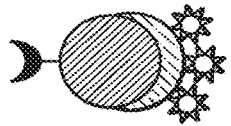

PA MOLECULES BOUND TO
EEC AND TO PLASMONIC
METAL NANOPARTICLE

*Fig. 15A*

PRIOR ART

PLASMONIC AND METAL NANO-
PARTICLE WITH EEC NANOCAP
COVERED WITH PA MOLECULES

*Fig. 15B*

PRIOR ART

☆ PHOTO-ACTIVE (PA) MOLECULE (PHOTOSENSITIZER)

◖ OPTIONAL BIORECEPTOR (Ab, DNA, etc)

▨ PLASMONICS-ACTIVE MATERIAL (e.g. Au, Ag)

▨ EXCITATION ENERGY CONVERTER (EEC) MATERIAL

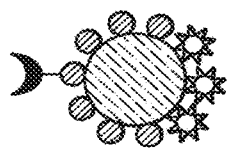
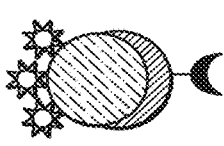

PA-COVERED NANOPARTICLE
WITH PLASMONIC METAL
NANOPARTICLES

*Fig. 15C*

PRIOR ART

EEC-CONTAINING NANOPARTICLE
COVERED WITH PA MOLECULES AND
PLASMONIC METAL NANOCAP

*Fig. 15D*

PRIOR ART

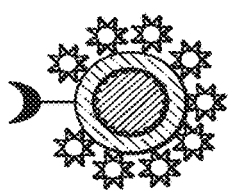

INSIDE THE CELL, PHOTON RADIATION
RELEASES PA WHICH CAN GO TO TARGET
AREA (e.g., NUCLEUS)

PLASMONIC METAL NANOPARTICLE
CORE WITH EEC NANOSHELL
COVERED WITH PA MOLECULE

*Fig. 15E*

PRIOR ART

PA MOLECULE BOUND TO EEC (ATTACHED TO
PLASMONICS METAL NANOPARTICLE) NANOPARTICLE
BY DETACHABLE BIOCHEMICAL BOND

*Fig. 15F*

PRIOR ART

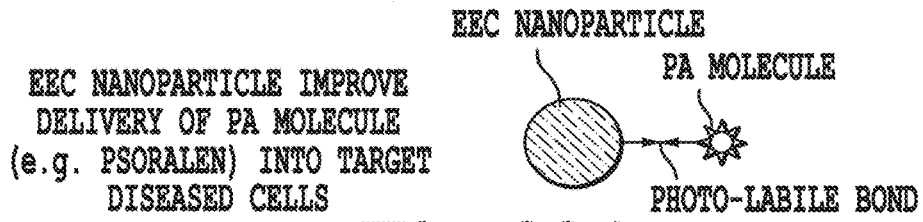
Fig.20A
PRIOR ART
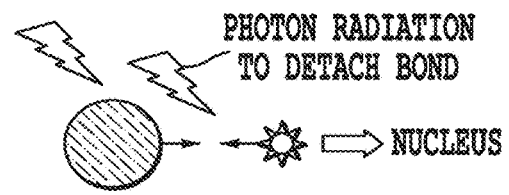
Fig 20B
PRIOR ART
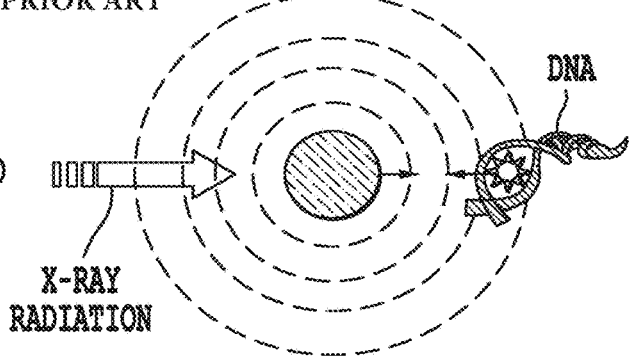
Fig.20C
PRIOR ART
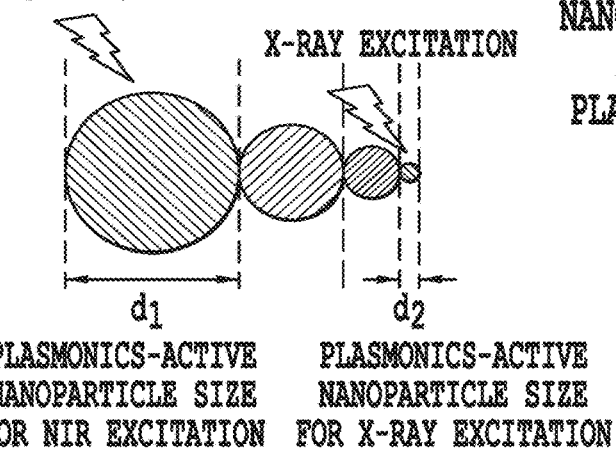 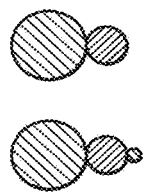
Fig.21
PRIOR ART

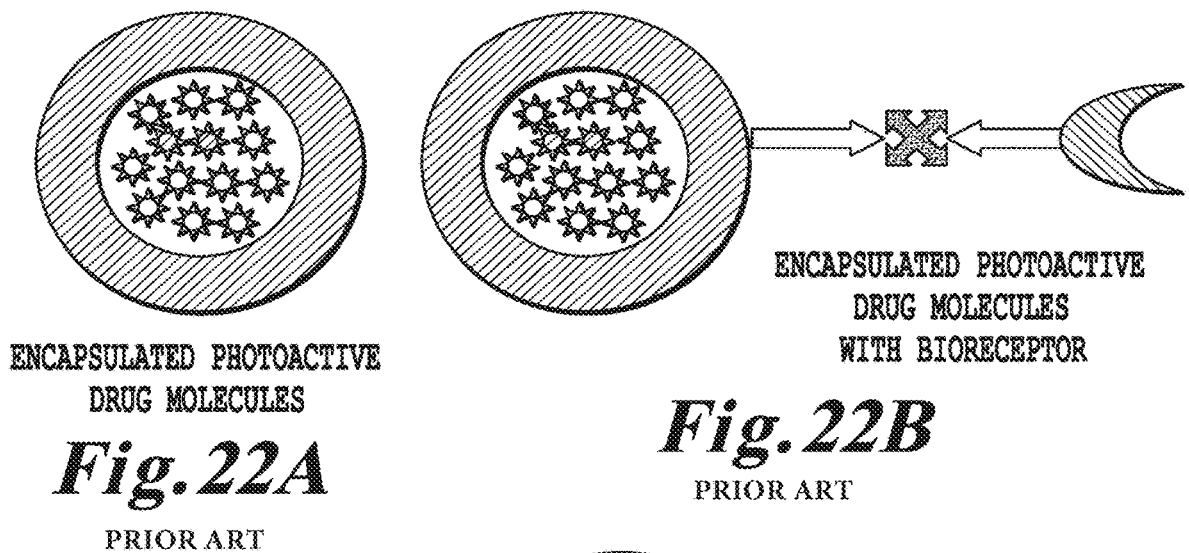
Fig.22A
ENCAPSULATED PHOTOACTIVE DRUG MOLECULES
PRIOR ART
Fig.22B
ENCAPSULATED PHOTOACTIVE DRUG MOLECULES WITH BIORECEPTOR
PRIOR ART
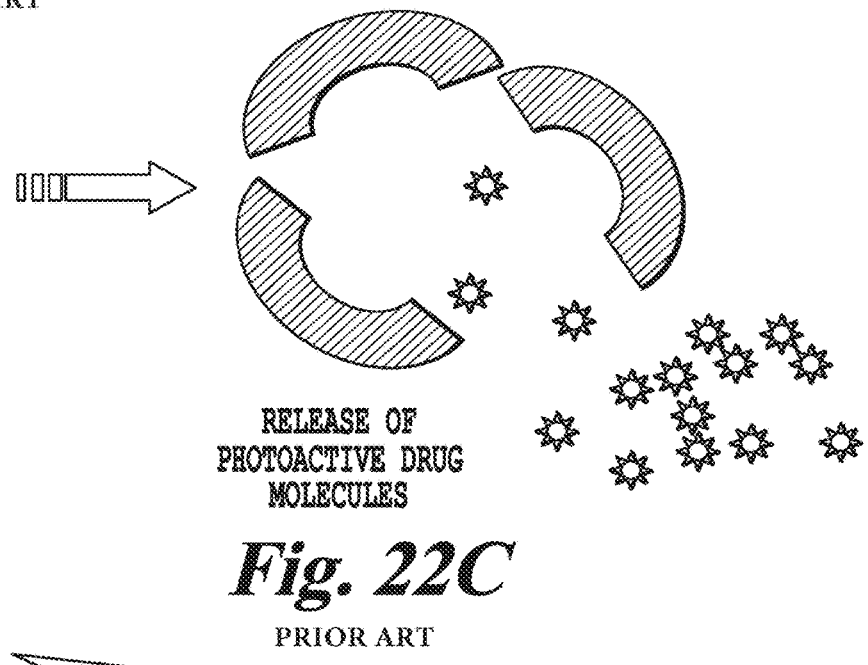
RELEASE OF PHOTOACTIVE DRUG MOLECULES
Fig. 22C
PRIOR ART
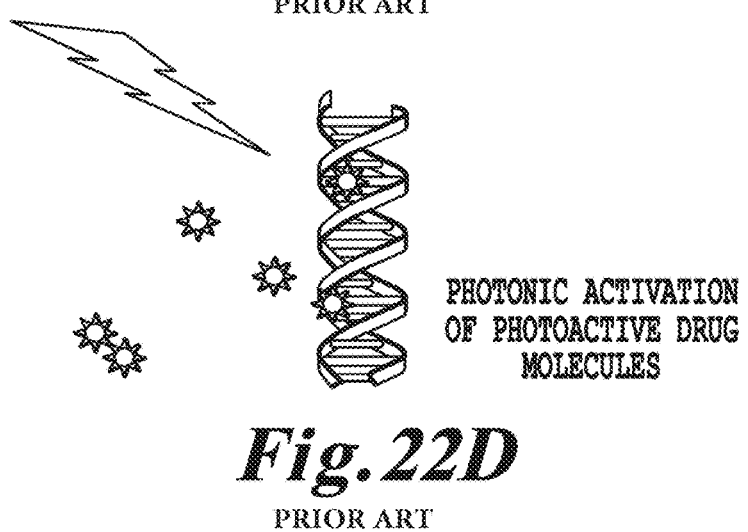
PHOTONIC ACTIVATION OF PHOTOACTIVE DRUG MOLECULES
Fig.22D
PRIOR ART

EXCITON INDUCED PHOTOTHERAPY

☆ PHOTO-ACTIVE (PA) MOLECULE (e.g. PSORALEN)

▨ METAL (e.g. Au, Ag)

▨ MATERIAL CONTAINING X-RAY ENERGY CONVERTER

▥ PROTECTIVE COATING (BIOCOMPATIBLE, NON-TOXIC LAYER)

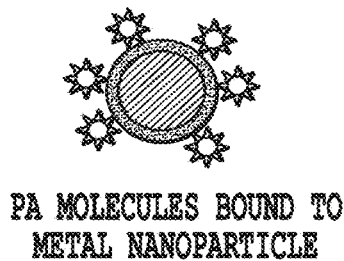

PA MOLECULES BOUND TO METAL NANOPARTICLE

*Fig. 34A*

PRIOR ART

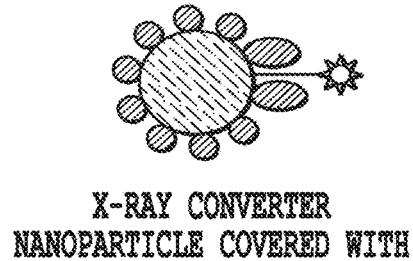

X-RAY CONVERTER NANOPARTICLE COVERED WITH METAL NANOPARTICLES

*Fig. 34B*

PRIOR ART

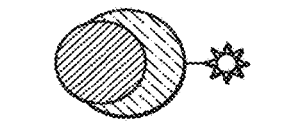

METAL NANOPARTICLE COVERED WITH X-RAY CONVERTER NANOCAP

*Fig. 34C*

PRIOR ART

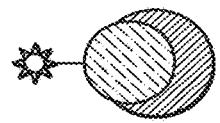

X-RAY CONVERTER NANOPARTICLE COVERED WITH METAL NANOCAP

*Fig. 34D*

PRIOR ART

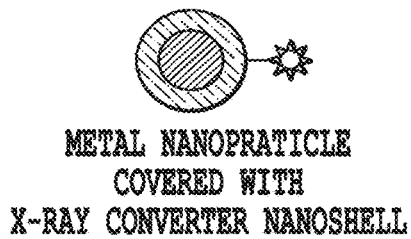

METAL NANOPRATICLE COVERED WITH X-RAY CONVERTER NANOSHELL

*Fig. 34E*

PRIOR ART

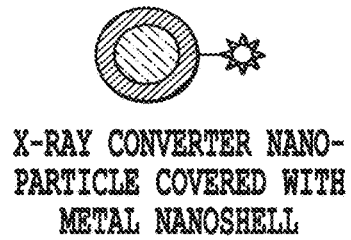

X-RAY CONVERTER NANO-PARTICLE COVERED WITH METAL NANOSHELL

*Fig. 34F*

PRIOR ART

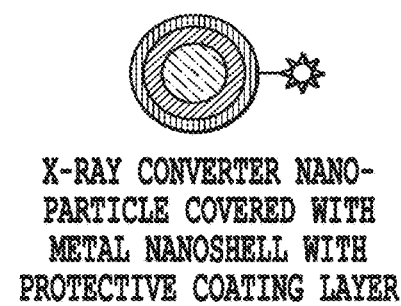

X-RAY CONVERTER NANO-PARTICLE COVERED WITH METAL NANOSHELL WITH PROTECTIVE COATING LAYER

*Fig. 34G*

PRIOR ART

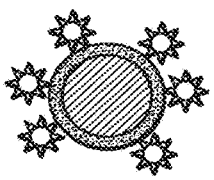

PA MOLECULES BOUND TO
METAL NANOPARTICLE

*Fig.35A*

PRIOR ART

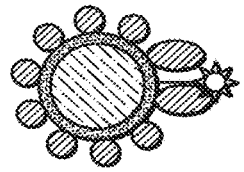

X-RAY CONVERTER
NANOPARTICLE COVERED WITH
DIELECTRIC LAYER AND
METAL NANOPARTICLES

*Fig.35B*

PRIOR ART

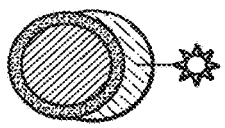

METAL NANOPARTICLE
COVERED WITH DIELECTRIC LAYER
AND X-RAY CONVERTER NANOCAP

*Fig.35C*

PRIOR ART

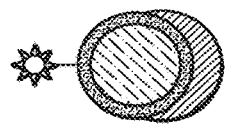

X-RAY CONVERTER NANOPARTICLE
COVERED WITH DIELECTRIC LAYER
AND METAL NANOCAP

*Fig.35D*

PRIOR ART

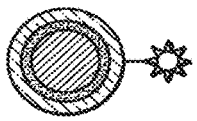

METAL NANOPARTICLE
COVERED WITH DIELECTRIC
LAYER AND X-RAY
CONVERTER NANOSHELL

*Fig.35E*

PRIOR ART

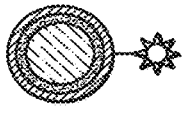

X-RAY CONVERTER NANO-
PARTICLE COVERED WITH
DIELECTRIC LAYER AND
METAL NANOSHELL

*Fig.35F*

PRIOR ART

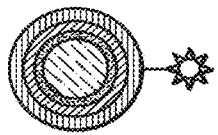

*Fig.35G*

PRIOR ART

✦ PHOTO-ACTIVE (PA) MOLECULE (e.g. PSORALEN)

▨ METAL (e.g. Au, Ag)

▦ PROTECTIVE COATING (BIOCOMPATIBLE, NON-TOXIC LAYER)

▨ DIELECTRIC LAYER (e.g. SILICA)

▨ MATERIAL CONTAINING X-RAY ENERGY CONVERTER

NON-INVASIVE SYSTEMS AND METHODS FOR SELECTIVE ACTIVATION OF PHOTOREACTIVE RESPONSES

CROSS REFERENCE TO RELATED APPLICATIONS

The present application claims priority to U.S. provisional application 62/038,674, filed Aug. 18, 2014 and is related to U.S. Ser. No. 12/417,779 filed, Apr. 3, 2009, entitled "NON-INVASIVE SYSTEMS AND METHODS FOR IN-SITU PHOTOBIOMODULATION," the entire contents of which are hereby incorporated by reference. The present application is related to U.S. Provisional application Ser. No. 61/955,131, filed May 18, 2014, the entire contents of which are hereby incorporated by reference. The present application is related to U.S. Provisional application Ser. No. 61/331,990, filed May 6, 2010, and U.S. Provisional application Ser. No. 61/443,019, filed Feb. 15, 2011, the entire contents of each of which are hereby incorporated by reference. The present application is also related to U.S. provisional patent application 61/161,328, filed Mar. 18, 2009; U.S. provisional patent application 61/259,940, filed Nov. 10, 2009; U.S. Provisional Applications Ser. No. 60/954,263, filed Aug. 6, 2007, and 61/030,437, filed Feb. 21, 2008; U.S. application Ser. No. 12/059,484, filed Mar. 31, 2008; U.S. application Ser. No. 11/935,655, filed Nov. 6, 2007; U.S. Provisional Applications Ser. No. 61/042,561, filed Apr. 4, 2008; 61/035,559, filed Mar. 11, 2008; and 61/080,140, filed Jul. 11, 2008; U.S. patent application Ser. No. 12/401,478 filed Mar. 10, 2009; U.S. patent application Ser. No. 11/935,655, filed Nov. 6, 2007; U.S. patent application Ser. No. 12/059,484, filed Mar. 31, 2008; U.S. patent application Ser. No. 12/389,946, filed Feb. 20, 2009; and U.S. patent application Ser. No. 12/417,779, filed Apr. 3, 2009, the entire contents of each of which is hereby incorporated by reference. This application is related to U.S. patent application Ser. No. 12/763,404 filed Apr. 20, 2010, the entire contents of which are hereby incorporated by reference. This application is related to U.S. patent application Ser. No. 12/843,188 filed Jul. 26, 2010, the entire contents of which are hereby incorporated by reference. This application is related to U.S. patent application Ser. No. 12/891,466 filed Sep. 27, 2010, the entire contents of which are hereby incorporated by reference. This application is related to U.S. patent application Ser. No. 12/943,787 filed Nov. 10, 2010, the entire contents of which are hereby incorporated by reference. This application is related to U.S. patent application Ser. No. 13/054,279 filed Jul. 13, 2011, the entire contents of which are hereby incorporated by reference. This application is related to U.S. patent application 61/505,849 filed Jul. 8, 2011, the entire contents of which are hereby incorporated by reference. This application is related to U.S. patent application Ser. No. 13/102,277 filed May 6, 2011, the entire contents of which are hereby incorporated by reference. This application is related to U.S. patent application Ser. No. 13/204,355 filed Aug. 5, 2011, the entire contents of which are hereby incorporated by reference. This application is related to U.S. patent application 61/735,754 filed Dec. 11, 2012, the entire contents of which are hereby incorporated by reference. This application is related to U.S. patent application 62/014,561 filed Jun. 19, 2014, the entire contents of which are hereby incorporated by reference. This application is related to U.S. patent application 61/792,125 filed Mar. 15, 2013, the entire contents of which are hereby incorporated by reference. This application is related to U.S. patent application 61/930,717 filed Jan. 23, 2014, the entire contents of which are hereby incorporated by reference. This application is related to U.S. patent application 61/955,131 filed Mar. 18, 2014, the entire contents of which are hereby incorporated by reference. This application is related to U.S. patent application 61/955,547 filed Mar. 19, 2014, the entire contents of which are hereby incorporated by reference. This application is related to U.S. patent application Ser. No. 14/103,084 filed Dec. 11, 2013, the entire contents of which are hereby incorporated by reference. This application is related to U.S. patent application Ser. No. 14/131,564 filed Jul. 11, 2014, the entire contents of which are hereby incorporated by reference. This application is related to U.S. patent application Ser. No. 14/206,337 filed Mar. 12, 2014, the entire contents of which are hereby incorporated by reference. This application is related to U.S. patent application 62/018,915 filed Jun. 30, 2014, the entire contents of which are hereby incorporated by reference.

BACKGROUND OF THE INVENTION

Field of Invention

The present invention relates to methods and systems for treating a disorder or condition in a subject.

Discussion of the Background

Photobiomodulation

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

Certain wavelengths of light at certain intensities (delivered by laser, light emitting diode LED or another monochromatic source) will, for example, aid tissue regeneration, resolve inflammation, relieve pain and boost the immune system. The exact mechanism is still being explored and debated but it is agreed that the mechanism is photochemical rather than heat-related. Observed biological and physiological effects include changes in cell membrane permeability, and up-regulation and down-regulation of adenosine triphosphate and nitric oxide.

Light-induced biological effects depend on the parameters of the irradiation (wavelength, dose, intensity, irradiation time, depth of a target cell, and continuous wave or pulsed mode, pulse parameters). (See, e.g., Karu I T, Low-Power Laser Therapy", in Biomedical Photonics Handbook, Vo-Dinh T. Ed., CRC Press, Boca Raton, Fla., pp. 48-1 to 48-25, (2003)). Laser average power is typically in the range of 1-500 mW; some high peak power, short pulse width devices are in the range of 1-100 W with typically 200 ns pulse widths. The average beam irradiance then is typically 10 $mW/cm^2$-5 $W/cm^2$. The wavelength is typically in the range 600-1000 nm. The red-to-near infrared (NIR) region is preferred for photobiomodulation. Other wavelengths may be also used, e.g., UV light for neurons and green light for prostate tissue. Maximum biological responses often occur when irradiated at 620, 680, 760, and 820-830 nm (Karu T I, et al., (1998). The Science of Low Power Laser Therapy. Gordon and Breach Sci. Publ., London). Large volumes and relatively deeper layers of tissues can be successfully irradiated by laser only (e.g., inner and middle ear diseases, injured siatic or optical nerves, inflammations). The LEDs are used for irradiation of surface injuries.

A photoacceptor first absorbs the light used for the irradiation. After promotion of electronically excited states, primary molecule processes from these states can lead to a measurable biological effect (via secondary biochemical reaction, or photosignal transduction cascade, or cellular signaling) at the cellular level. A photoacceptor for eukaryotic cells in red-to-NIR region is believed to be the terminal enzyme of the respiratory chain cytochrome c oxidase located in cell mitochondrion. In the violet-to blue spectra region, flavoprotein (e.g., NADHdehydrogenase in the beginning of the respiratory chain) is also among the photoacceptors.

Clinical applications of photobiomodulation include, for example, treating soft tissue and bone injuries, chronic pain, wound healing, nerve regeneration, sensory regeneration/restoration and possibly even resolving viral and bacterial infections, treating neurological and psychiatric diseases (e.g., epilepsy and Parkinson's disease) (e.g., Zhang F., et al., Nature, 446:617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One clinical application showing great promise is the treatment of inflammation, where the anti-inflammatory effect of location-and-dose-specific laser irradiation produces similar outcomes as NSAIDs, but without the potentially harmful side-effects (Bjordal J M, Couppé C, Chow R T, Tuner J, Ljunggren E A (2003). "A systematic review of low level laser therapy with location-specific doses for pain from chronic joint disorders". The Australian journal of physiotherapy 49(2):107-16).

An NIR light treatment can prevent cell death (apoptosis) in cultured neurons (brain) cells (Wong-Reiley M T, et al., JBC, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)).

It has also been shown that light has both inductive and inhibitory effect on cell growth and division in a red tide flagellate, *Chattonella antique* (Nemote Y., Plant and Cell Physiol., 26(4):669-674 (1985)).

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells via absorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)).

When photoacceptors absorb photons, electronic excitation followed by photochemical reactions occurring from lower excitation states (first singlet and triplet) take place. It is also known that electronic excitation of absorbing centers alters their redox properties. Until yet, five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu T I, et al., (1998). The Science of Low Power Laser Therapy. Gordon and Breach Sci. Publ., London).

Photobiological action via activation of respiratory chain is believed to be a general mechanism occurring in cells. Crucial events of this type of cell metabolism activation are occurring due to a shift of cellular redox potential into more oxidized direction as well as due to ATP extra synthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes).

Far red and NIR radiation have been shown to promote wound healing, e.g., infected, ischemic, and hypoxic wounds (Wong-Reley, W T T, JBC, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Other clinical applications of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vasc. Interv. Radiol., 18(6):811 (2007)). When the laser is slowly withdrawn, heat is applied to the vein walls, causing the vein to permanently close and disappear.

Yet, another area of application of photobiomodulation is a direct control (or modulation) of brain cell activity with light. The technique is based upon NIR spectroscopy and is simpler to use and less expensive than other methods such as functional magnetic resonance imaging and positron emission tomography.

Photostimulation can be used to activate a light-sensitive protein such as rhodopsin (ChR2), which can then excite the cell expressing the opsin.

It has been shown that channelrhodopsin-2, a monolithic protein containing a light sensor and a cation channel, provides electrical stimulation of appropriate speed and magnitude to activate neuronal spike firing. Recently, photoinhibition, the inhibition of neural activity with light, has become feasible with the application of molecules such as the light-activated chloride pump halorhodopsin to neural control. Together, blue-light activated channelrhodopsin-2 and the yellow light-activated chloride pump halorhodopsin enable multiple-color, optical activation and silencing of neural activity.

ChR2 photostimulation involves genetic targeting ChR2 to neurons and light pulsing the neurons expressing ChR2 protein. The experiments have been conducted in vitro and in vivo in mice by in vivo deep-brain photostimulation using optical fibers to deliver light into the lateral hypothalamus (Adamantidis A R, et al., Nature 450:420-425 (2007)). Genetic targeting of ChR2 allows exclusive stimulation of defined cellular subsets and avoids the need for addition of the caged glutamate, facilitating photostimulation in vivo (Wang H., et al., PNAS, 104(19):8143-48 (2007)). ChR2 photostimulation has been used for restoring visual activity in mice with impaired vision, to evoke behavioral responses in worms and flies (Wang H., et al., 2007). The robust associative learning induced by ChR2-assisted photostimulaiton in mice opens the door to study the circuit basis of perception and cognition in vivo (Huber D., et al., 2007). This kind of neuronal targeting and stimulation might have clinical application, e.g., deep brain stimulation to treat Parkinson's disease and other disorders, controlling behavioral, perceptional and cognitive characteristics, and for imaging and studying how the brain works (Zhang F., et al., Nature Methods, 3(10):785-792 (2006); Wong-Riley M T., et al., JBC, 280(6):4761-4771 (2005)).

Another gene, chloride pump (NpHR), which is borrowed from a microbe called an archaebacterium, can make neurons less active in the presence of yellow light. Combined, the two genes ChR2 and NpHR can now make neurons obey pulses of light like drivers obey a traffic signal: Blue means "go" (emit a signal), and yellow means "stop" (don't emit).

Light-sensitive proteins can be introduced into cells or live subjects via a number of techniques including electroporation, DNA microinjection, viral delivery, liposomal transfection and calcium-phosphate precipitation.

A third photostimulation technique is chemical modification of ion channels and receptors to render them light-responsive. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms.

In living organisms, scientists were able to cause worms, C. elegans, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior.

Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. They resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients. By allowing researchers to selectively stimulate or dampen different neurons in the brain, the light stimulation techniques could help in determining which particular neurons are benefiting from deep brain stimulation.

Another potential application involves simulating neural communications. Because neurons communicate by generating patterns of signals-sometimes on and sometimes off like the 0s and 1s of binary computer code-flashing blue and yellow lights in these patterns could compel neurons to emit messages that correspond to real neural instructions. The ability to artificially stimulate neural signals, such as movement instructions, could allow doctors to bridge blockages in damaged spinal columns, perhaps restoring some function to the limbs of paralyzed patients.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from O2 dissolved in cells, similar to photodynamic effect (Zakharov S D, et al., Quantum Electronics, 29(12):1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE).

Problems with LLLT, Cold Laser Therapy, and Laser Biostimulation

The laser systems currently used for biostimulation do not allow performing photobiomodulation in a region deep within thick tissue without a surgical invasion. Laser therapy is mostly conducted in surface or near surface target cells and tissue because penetration of UV and red-to-N IR radiation used for photobiomodulation and photobiostimulaiton is no more than a few centimeters beneath the surface of the skin. In addition, imaging and stimulation of brain cells is mainly possible in thin brain slices, or a thin monolayer or suspension of cells. For deeper tissue laser therapy in situ, a subject undergoes various invasive surgical procedures, e.g., invasive insertion of a fiber via incisions into a fat layer or veins, implanting a radiation source in deep tissue, or implanting a glass window above the barrel cortex (Huber D., et al., Nature, 451:61-66 (2007)). It is further well recognized that another problem associated with the existing methods of photobiomodulation is in differentiation of normal cells from target cells.

Phototherapy

There are two main types of reactions in phototherapy:
(1) Type I reactions involve electrons and hydrogen atoms, which are transferred between photo-active molecules (also called photosensitizers) and substrates or solvent molecules. Oxygen may participate in subsequent reactions: e.g., psoralens in photopheresis and PUVA.

(2) Type II reactions involve singlet oxygen formation by energy transfer from PA molecules in the lowest triplet state to oxygen in the ground state: e.g., photodynamic therapy (PDT)

Photodynamic therapy (PDT) is a treatment modality that uses a photosensitizing agent and laser light to kill cells. PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in *Biomedical Photonics Handbook*, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

$$PA + h\nu \rightarrow {}^1PA^*(S) \text{ Excitation}$$

$$^1PA^*(S) \rightarrow {}^3PA^*(T) \text{ Intersystem crossing for singlet to triplet state}$$

$$^3PA^*(T) + O_2 \rightarrow {}^1O^*_2 + PA \text{ Energy transfer from the drug to singlet oxygen}$$

where PA=photo-active drug at the ground state; $^1PA^*(S)$=excited singlet state; $^3PA^*(T)$=excited triplet state; $^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

An important mechanism associated with PDT drug activity involves apoptosis in cells. Upon absorption of light, the photosensitiser (PS) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "*Synthetic Strategies in designing Porphyrin-Based Photosensitizers*', in *Biomedical Photonics Handbook*, Vo-Dinh T., Ed., CRC Press, Boca Raton Fla. (2003)], chlorines, phthalocyanine, and naphthalocyanine have been investigated.

PDT retains several photosensitizers in tumors for a longer time than in normal tissues, thus offering potential improvement in treatment selectivity. See Corner C., "Determination of [3H]- and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favorable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly damaged structures.

Photopheresis has been successfully used for treatment of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known.

Other successful application of PDT is, for example, cardiac ablasion therapy, e.g., treating cardiac arrhythmias and atrial fibrillation which are believed to be a significant cause of cerebral stroke.

U.S. Pat. No. 6,811,562 describes administering a photo-activatable agent and subjecting cardiac tissue containing the administered agent to laser irradiation having a wavelength from 350 to 700 nm using invasive techniques, e.g., a fiber optic element.

Yet, another application of PDT is photoangioplasty for arterial diseases including de novo atherosclerosis and restinosis (Rockson A G, et al., Circulation, 102:591-596 (2000); Hsiang Y N., et al., J. Endovasc. Surg., 2:365-371 (1995)). In human clinical applications, endovascular light (730 nm) is delivered through a cylindrical fiber after intravenous administration of motexafin lutetium. PDT is also used for preventing and treatment of intimal hyperplasia in blood vessels in vivo (see, e.g., U.S. Pat. No. 6,609,014).

Age-related macular degeneration (AMD) is a cause of new blindness. Choroidal neovascularization leads to hemorrhage and fibrosis in a number of ocular diseases. Conventional treatments utilize the argon laser to occlude the leaking vessel by thermal coagulation. However, the percentage of patients eligible for this treatment is limited. PDT is used for treating AMD and involves injecting verteporfin followed by the application of non-thermal light at 692 nm.

Improvement of clinical appearance of psoriatic plaques and palmopustular psoriasis using PUVA with hematopotphyrin was first reported in 1937. Acne, apopecia areata, portwine stains and hair removal also show promise with PDT treatment.

In one existing treatment known as extracorporeal photopheresis (ECP), excellent results have been observed since its initial approval by the FDA in 1988.

Extracorporeal photopheresis (ECP) is a leukapheresis-based immunomodulatory therapy that has been approved by the US Food and Drug Administration for the treatment of cutaneous T-cell lymphoma (CTCL). ECP, also known as extracorporeal photochemotherapy, is performed at more than 150 centers worldwide for multiple indications. Long-term follow-up data are available from many investigators that indicate ECP produces disease remission and improved survival for CTCL patients. In addition to CTCL, ECP has been shown to have efficacy in the treatment of other T-cell mediated disorders, including chronic graft versus host disease (GVHD) and solid organ transplant rejection. ECP use for the treatment of autoimmune disease, such as systemic sclerosis and rheumatoid arthritis, is also being explored.

ECP is generally performed using the UVAR XTS Photopheresis System developed by Therakos, Inc (Exton, Pa.). The process is performed through one intravenous access port and has 3 basic stages: (1) leukapheresis, (2) photoactivation, and (3) reinfusion, and takes 3-4 hours to complete. A typical treatment session would resemble the following sequence of events:

(1) One 16-gauge peripheral intravenous line or central venous access is established in the patient;

(2) Blood (225 mL) is passed through 3 cycles of leukapheresis, or 125 mL of blood is passed through 6 cycles, depending on the patient's hematocrit value and body size. At the end of each leukapheresis cycle, the red blood cells and plasma are returned to the patient;

(3) The collected WBCs (including approximately 5% of the peripheral blood mononuclear cells) are mixed with heparin, saline, and 8-methoxypsoralen (8-MOP), which intercalates into the DNA of the lymphocytes upon exposure to UVA light and makes them more susceptible to apoptosis when exposed to UVA radiation;

(4) The mixture is passed as a 1-mm film through a sterile cassette surrounded by UVA bulbs, resulting in an average UVA exposure of 2 J/cm$^2$; and (5) The treated WBC mixture is returned to the patient.

Over the past 20 years, on-going research has explored the mechanism of action of ECP. The combination of 8-MOP and UVA radiation causes apoptosis of the treated T cells and may cause preferential apoptosis of activated or abnormal T cells, thus targeting the pathogenic cells of CTCL or GVHD. However, given that only a small percentage of the body's lymphocytes are treated, this seems unlikely to be the only mechanism of action.

Other evidence suggests that ECP also induces monocytes to differentiate into dendritic cells capable of phagocytosing and processing the apoptotic T-cell antigens. When these activated dendritic cells are reinfused into the systemic circulation, they may cause a systemic cytotoxic CD8$^+$ T-lymphocyte-mediated immune response to the processed apoptotic T-cell antigens.

Finally, animal studies indicate that photopheresis may induce antigen-specific regulatory T cells, which may lead to suppression of allograft rejection or GVHD.

Alternatively, a patient can be treated in vivo with a photosensitive agent followed by the withdrawal of a sample from the patient, treatment with UV radiation in vitro (ex vivo), and re-injecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. Nos. 6,569,467; 6,204,058; 5,980,954; 6,669,965; 4,838,852; 7,045,124, and 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

U.S. Pat. No. 5,829,448 describes sequential and simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 describes methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue.

U.S. Pat. No. 5,957,960 describes a two-photon excitation device for administering a photodynamic therapy to a treatment site within a patient's body using light having an infrared or near infrared waveband.

U.S. Pat. No. 6,235,508 describes antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivation of substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

U.S. Pat. No. 6,235,508 suggests that halogenated photosensitizers and blocking agents might be suitable for replacing 8-methoxypsoralen (8-MOP) in photopheresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photopheresis for antiviral treatments of raw blood and plasma.

U.S. published application 2002/0127224 describes a method for a photodynamic therapy comprising administering light-emitting nanoparticles and a photoactivatable agent, which may be activated by the light re-emitted from the nanoparticles via a two-photon activation event. An initiation energy source is usually a light emitting diode, laser, incandescent lamp, or halogen light, which emits light having a wavelength ranging from 350 to 1100 nm. The initiation energy is absorbed by the nanoparticles. The nanoparticles, in turn, re-emit light having a wavelength from 500 to 1100 nm, preferably, UV-A light, wherein the re-emitted energy activates the photoactivatable agent. Kim et al., (JACS, 129:2669-75, 2/9/2007) describes indirect excitation of a photosensitizing unit (energy acceptor) through fluorescence resonance energy transfer (FRET) from the two-photon absorbing dye unit (energy donor) within an energy range corresponding to 300-850 nm.

Psoralens and Related Compounds

U.S. Pat. No. 6,235,508 describes that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

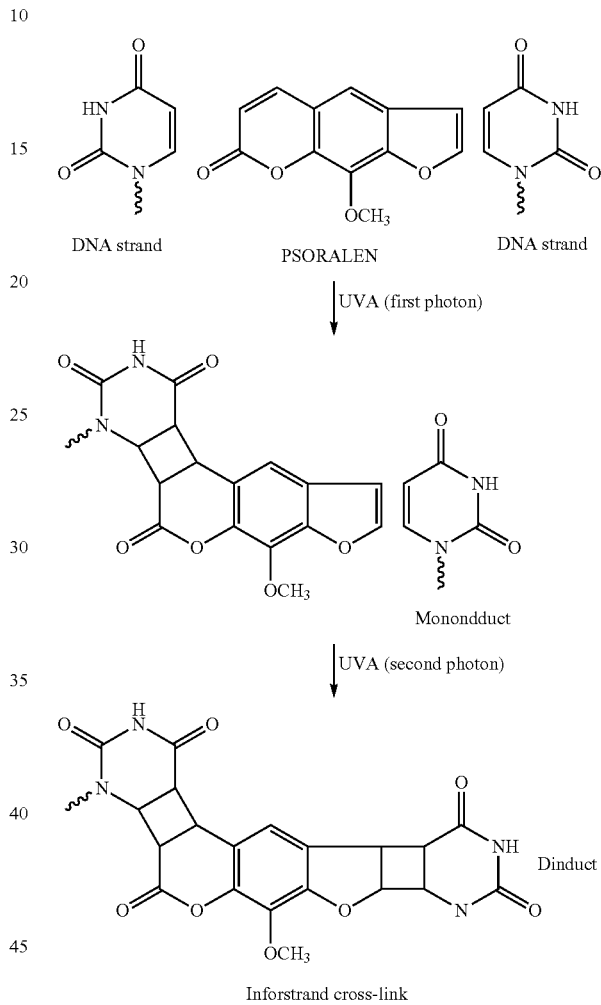

U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

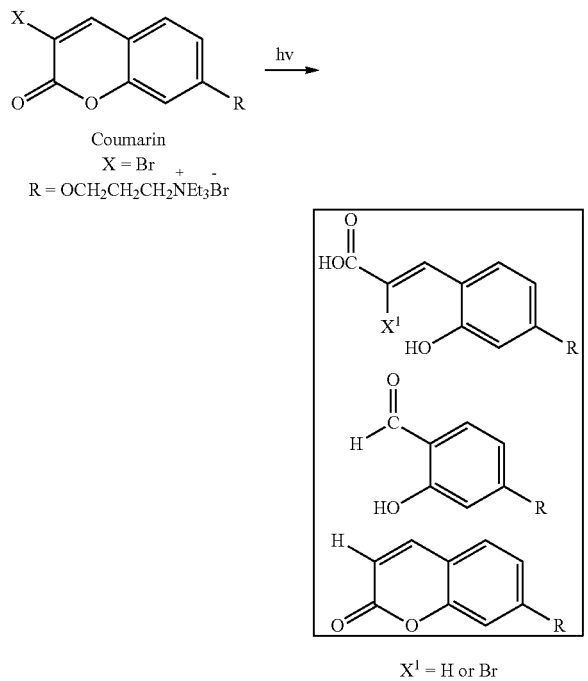

Research in this field over-simplifies mechanisms involved in the photoactivation mechanism and formation of highly reactive oxygen species, such as singlet oxygen. Both may lead to damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photopheresis causes the activation of an immune response with cytotoxic effects on untreated malignant cells.

Midden (W. R. Midden, Psoralen DNA photobiology, Vol I1 (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes.

U.S. Pat. No. 6,235,508 describes that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 describes a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference in its entirety.

U.S. Pat. No. 5,984,887 describes using extracorporeal photopheresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment. \

Problems with PDT

It is well recognized that a major problem associated with the existing methods of diagnosis and treatment of cell proliferation disorders is in differentiation of normal cells from target cells. Radiation therapy works by irradiating cells with high levels of high energy radiation such as high energy photon, electron, or proton. These high energy beams ionize the atoms which make up a DNA chain, which in turn leads to cell death. Unlike surgery, radiation therapy does not require placing patients under anesthesia and has the ability to treat disorders deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell from a diseased cell either. Another problem encountered in PDT therapy is the inability to treat target areas that are more than a few centimeters beneath the surface of the skin without significant invasive techniques.

SUMMARY OF THE INVENTION

Accordingly, one object of the present invention is to provide a method for the treatment of a condition, disorder or disease in a subject that permits treatment of a subject in any area of the body where the treatment selectively activates plural biological responses depending on a selection of the wavelength of light generated internally or provided internally within the body.

Thus, in one object of the present invention, there are provided a plurality of light emitters at different wavelengths corresponding to respective biological responses being activated by each of the different wavelengths.

A further object of the present invention is to provide a method for treatment of a condition, disorder or disease in a subject which can use any suitable energy source as the initiation energy source to induce a predetermined change in a target structure in a subject in situ to treat the condition, disorder or disease by way of the selective activation noted above.

A further object of the present invention is to provide a method for treatment of a condition, disorder or disease using a modulation agent which adsorbs, intensifies or modifies the initiation energy into an energy that effects a predetermined change in a target structure by way of the selective activation noted above.

These and other objects of the present invention, which will become more apparent in conjunction with the following detailed description of the preferred embodiments, either alone or in combinations thereof, have been satisfied by the discovery of a method for treating a condition, disorder or disease in a subject, comprising:

applying an initiation energy from at least one source to a target structure in a subject in need of treatment, wherein the initiation energy contacts the target structure and induces a predetermined change in said target structure in situ, thus treating said condition, disorder or disease.

Yet a further object of the invention is further administer at least one energy modulation agent to said subject which adsorbs, intensifies or modifies said initiation energy into an energy that effects a predetermined change in said target structure by way of the selective activation noted above.

A further object of the present invention is to provide a method for treatment of a condition, disorder or disease which can use any suitable energy source as the initiation energy source to activate the activatable pharmaceutical agent and thereby cause a predetermined change in a target structure to treat a condition, disorder or disease by way of the selective activation noted above.

A further object of the present invention is to provide a method for treatment of a condition, disorder or disease using an energy cascade to activate an activatable pharmaceutical agent that then treats cells suffering from a condition, disorder or disease by way of the selective activation noted above.

A further object of the present invention is to provide a method for generating an autovaccine effect in a subject, which can be in vivo thus avoiding the need for ex vivo treatment of subject tissues or cells, or can be ex vivo by way of the selective activation noted above.

A further object of the present invention is to provide a method for generating an autovaccine effect in a subject, which can be in vivo thus avoiding the need for ex vivo treatment of subject tissues or cells, or can be ex vivo by way of the selective activation noted above.

A further object of the present invention is to provide a computer implemented system for performing the methods of the present invention.

A still further object of the present invention is to provide a kit and a pharmaceutical composition for use in the present invention methods.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 3-1 illustrates an exemplary system according to one embodiment of the invention for producing a photo-reactive change in a medium.

FIGS. 7A-7G provide representative embodiments of plasmonics photo-active probes useful in the present invention.

FIGS. 8A-8B are graphical explanations of the plasmonics-enhanced effect of photospectral therapy used in the present invention.

FIGS. 9A-9J provide representative embodiments of plasmonics-active nanostructures.

FIGS. 12A-12G are graphical representations of several embodiments of plasmonics photo-active probes with bioreceptors.

FIGS. 15A-15F are graphical representations of several embodiments of plasmonics photo-active energy modulation agent-PA probes.

FIGS. 20A-20C are graphical representations of an embodiment of a PEPST energy modulation agent-PA system with detachable bond.

FIG. 21 is a graphical representation of an embodiment of PEPST probes for dual plasmonic excitation.

FIGS. 22A-22D are graphical representations of an embodiment of a use of encapsulated photoactive agents.

FIGS. 34A-34G show photo-active probes in which a photo-active molecule is bound to plasmonics probes.

FIGS. 35A-35G shows plasmonics photo-active probes that have a dielectric layer between the metal and the UC materials.

DETAILED DESCRIPTION OF THE INVENTION

Figure 1:
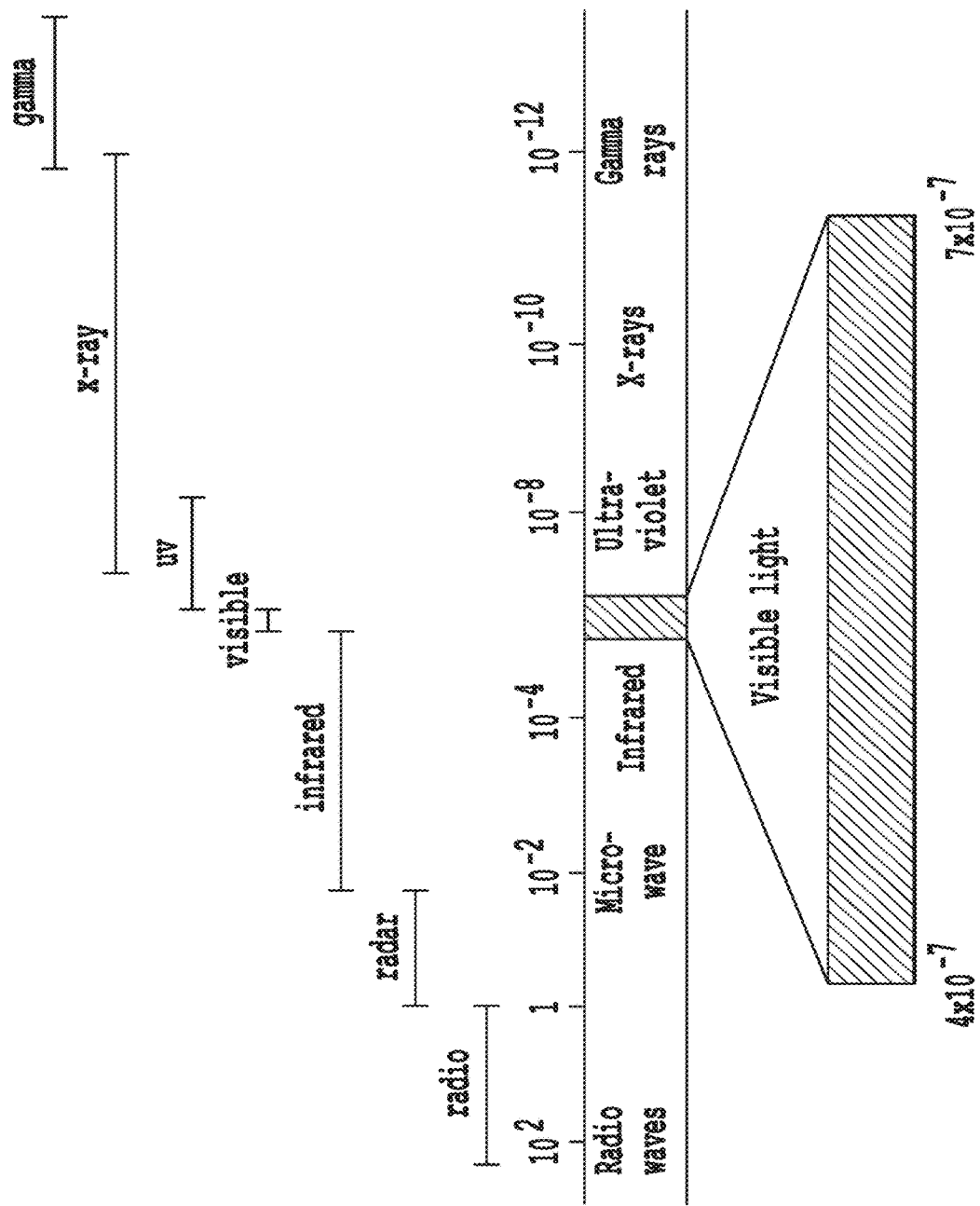
FIG. 1 provides an exemplary electromagnetic spectrum in meters (1 nm equals $10^{-9}$ meters).

The present invention sets forth a novel method of modifying a target structure which mediates or is associated with a biological activity, which includes treating a condition, disorder or disease in a subject. Those cells suffering from a condition, disorder or disease are referred to herein as the target cells.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

Generally, the present invention provides a method for affecting a change in biological activity, comprising:

providing in a vicinity of or within a target structure one or more light emitters capable of emitting different wavelengths corresponding to respective biological responses; and activating plural biological responses in the target structure depending on different wavelengths of light generated internally or provided internally within the subject, wherein the different wavelengths activate the respective biological responses (i.e., selective activation).

For example, as noted above, mechanisms involved in photoactivation of a drug such as psoralen and mechanisms involved in the formation of highly reactive oxygen species, such as singlet oxygen may both lead to damage of tumor cells, viruses and healthy cells. For activation of the body's own immune system, the body must identify a malignant cell or virus as threat and create an immune response capable of lasting cytotoxic effects directed to that threat. In the present invention, different wavelengths of light (for example from different phosphors nearby or within the target cell) activate different biological response. In one embodiment, one wavelength can be used to activate psoralen for its attachment to a cancer cell, while another different wavelength can be used for a different purpose such as for example singlet oxygen generation (i.e., highly reactive oxygen species), excitation of DNA strands of the cancer cell making it more susceptible for psoralen interaction, DNA fragmentation.

In one embodiment, one wavelength can be used to activate psoralen for its attachment to a cancer cell, while another different wavelength can be used to stimulate psoralen such that it reacts with molecular oxygen to produce active oxygen species such as superoxide and singlet oxygen that cause lethal damage.

In various embodiments of this invention, the different wavelengths of the present invention can be used for regulation and control of biological responses having varying degrees of apoptosis (the process of programmed cell death PCD) and necrosis (the premature death of cells and living tissue typically from external factors). In necrosis, factors external to the cell or tissue, such as infection, toxins, or trauma that result in the unregulated digestion of cell components. In contrast, apoptosis is a naturally occurring programmed and targeted cause of cellular death. While apoptosis often provides beneficial effects to the organism, necrosis is almost always detrimental and can be fatal.

Cells that die due to necrosis do not follow the apoptotic signal transduction pathway but rather various receptors are activated that result in the loss of cell membrane integrity and an uncontrolled release of products of cell death into the intracellular space. This initiates in the surrounding tissue an inflammatory response which prevents nearby phagocytes from locating and eliminating the dead cells by phagocytosis. For this reason, it is often necessary to remove necrotic tissue surgically, a procedure known as debridement. Untreated necrosis results in a build-up of decomposing dead tissue and cell debris at or near the site of the cell death. A classic example is gangrene.

In one embodiment of this invention, the different wavelengths address either factors which influence the progression of necrosis or its symptoms. In one embodiment of this invention, the different wavelengths provides for a more "programmed" apoptosis to eliminate unhealthy cells such as cancer. In one embodiment of this invention, the different wavelengths can promote interferon-beta which triggers cells to undergo necrosis, and this mechanism could kill cancer cells Interferons (IFNs) are proteins made and released by host cells in response to the presence of pathogens such as viruses, bacteria, parasites or tumor cells. IFNs allow for communication between cells to trigger the protective defenses of the immune system that eradicate pathogens or tumors. IFNs belong to the large class of glycoproteins known as cytokines. Interferons are named after their ability to "interfere" with viral replication within host cells. IFNs have other functions: they activate immune cells, such as natural killer cells and macrophages; they increase recognition of infection or tumor cells by up-regulating antigen presentation to T lymphocytes;

In general, the different wavelengths provided to the target structure selectively turn on different biological responses. However, the present invention is not so limited and different wavelengths provided to the target structure may have a cumulative (or alternatively a synergistic) effect with regard to one biological response. Moreover, in the present invention, the biological response may be one which suppresses a biological reaction.

In various embodiments, the different biological responses include not only the activation of a drug (e.g., the psoralen activation noted above) but also the redirection of metabolic pathways, up-regulation of certain genes, down-regulation of certain genes, secretion of cytokines, alteration of cytokine receptor responses, or combinations thereof.

In various embodiments, a first biological response caused by light a first wavelength can result in the bonding of a drug or pharmaceutical agent to a critical cellular structure such as nuclear DNA, mRNA, rRNA, ribosome, mitochondrial DNA, or any other functionally important structures. A second biological response caused by light a second wavelength can result in releasing metabolites which can interfere with normal metabolic pathways. A second biological response caused by light a second wavelength can result in altering a targeted cellular response and/or other suitable biochemical or metabolic alterations. Increases in cerebral blood flow accompanied by a significant increase in nitric oxide production have been observed in subjects treated with low levels of 808 nm radiation.

As noted above, Bjordal et al. in "A systematic review of low level laser therapy with location-specific doses for pain from chronic joint disorders," in the Australian journal of physiotherapy 49(2):107-16), the entire contents of this article are incorporated herein by references, describe several NIR treatments for joint disorders. In one embodiment of this invention, one of the different wavelengths provided to the target structure can include those wavelengths described in Bjordal et al. for treatment of joint disorders. In particular, in one embodiment of this invention, one of the different wavelengths provided to the target structure can be at wavelengths of 632 nm, 820 nm, 830, nm, 904 nm, and/or 1060 nm. These wavelengths tend to reduce inflammation. In this embodiment, these wavelengths (or other similar wavelengths) can be used alone or in conjunction with other drugs such as for example anti-inflammatories such as NSAID. In this embodiment, one of the other wavelengths provided to the target structure can be in the ultraviolet range to induce activation of a photoactivatable drug such as psoralen.

Additionally, in one embodiment of this invention, one of the different wavelengths provided to the target structure can be at wavelengths of 620 nm, 680 nm, 760 nm, and 820-830 nm. Other suitable wavelengths (ranges) for photobiomodulation include 1) 613.5-623.5 nm, 2) 667.5-683.7 nm, 3) 750.7-772.3 nm, 4) 812.5-846.0 nm. These wavelengths (and the wavelengths described below) are useful in the present invention as the different wavelengths provided to the target structure to affect photobiomodulation.

For example, light in the far-red to near-IR spectral range (as one of the different wavelengths provided to a target structure) can modulate various biological processes by activation of mitochondrial respiratory chain components, resulting in initiation of a signaling cascade that promotes cellular proliferation and cytoprotection. Cytochrome oxidase is considered to be a key photoacceptor of light in the far-red to near-IR spectral range. Cytochrome oxidase is an integral membrane protein that contains four redox active metal centers and has a strong absorbency in the far-red to near-IR spectral range detectable in vivo by near-IR spectroscopy. Light at 660-680 nm of irradiation (as one of the different wavelengths provided to a target structure) can increase electron transfer in cytochrome oxidase, increase mitochondrial respiration and up-regulate cytochrome oxidase activity in neuronal cells.

Photostimulation can induce a cascade of signaling events initiated by the initial absorption of light by cytochrome oxidase. These signaling events may include the activation of immediate early genes, transcription factors, cytochrome oxidase subunit gene expression, and a host of other enzymes and pathways related to increased oxidative metabolism. Red to near-IR light stimulation (as one of the different wavelengths provided to a target structure) of mitochondrial electron transfer can increase the generation of reactive oxygen species. These mitochondrially generated reactive oxygen species may function as signaling molecules to provide communication between mitochondria and the cysts and nucleus.

Furthermore, in this photobiomodulation embodiment, one of the other wavelengths provided to the target structure can be in the ultraviolet range to induce activation of a photoactivatable drug such as psoralen. In this embodiment, one of the other wavelengths provided to the target structure can be those wavelengths noted above which tend to reduce inflammation.

In another embodiment, one of the different wavelengths provided to the target structure can be in the range of 400 to 700 nm to reduce the degree of neointima formation and the incidence of restenosis (a narrowing of a blood vessel, leading to restricted blood flow) Restenosis is a common adverse event of endovascular procedures such as vascular surgery, cardiac surgery, and angioplasty. Indeed, the phenomenon of vessel restenosis, an immune response to damaged tissue, is known to be a common adverse event and is one of the leading problems with angioplasty and stenting. Accordingly, in this embodiment, light in the range of 400 to 700 nm wavelength range, and more specifically in the 594-600 nm, can be provided as one of the different wavelengths provided to the target structure in vivo to decrease fibrointimal thickening following the arterial injury. Furthermore, in this embodiment, one of the other wavelengths provided to the target structure can be in the ultraviolet range to induce activation of a photoactivatable drug such as psoralen. In this embodiment, one of the other wavelengths provided to the target structure can be those wavelengths noted above which tend to reduce inflammation.

In another embodiment, one of the different wavelengths provided to the target structure can be in the range of red to infrared for modulation of brain cell activity. In this embodiment, one of the different wavelengths provided to the target structure can be between 630 nm and 800 nm or 808 nm, in near-infrared spectrum or other wavelengths particularly suitable for transmission and dispersion within the gray matter and white matter of the brain. It has been shown that, within the visible and near-infrared spectral range, white matter in both the central and peripheral nervous systems reflects most of the incident power and shows a low level of absorption and a short penetration depth. In contrast, the transmittance of the gray matter is approximately twice as high as that of the white matter. While, in the present invention, the initiation energy (e.g., x-ray flux) can readily penetrate into the recessed areas of the brain to generate by way of energy modulation agents (down converters) near infrared light, generation of the near infrared light in these areas and propagation of near infrared light throughout the diseased cells of the brains is considered to be a highly beneficial aspect of this invention. For example, in this embodiment, exposure of the brain cells to these wavelengths in the near infrared can induce whole-brain metabolic and antioxidant beneficial effects such as increases in cytochrome oxidase and superoxide dismutase activities and increases in cerebral blood flow. Additionally, this treatment can include other drugs known to have a beneficial effect on brain disorders. Furthermore, in this embodiment, one of the other wavelengths provided to the target structure can be in the ultraviolet range to induce activation of a photoactivatable drug such as psoralen. In this embodiment, one of the other wavelengths provided to the target structure can be those wavelengths noted above which tend to reduce inflammation. (Although the description above is directed to brain disorders, these treatments according to this invention would be useful of the treatment of other neural conditions throughout the body.)

In another embodiment of this invention, one of the different wavelengths provided to the target structure can be either a yellow or a green light. As noted above, photostimulation can be used to activate a light-sensitive protein such as rhodopsin (ChR2), which can then excite the cell expressing the opsin. It has been shown that channelrhodopsin-2, a monolithic protein containing a light sensor and a cation channel, provides electrical stimulation of appropriate speed and magnitude to activate neuronal spike firing.

Thus, light-sensitive proteins can be introduced into cells or live subjects via a number of techniques including electroporation, DNA microinjection, viral delivery, liposomal transfection and calcium-phosphate precipitation. The gene, chloride pump (NpHR), which is borrowed from a microbe called an archaebacterium, can make neurons less active in the presence of yellow light. By combining genes ChR2 and NpHR, neurons can be made to obey pulses of light like drivers obey a traffic signal: Blue means "go" (emit a signal), and yellow means "stop" (don't emit). Accordingly, a light-sensitive protein (for example, channelrhodopsin-2 (ChR2) and chloride pump halorhodopsin (NpHR)) can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light. Thus, in the present invention, the photoactivation can lead to either suppression or activation of a biological process depending on the gene selected and the wavelength of light chosen. Furthermore, in this embodiment, one of the other wavelengths provided to the target structure can be in the ultraviolet range to induce activation of a photoactivatable drug such as psoralen. In this embodiment, one of the other wavelengths provided to the target structure can be those wavelengths noted above which tend to reduce inflammation.

In another embodiment of this invention, one of the different wavelengths provided to the target structure can be 632 nm light for generation of a light-oxygen effect (LOE), which involves activation of or damage to biosystems by optical radiation at low optical doses by direct photoexcitation of molecular oxygen dissolved in a biosystem so that oxygen dissolved is converted to a singlet state, i.e., by photogeneration of molecular singlet oxygen from O2 dissolved in cells. This process can occur in the presence or absence of a photosensitizer. Furthermore, in this embodiment, one of the other wavelengths provided to the target structure can be in the ultraviolet range to induce activation of a photoactivatable drug such as psoralen. In this embodiment, one of the other wavelengths provided to the target structure can be those wavelengths noted above which tend to reduce inflammation.

In another embodiment of this invention, one of the different wavelengths provided to the target structure can be While denoted above as belonging to either first or second biological responses, the present invention can affect any of the biological responses set forth in this specification as either a first or a second biological response. Furthermore, the sequence of biological responses does not necessarily follow in order. For example, a first biological response could in time actually occur first or second or simultaneously. Likewise, a second biological response could actually occur in time as a first response or a second response or simultaneously with the first biological response.

In one embodiment, the method applies initiation energy from at least one source to the target structure, wherein the initiation energy contacts the target structure, generates at least one or more different wavelengths of light, and induces a predetermined change in the target structure in situ.

In one embodiment, the predetermined change modifies the target structure or modulates the biological activity of the target structure.

In one embodiment, the method contacts the target structure with at least one activatable pharmaceutical agent (PA) that is capable of effecting a predetermined change in the target structure when activated by the one or more different wavelengths of light one of the plurality of light emitters.

In one embodiment, the method applies an initiation energy from at least one source to the target structure in a subject in need of treatment, wherein the initiation energy contacts the target structure and induces a predetermined change in the target structure in situ by way of the selective activation from the plurality of light emitters at different wavelengths. In one embodiment of the method, the predetermined change modifies the target structure and modulates the biological activity of the target structure.

In one embodiment, the method contacts a target structure with at least one activatable pharmaceutical agent (PA) that is capable of effecting a predetermined change in a target structure when activated by one of the plurality of light emitters, optionally in the presence of at least one member selected from the group consisting of energy modulation agents, plasmonics-active agents and combinations thereof.

In one embodiment, the energy modulation agent, if present, upgrades or downgrades the initiation energy to produce one or more of the different wavelengths of light. In one embodiment, the plasmonics-active agent, if present, enhances or modifies the light generated internally or provided internally within the subject or applied initiation energy or both.

A further object of the present invention is to provide such methods which can use any suitable energy source as the initiation energy source in combination with plasmonics materials to activate the activatable pharmaceutical agent and thereby cause the predetermined change.

A further object of the present invention is to provide such methods using plasmonics in an energy cascade to activate an activatable pharmaceutical agent that then cause the predetermined change.

A further object of the present invention is to provide such methods for in situ generation of energy which causes, either directly or indirectly, the predetermined change.

A further object of the present invention is to provide a method for the treatment of a cell proliferation disorder that permits treatment of a subject in any area of the body while being non-invasive and having high selectivity for targeted cells relative to healthy cells through the use of exciton-plasmon enhancement.

A further object of the present invention is to provide a method for treatment of a condition, disorder or disease which can use any suitable energy source as the initiation energy source in combination with plasmon enhancement to activate the activatable pharmaceutical agent.

A further object of the present invention is to provide a method for treatment of a condition, disorder or disease using plasmon enhancement in an energy cascade to activate an activatable pharmaceutical agent that then treats cells suffering from a condition, disorder or disease.

The condition, disorder, or disease may be mediated by abnormal cellular proliferation and the predetermined change in one embodiment can ameliorate the abnormal cellular proliferation. Abnormal cellular proliferation may be higher than that of cells from a subject not having said condition, disorder or disease or may be lower.

The treated condition, disorder, or disease may or may not be significantly mediated by abnormal cellular proliferation, and the predetermined change does not have to substantially affect cellular proliferation.

The target structure need not be present inside an organism, but may be one in vitro or ex vivo. The predetermined change may enhance the expression of, promote the growth of, or increase the quantity of the target structure; or the predetermined change can enhance, inhibit or stabilize the usual biological activity of the target structure compared to a similar untreated target structure. For example, the predetermined change can alter the immunological or chemical properties of the target structure which may be a cell, cell membrane, internal cellular structure, polypeptide or non-polypeptide compound which can be modified by said predetermined change to be more or less antigenic or immunogenic. In another embodiment, modifying the target structure can be done without the need for a pharmaceutical agent, or a plasmonics agent.

One object of the present invention is to modify a target structure which mediates or is associated with a biological activity, and in a preferred embodiment to treat a condition, disorder or disease, in a subject using photobiomodulation by way of the selective activation noted above.

Exemplary conditions, disorders or diseases may include, but are not limited to, cancer, autoimmune diseases, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Other exemplary conditions, disorders or diseases may include, but are not limited to cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthrisis, joint conditions, lymph node conditions, and cognitive and behavioral conditions.

In one embodiment, a method in accordance with the present invention utilizes the principle of energy transfer to and among molecular agents to control delivery and activation of cellular changes by irradiation such that delivery of the desired effect is more intensified, precise, and effective than the conventional techniques. At least one energy modulation agent can be administered to the subject which adsorbs, intensifies or modifies said initiation energy into an energy that effects a predetermined cellular change in said target structure. The energy modulation agent may be located around, on, or in said target structure. Further, the energy modulation agent can transform a photonic initiation energy into a photonic energy that effects a predetermined change in said target structure. In one embodiment, the energy modulation agent decreases the wavelength of the photonic initiation energy (down convert). In another embodiment, the energy modulation agent can increase the wavelength of the photonic initiation energy (up convert). In a different embodiment the modulation agent is one or more members selected from a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

In one aspect of the invention, a downconverting energy modulation agent can comprise inorganic particulates selected from the group consisting of: metal oxides; metal sulfides; doped metal oxides; and mixed metal chalcogenides. In one aspect of the invention, the downconverting material can comprise at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS and alkali lead silicate including compositions of $SiO_2$, $B_2O_3$, $Na_2O$, $K_2O$, PbO, MgO, or Ag, and combinations or alloys or layers thereof. In one aspect of the invention, the downconverting material can include a dopant including at least one of Er, Eu, Yb, Tm, Nd, Mn Tb, Ce, Y, U, Pr, La, Gd and other rare-earth species or a combination thereof. The dopant can be included at a concentration of 0.01%-50% by mol concentration.

In one aspect of the invention, the downconverting energy modulation agent can comprise materials such as ZnSeS:Cu, Ag, Ce, Tb; CaS: Ce,Sm; $La_2O_2S$:Tb; $Y_2O_2S$:Tb; $Gd_2O_2S$: Pr, Ce, F; $LaPO_4$. In other aspects of the invention, the downconverting material can comprise phosphors such as ZnS:Ag and ZnS:Cu, Pb. In other aspects of the invention, the downconverting material can be alloys of the ZnSeS family doped with other metals. For example, suitable materials include $ZnSe_xS_y$:Cu, Ag, Ce, Tb, where the following x, y values and intermediate values are acceptable: x:y; respectively 0:1; 0.1:0.9; 0.2:0.8; 0.3:0.7; 0.4:0.6; 0.5: 0.5;

0.6:0.4; 0.7:0.3; 0.8:0.2; 0.9:0.1; and 1.0:0.0.

In other aspects of the invention, the downconverting energy modulation agent can be materials such as sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3$Tb), gadolinium oxysulphide:europium ($Gd_2O_2S$:Eu), lanthanum oxysulphide:europium ($La_2O_2S$: Eu), and gadolinium oxysulphide:promethium, cerium, fluorine ($Gd_2O_2S$:Pr,Ce,F), $YPO_4$:Nd, $LaPO_4$:Pr, $(Ca,Mg)SO_4$: Pb, $YBO_3$:Pr, $Y_2SiO_5$:Pr, $Y_2Si_2O_7$:Pr, $SrLi_2SiO_4$:Pr,Na, and $CaLi_2SiO_4$:Pr.

In other aspects of the invention, the downconverting energy modulation agent can be near-infrared (NIR) downconversion (DC) phosphors such as $KSrPO_4$:$Eu^{2+}$, $Pr^{3+}$, or $NaGdF_4$:Eu or $Zn_2SiO_4$:$Tb^{3+}$,$Yb^{3+}$ or β-$NaGdF_4$ co-doped with $Ce^{3+}$ and $Tb^{3+}$ ions or $Gd_2O_2S$:Tm or $BaYF_5$:$Eu^{3+}$ or other down converters which emit NIR from visible or UV light exposure (as in a cascade from x-ray to UV to NIR) or which emit NIR directly after x-ray or e-beam exposure.

In one aspect of the invention, a up converting energy modulation agent can be at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

In one aspect of the invention, the energy modulation agents can be used singly or in combination with other down converting or up converting materials.

In one embodiment, the initiation energy can be provided by way of catheters inserted into the subject. The catheters can include prescribed energy modulation agents (e.g., up converting or down converting materials noted herein) at a distal end of the catheter which emit the aforementioned light for selective activation into the subject.

Below is a list of X-ray phosphors which can be used in the present invention along with their corresponding peak emission values.

TABLE 1

| # | Phosphor | Emission Spectrum Peak Emission (nm) | X-ray Absorption Emiss Eff (%) | X-ray Absorption Eff (Z) | X-ray Absorption K-edge (keV) | Microstructure Specific Gravity | Microstructure Crystal Structure | Hygroscopic |
|---|---|---|---|---|---|---|---|---|
| 1 | BaFCl:Eu$^{2+}$ | 380 | 13 | 49.3 | 37.38 | 4.7 | Tetragonal | N |
| 2 | BaSO$_4$–:Eu$^{2+}$ | 390 | 6 | 45.5 | 37.38 | 4.5 | Rhombic | N |
| 3 | LaOBr:Tm$^{3+}$ | 360, 460 | 14 | 49.3 | 38.92 | 6.3 | Tetragonal | N |
| 4 | YTaO$_4$ | 337 | | 59.8 | 67.42 | 7.5 | Monolithic | N |
| 5 | YTaO$_4$:Nb (*) | 410 | 11 | 59.8 | 67.42 | 7.5 | Monolithic | N |
| 6 | CaWO$_4$ | 420 | 5 | 61.8 | 69.48 | 6.1 | Tetragonal | N |
| 7 | LaOBr:Tb$^{3+}$ | 420 | 20 | 49.3 | 38.92 | 6.3 | Tetragonal | N |
| 8 | Y$_2$O$_2$S:Tb$^{3+}$ | 420 | 18 | 34.9 | 17.04 | 4.9 | Hexgonal | N |
| 9 | ZnS:Ag | 450 | 17 | 26.7 | 9.66 | 3.9 | Hexgonal | N |
| 10 | (Zn,Cd)S:Ag | 530 | 19 | 38.4 | 9.66/26.7 | 4.8 | Hexgonal | N |
| 11 | Gd$_2$O$_2$S:Tb$^{3+}$ | 545 | 13 | 59.5 | 50.22 | 7.3 | Hexgonal | N |
| 12 | La$_2$O$_2$S:Tb$^{3+}$ | 545 | 12.5 | 52.6 | 38.92 | 6.5 | Hexgonal | N |

Various plastic scintillators, plastic scintillator fibers and related materials are made of polyvinyltoluene or styrene and fluors. These materials could be used in the present invention especially if encapsulated or otherwise chemically isolated from the target structure so not as to be dissolved or otherwise deteriorated by the fluids of the target structure. These and other formulations are commercially available, such as from Saint Gobain Crystals, as BC-414, BC-420, BC-422, or BCF-10.

TABLE 2

| Phosphor | Product Reference | Peak Emission (nm) |
|---|---|---|
| Organic | BC-414 | 392 |
| Organic | BC-420 | 391 |
| Organic | BC-422 | 370 |

Other polymers are able to emit in the visible range and these include:

TABLE 3

| Phosphor (Fiber Forms) | Product Reference | Peak Emission (nm) | # of Photons Per MeV |
|---|---|---|---|
| Organic | BCF-10 | 432 | 8000 |
| Organic | BC-420 | 435 | 8000 |
| Organic | BC-422 | 492 | 8000 |

Table 4 shows a wide variety of energy modulation agents which can be used in this invention.

TABLE 4

| Phosphor Color | Emission Spectrum Peak Emmission (nm) | Emiss Eff (%) | Eff (Z) | X-Ray Absoprtion K-edge (keV) | Specific Gravity | Crystal Structure | Hygroscopic |
|---|---|---|---|---|---|---|---|
| Zn3(PO4)2: Tl+ | 310 | | | | | | N |
| BaF2 | 310 | | | | | | Slightly |
| CsI | 315 | | | | | | N |
| Ca3(PO4)2: Tl+ | 330 | | | | | | N |
| YTaO4 | 337 | | 59.8 | 67.42 | 7.5 | Monolithic | N |
| CsI: Na | 338 | | | | | | Y |
| BaSi2O5: Pb2+ | 350 | | | | | | N |
| Borosilicate | 350 | | | | | | N |
| LaCl3(Ce) | 350 | | | | | | Y |
| SrB4O7F: Eu2+ | 360 | | | | | | N |
| RbBr: Tl+ | 360 | | | | | | ? |
| (Ba, Sr, Mg)3Si2O7: Pb2+ | 370 | | | | | | N |
| YAlO3: Ce3+ | 370 | | | | | | N |
| BC-422 | 370 | | | | | Organic | ? |
| BaFCl: Eu2+ | 380 | 13 | 49.3 | 37.38 | 4.7 | Tetragonal | N |
| BaSO4—: Eu2+ | 390 | 6 | 45.5 | 37.38 | 4.5 | Rhombic | N |
| BaFBr: Eu2+ | 390 | | | | | | ? |
| BC-420 | 391 | | | | | Organic | ? |
| BC-414 | 392 | | | | | Organic | ? |
| SrMgP2O7: Eu2+ | 394 | | | | | | N |
| BaBr2: Eu2+ | 400 | | | | | | N |
| (Sr, Ba)Al2Si2O8: Eu2+ | 400 | | | | | | N |
| YTaO4: Nb (*) | 410 | 11 | 59.8 | 67.42 | 7.5 | Monolithic | N |
| Y2SiO5: Ce3+ | 410 | | | | | | N |
| CaWO4 | 420 | 5 | 61.8 | 69.48 | 6.1 | Tetragonal | N |
| LaOBr: Tb3+ | 420 | 20 | 49.3 | 38.92 | 6.3 | Tetragonal | N |
| Y2O2S: Tb3+ | 420 | 18 | 34.9 | 17.04 | 4.9 | Hexgonal | N |

TABLE 4-continued

| Phosphor Color | Emission Spectrum Peak Emmission (nm) | Emiss Eff (%) | Eff (Z) | X-Ray Absoprtion K-edge (keV) | Specific Gravity | Crystal Structure | Hygroscopic |
|---|---|---|---|---|---|---|---|
| Lu2SiO5: Ce3+ | 420 | | | | | | N |
| Lu1.8 Y0.2SiO5: Ce | 420 | | | | | | N |
| ZnS: Ag | 450 | 17 | 26.7 | 9.66 | 3.9 | Hexgonal | N |
| CdWO4 | 475 | | | | | | Slightly |
| Bi4Ge3O12 (BGO) | 480 | | | | | | N |
| (Zn, Cd)S: Ag | 530 | 19 | 38.4 | 9.66/26.7 | 4.8 | Hexgonal | N |
| Gd2O2S: Tb3+ | 545 | 13 | 59.5 | 50.22 | 7.3 | Hexgonal | N |
| La2O2S: Tb3+ | 545 | 12.5 | 52.6 | 38.92 | 6.5 | Hexgonal | N |
| Y3Al5O12 (Ce) | 550 | | | | | | N |
| LaOBr: Tm3+ | 360,460 | 14 | 49.3 | 38.92 | 6.3 | Tetragonal | N |
| CaF2(Eu) | 435/300 | | | | | | N |

By selection of one or more of the phosphors noted above (or others known in the art), the present invention permits one to provide in a vicinity of or within a target structure one or more light emitters capable of emitting different wavelengths corresponding to respective biological responses, and permits the activation of one or more biological responses in the target structure depending on at least one or more different wavelengths of light generated internally or provided internally within the subject, wherein the different wavelengths activate the respective biological responses (i.e., selective activation).

In one embodiment, the present invention provides methods utilizing the principle of energy transfer to and among molecular agents to control delivery and activation of pharmaceutically active agents such that delivery of the desired pharmacological effect is focused and precise.

In one embodiment, the initiation energy source is applied directly or indirectly (via a modulation agent) to the activatable pharmaceutical agent, preferably in proximity to the target cells.

Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the modulation agent and/or activatable pharmaceutical agent within a subject. In one embodiment, the initiation energy interacts with a previously administered energy modulation agent which then activates the predetermined cellular changes. In another embodiment, the initiation energy interacts with a previously administered energy modulation agent which then activates the activatable pharmaceutical agent. In another embodiment, the initiation energy itself activates the activatable pharmaceutical agent. In either embodiment, the initiation energy source cannot be within line-of-sight of the modulation agent and/or the activatable pharmaceutical agent. By "cannot be within line-of-sight" is meant that if a hypothetical observer were located at the location of the modulation agent or the activatable pharmaceutical agent, that observer would be unable to see the source of the initiation energy.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthritis, joint conditions, and lymph node conditions.

As used herein, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent (or agents) may be preferably directed to the desired site (e.g. a tumor) by systemic administration to a subject. For example, a UV-A emitting energy modulation agent (or agents) may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

In one embodiment, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Exemplary energy modulation agents may include, but are not limited to, at least one energy modulation agent selected from the group consisting of a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

As used herein, an "activatable pharmaceutical agent" is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof.

Activation of the agent (or agents) may be as simple as delivering the signal to the agent or may further premise on a set of activation conditions. For example, in the former case, an activatable pharmaceutical agent, such as a photosensitizer, may be activated by UV-A radiation. Once activated, the agent (or agents) in its (their) active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment of the present invention can be by the methods described in U.S. application Ser. No. 11/935,655, filed Nov. 6, 2007 (incorporated by reference above), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent (or agents), which had received energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 5 lists some photoactivatable molecules capable of being photoactivated to induce an auto vaccine effect.

Table 6 lists some additional endogenous photoactivatable molecules.

TABLE 6

| Endogenous Fluorophores | Excitation Max. (nm) | Emission Max. (nm) |
| --- | --- | --- |
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucelotide | 290, 351 | 440, 400 |
| reduced nicotinamide dinucelotide phosphate | 336 | 464 |
| Vitamins | | |
| Vitamins A | 327 | 510 |
| Vitamins K | 335 | 480 |
| Vitamins D | 390 | 480 |
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrine | 400-450 | 630, 690 |

FIG. 1 provides an exemplary electromagnetic spectrum in meters (1 nm equals meters).

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

TABLE 5

| Compound | $A_{ex}$ (nm) | $E_{SSET}$ | $k_s$ of donor ($s^{-1}$) | $k_{SSET}$ ($s^{-1}$) | $k_{SSET}$ ($s^{-1}$) (Average) | $R_0$ (A) | $R$ (A) | $R_{model}$(A) (Average) | $E_{TTET}$ | $k_{TTET}$ ($s^{-1}$) |
| --- | --- | --- | --- | --- | --- | --- | --- | --- | --- | --- |
| 1B | 224 | 96.3 | $9.5 \times 10^5$ | $2.44 \times 10^8$ | $1.87 \times 10^3$ | 14.7 | 9 | 9.5 | | |
| | 266 | 95 | | $1.8 \times 10^8$ | | | | | 2.5 | $5 \times 10^2$ |
| | 280 | 94 | | $1.36 \times 10^8$ | | | | | | |
| 1A | 224 | 80 | $9.5 \times 10^5$ | $3.8 \times 10^7$ | $3.67 \times 10^7$ | 14.7 | 11.8 | 14.1 | | |
| | 266 | 79 | | $3.6 \times 10^7$ | | | | | 2 | $3.6 \times 10^2$ |
| | 280 | 79 | | $3.6 \times 10^7$ | | | | | | |
| 2B | 224 | 77 | $9.5 \times 10^5$ | $3.1 \times 10^7$ | $3.9 \times 10^7$ | 14.7 | 11.9 | 6.5 | | |
| | 266 | 81 | | $3.9 \times 10^7$ | | | | | 32 | $9.4 \times 10^3$ |
| | 280 | 83 | | $4.7 \times 10^7$ | | | | | | |
| 2A | 224 | 69 | $9.5 \times 10^5$ | $2.1 \times 10^7$ | $3 \times 10^7$ | 14.7 | 12.2 | 8.1 | | |
| | 266 | 80 | | $3.7 \times 10^7$ | | | | | 74.3 | $5.7 \times 10^4$ |
| | 280 | 77 | | $3.2 \times 10^7$ | | | | | | |

The initiation energy source can be any energy source capable of providing energy at a level sufficient to cause cellular changes directly or via a modulation agent which transfer the initiation energy to energy capable of causing the predetermined cellular changes. Also, the initiation energy source can be any energy source capable of providing energy at a level sufficient activate the activatable agent directly, or to provide the energy to a modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams.

In a preferred embodiment the initiation energy is capable of penetrating completely through the subject. Within the context of the present invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, UV light, visible light, IR radiation, x-rays, gamma rays, electron beams, microwaves and radio waves. In one embodiment, the initiation energy can penetrate completely through the subject and can be applied from a single source or more than one source.

In another embodiment, the initiation energy source 1 may be a linear accelerator equipped with image guided computer-control capability to deliver a precisely calibrated beam of radiation to a pre-selected coordinate. One example of such is the SmartBeam™ IMRT (intensity modulated radiation therapy) method from Varian medical methods (Varian Medical Methods, Inc., Palo Alto, Calif.). X-ray machines that produce from 10 to 150 keV X-rays are readily available in the marketplace. For instance, the General Electric Definium series or the Siemens MULTIX series are but two examples of typical X-ray machines designed for the medical industry, which could be used in the present invention.

In one embodiment, the initiation energy may also be UV radiation, visible light, infrared radiation (IR), x-rays, gamma rays, an electron beam, microwaves or radio waves. Energy modulation agents (e.g., up converting or down converting agents) inside the subject emit the aforementioned light for selective activation into the subject.

An additional embodiment of the present invention is to provide a method for treatment of a condition, disease or disorder by the in-situ generation of energy in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to conversion of an energy applied to the subject externally, which is converted in-situ to a different energy (of lower or higher energy than that applied), through the use of one or more energy modulation agents producing at least two different wavelengths of light, each wavelength of light associated with a different biological response. For example, light of first wavelength photactivates a pharmaceutical agent, and light of second wavelength heats the local treatment area.

A further embodiment of the present invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying an initiation energy which, directly or indirectly, activates the pharmaceutical agent or agents by way of exposure of the pharmaceutical agent or agents to at least two different wavelengths of light, each wavelength of light associated with a different biological response. For example, light of first wavelength photactivates a psoralen or derivative thereof, and light of second wavelength heats the local treatment area.

As noted elsewhere in the present application, this initiation energy can be of any type, so long as it can be converted to an energy suitable for activating the pharmaceutical compound. In addition to applying this initiation energy, in this embodiment of the present invention, an energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the present invention methods to enhance the onset of apoptosis.

Additional sources of heat can be utilized. Heat can be generated using the application of microwaves or NIR energy to the target structure or by the use of use of nanoparticles of metal or having metal shells. In the nanoparticles embodiment, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Natarajan A et al.: Thermal dosimetry predictive of efficacy of 111In-ChL6 NPAMF-induced thermoablative therapy for human breast cancer in mice. J. Nucl. Med. 48(3), 437-444 (2007).)

Alternatively, one can generate heat through the application of NIR to nanoparticles having metal shells which is converted into thermal energy. (Hirsch L R, Stafford R J, Bankson J et al.: Nanoshell-mediated near-infrared thermal therapy of tumors under magnetic resonance guidance. Proc. Natl Acad. Sci. USA 100(23), 13549-13554 (2003)).

Photoactivatable agents may be in general stimulated by an energy source, such as UV or visible or infrared irradiation from the energy modulation agents at different wavelengths, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis.

One preferred method of treating a condition, disorder or disease mediated by a target structure in a subject comprises:

(1) administering to the subject at least one activatable pharmaceutical agent that is capable of effecting a predetermined change to the target structure when activated; and
(2) applying an initiation energy from an initiation energy source to the subject,
wherein the applied initiation energy activates the activatable agent in situ by different wavelengths of UV or visible or infrared irradiation emitted from at least one energy modulation agent in a vicinity of or within the target structure,
thus causing the predetermined change to the target structure to occur, wherein said predetermined change treats the condition, disorder, or disease.

Another preferred method for treating a condition, disorder or disease mediated by a target structure in a subject, comprises:
(1) administering to the subject at least one activatable pharmaceutical agent that is capable of activation by a multi photon absorption event and of effecting a predetermined change in said target when activated by different wavelengths of UV or visible or infrared irradiation emitted from at least one energy modulation agent in a vicinity of or within the target structure; and
(2) applying an initiation energy from an initiation energy source to the subject,
wherein the applied initiation energy activates the activatable agent by the multi photon absorption event in situ,
thus causing the predetermined change to occur, wherein said predetermined change treats the condition, disorder, or disease.

The concept of multi-photon excitation is based on the idea that two or more photons of low energy can excite a fluorophore in a quantum event, resulting in the emission of a fluorescence photon, typically at a higher energy than the two or more excitatory photons.

Commonly used fluorophores have excitation spectra in the 400-500 nm range, whereas the laser used to excite the fluorophores lies in the ~700-1000 nm (infrared) range. If the fluorophore absorbs two infrared photons simultaneously, it will absorb enough energy to be raised into the excited state. The fluorophore will then emit a single photon with a wavelength that depends on the type of fluorophore used (typically in the visible spectrum). Because two photons need to be absorbed to excite a fluorophore, the probability of emission is related to the intensity squared of the excitation beam. Therefore, a higher amount of two-photon fluorescence is generated where the laser beam is tightly focused than where it is more diffuse. Effectively, fluorescence is observed in any appreciable amount in the focal volume, resulting in a high degree of rejection of out-of-focus objects.

Accordingly, another method for treating a condition, disease, or disorder mediated by a target structure in a subject, comprises:
(1) administering to the subject at least one energy modulation agent and at least one activatable pharmaceutical agent that is capable of activation by multi photon absorption and of effecting a predetermined cellular change when activated by different wavelengths of UV or visible or infrared irradiation emitted from the at least one energy modulation agent in a vicinity of or within the target structure; and
(2) applying an initiation energy from an initiation energy source to the subject,
wherein the energy modulation agent upgrades the applied initiation energy to an energy, which then activates the activatable agent by a multi photon absorption event in situ,
thus causing the predetermined cellular change to occur, wherein said predetermined cellular change treats the condition, disease or disorder.

In one embodiment, the energy upgrades are obtained via 2, 3, 4, or 5 simultaneous photon absorptions.

Yet another preferred method for treating a condition, diseases, or disorder mediated by a target structure in a subject, comprises:
(1) administering to the subject at least one energy modulation agent and at least one activatable pharmaceutical agent that is capable effecting a predetermined cellular change when activated by different wavelengths of UV or visible or infrared irradiation emitted from the at least one energy modulation agent in a vicinity of or within the target structure; and
(2) applying an initiation energy from an initiation energy source to the subject,
wherein the energy modulation agent upgrades the applied initiation energy to an energy, which then activates the activatable agent in situ,
thus causing the predetermined cellular change to occur, wherein said predetermined cellular change treats the condition, disease or disorder.

In yet another aspect, the radiative energy may be of a higher energy than the excitation energy of the photoactive agent. In this aspect, the photoactive agent may be activated via an "energy downgrade" mechanism. In one scenario, via the multi-photon mechanism, two lower energy photons having energy x may be absorbed by an agent to excite the agent from ground state E0 to a higher energy state E2. The agent may then relax down to an intermediate energy state E1 by emitting a photon having an energy y that is equal to the energy gap between E2 and E1, where y is less than x. Other mechanisms of energy downgrade may be mediated by energy transformation agents such as quantum dots, nanotubes, or other agents having suitable photo-radiation properties. Thus, yet another preferred method for treating a condition, disease, or disorder mediated by a target structure in a subject, comprises:
(1) administering to the subject at least one energy modulation agent and at least one activatable pharmaceutical agent that is capable of activation by multi photon absorption and of effecting a predetermined cellular change when activated by different wavelengths of UV or visible or infrared irradiation emitted from the at least one energy modulation agent in a vicinity of or within the target structure; and
(2) applying an initiation energy from an initiation energy source to the subject,
wherein the energy modulation agent downgrades the applied initiation energy to an energy, which then activates the activatable agent by a multi photon absorption event in situ,
thus causing the predetermined cellular change to occur, wherein said predetermined cellular change treats the condition, disease, or disorder.

Thus, yet another preferred method for treating a condition, disease, or disorder mediated by a target structure in a subject, comprises:
(1) administering to the subject at least one energy modulation agent and at least one activatable pharmaceutical agent that is capable of effecting a predetermined cellular change when activated by different wavelengths of UV or visible or infrared irradiation emitted from the at least one energy modulation agent in a vicinity of or within the target structure; and (2) applying an initiation energy from an initiation energy source to the subject, wherein the energy modulation agent downgrades the applied initiation energy to an energy, which then activates the activatable agent in situ, thus causing the predetermined cellular change to occur, wherein said predetermined cellular change treats the condition, disorder or disease.

In a further preferred embodiment, the present invention provides a method for treating a condition, disorder or disease mediated by a target structure in a subject, comprising:

(1) administering to the subject an activatable pharmaceutical agent that is capable of effecting a predetermined change in said target structure when activated by different wavelengths of UV or visible or infrared irradiation emitted from at least one energy modulation agent in a vicinity of or within the target structure; and (2) applying an initiation energy from an initiation energy source to the subject, wherein the initiation energy applied and activatable pharmaceutical agent upon activation produce insufficient singlet oxygen in the subject to produce cell lysis, and wherein the initiation energy activates the activatable pharmaceutical agent in situ, thus causing the predetermined change to occur via said target structure, wherein said predetermined change targets the condition, disorder or disease.

In a further preferred embodiment, the present invention provides a method for treating a condition, disorder or disease mediated by a target structure in a subject, comprising:

(1) administering to the subject an activatable pharmaceutical agent that is capable of effecting a predetermined change in said target structure when activated by different wavelengths of UV or visible or infrared irradiation emitted from at least one energy modulation agent in a vicinity of or within the target structure; and (2) applying an initiation energy from an initiation energy source to the subject, wherein the initiation energy applied and activatable pharmaceutical agent upon activation produce a controlled amount of singlet oxygen in the subject to produce cell lysis, and wherein the initiation energy activates the activatable pharmaceutical agent in situ, thus causing the predetermined change to occur via said target structure, wherein said predetermined change targets the condition, disorder or disease.

In a different preferred embodiment, the present invention provides a method for treating a condition, disorder or disease mediated by a target structure in a subject, comprising:

(1) administering to the subject an activatable pharmaceutical agent that is capable of activation by multi photon absorption and effecting a predetermined change in said target structure when activated by different wavelengths of UV or visible or infrared irradiation emitted from at least one energy modulation agent in a vicinity of or within the target structure; and (2) applying an initiation energy from an initiation energy source to the subject, wherein the initiation energy applied and activatable pharmaceutical agent upon activation produce insufficient singlet oxygen in the subject to produce cell lysis, and wherein the initiation energy activates the activatable pharmaceutical agent by the multi photon absorption event in situ, thus causing the predetermined change to occur via said target structure, wherein said predetermined change targets the condition, disorder or disease.

In a different preferred embodiment, the present invention provides a method for treating a condition, disorder or disease mediated by a target structure in a subject, comprising:

(1) administering to the subject an activatable pharmaceutical agent that is capable of activation by multi photon absorption and effecting a predetermined change in said target structure when activated by different wavelengths of UV or visible or infrared irradiation emitted from at least one energy modulation agent in a vicinity of or within the target structure; and (2) applying an initiation energy from an initiation energy source to the subject, wherein the initiation energy applied and activatable pharmaceutical agent upon activation produce a controlled amount of singlet oxygen in the subject to produce cell lysis, and wherein the initiation energy activates the activatable pharmaceutical agent by the multi photon absorption event in situ, thus causing the predetermined change to occur via said target structure, wherein said predetermined change targets the condition, disorder or disease.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. In one embodiment, it is preferable to avoid production of an amount of singlet oxygen that would cause cell lysis, due to its indiscriminate nature of attack, lysing both target cells and healthy cells. Accordingly, in one embodiment, the level of singlet oxygen production caused by the initiation energy used or activatable pharmaceutical agent upon activation is less than level needed to cause cell lysis.

One advantage is that multiple wavelengths of emitted radiation may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, e.g., apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

In a different embodiment, it is preferable to control the amount of singlet oxygen that would cause cell lysis relative to the amount of activated psoralen produced.

Accordingly, in this embodiment, the level of singlet oxygen production caused by the initiation energy used or activatable pharmaceutical agent upon activation is less than or equal to the amount of activated psoralen. For example, the amount of singlet oxygen produced can range from 1% to 95% of the activated psorlen produced. In another example, the amount of singlet oxygen produced can range from 10% to 90% of the activated psoralen produced. In another example, the amount of singlet oxygen produced can range from 20% to 80% of the activated psorlen produced. In another example, the amount of singlet oxygen produced can range from 30% to 70% of the activated psoralen produced. In another example, the amount of singlet oxygen produced can range from 40% to 60% of the activated psorlen produced.

In a different embodiment, it is preferable to control the amount of singlet oxygen to be more than or equal to the amount of activated psoralen. For example, the amount of activated psorlen produced can range from 1% to 95% of the singlet oxygen produced. In another example, the amount of activated psoralen produced can range from 10% to 90% of the singlet oxygen produced. In another example, the amount of activated psorlen produced can range from 20% to 80% of the singlet oxygen produced. In another example, the amount of activated psoralen produced can range from 30% to 70% of the singlet oxygen produced. In another example, the amount of activated psoralen produced can range from 40% to 60% of the singlet oxygen produced.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Yet another example is that nanoparticles or nanoclusters of certain atoms may be introduced such that are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a cell are capable of stimulating activation of photoactivatable agents disposed in a distant portion of the cell, so long as the distance does not greatly exceed $R_0$. For example, gold nanospheres having a size of 5 atoms of gold have been shown to have an emission band in the ultraviolet range, recently.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Any of the photoactivatable agents may be exposed to an excitation energy source implanted in a subject preferably near a target site. The photoactive agent may be directed to a receptor site by a carrier having a strong affinity for the receptor site. Within the context of the present invention, a "strong affinity" is preferably an affinity having an equilibrium dissociation constant, $K_j$, at least in the nanomolar, nM, range or higher. Preferably, the carrier may be a polypeptide and may form a covalent bond with a photoactive agent, for example. The polypeptide may be an insulin, interleukin, thymopoietin or transferrin, for example. Alternatively, a photoactive agent may have a strong affinity for the target cell without binding to a carrier.

A receptor site may be any of the following: nucleic acids of nucleated blood cells, molecule receptor sites of nucleated blood cells, the antigenic sites on nucleated blood cells, epitopes, or other sites where photoactive agents are capable of destroying a targeted cell.

In one embodiment, thin fiber optic lines are inserted in the subject and external light is used to photoactivate the agents. In another embodiment, a plurality of sources for supplying electromagnetic radiation energy or energy transfer can be used.

The phenomenon of ultra weak emission from cellular systems has been a topic of various inquiries since the 1900s. This topic can be traced back to the early investigations of the Russian biologist Gurwitsch Alexander G. Gurwitsch more than seventy years ago, who speculated that ultraweak photon emission transmit information in cells [A. G. Gurwitsch, S. S. Grabje, and S. Salkind, "Die Natur des spezifischen Erregers der Zellteilung," *Arch. Entwicklungsmech. Org.* 100, 11-40, 1923].

In the 1970s, this area of research was investigated by a number of investigators. The presence of biological radiation from a variety of cells was later investigated by several research groups in Europe and Japan using low-noise, sensitive photon-counting detection systems [B. Ruth and F.-A. Popp, "Experimentelle Untersuchungen zur ultraschwachen Photonenemission biologischer Systeme," *Z. Naturforsch., A: Phys. Sci.* 31c, 741-745, 1976; T. I. Quickenden and S. S. Que-Hee, "The spectral distribution of the luminescence emitted during growth of the yeast *Saccharomyces cerevisiae* and its relationship to mitogenetic radiation," *Photochem. Photobiol.* 23, 201-204, 1976; H. Inaba, Y. Shimizu, Y. Tsuji, and A. Yamagishi, "Photon counting spectral analysing system of extra-weak chemi- and bioluminescence for biochemical applications," *Photochem. Photobiol.* 30, 169-175, 1979]. Popp and coworkers suggested the evidence of some 'informational character' associated with the ultra-weak photon emission from biological systems, often referred by Popp as "bio-photons". Other studies reported ultra-weak photon emission from various species including plant, and animals cells [H. J. Niggli, C. Scaletta, Y. Yan, F.-A. Popp, and L. A. Applegate, "Ultraweak photon emission in assessing bone growth factor efficiency using fibroblastic differentiation," *J. Photochem. Photobiol., B*, 64, 62-68, 2001;]. Results of experiments of UV-irradiated skin fibroblasts indicated that repair deficient xeroderma pigmentosum cells show an efficient increase of ultraweak photon emission in contrast to normal cells. [H. J. Niggli, "Artificial sunlight irradiation induces ultraweak photon emission in human skin fibroblasts," *J. Photochem. Photobiol., B* 18, 281-285 (1993)].

A delayed luminescence emission was also observed in biological systems [F.-A. Popp and Y. Yan, "Delayed luminescence of biological systems in terms of coherent states," *Phys. Lett. A* 293, 93-97 (2002); A. Scordino, A. Triglia, F. Musumeci, F. Grasso, and Z. Rajfur, "Influence of the presence of Atrazine in water on in-vivo delayed luminescence of acetabularium acetabulum," *J. Photochem. Photobiol., B*, 32, 11-17 (1996); This delayed luminescence was used in quality control of vegetable products [A. Triglia, G. La Malfa, F. Musumeci, C. *Leonardi*, and A. Scordino, "Delayed luminescence as an indicator of tomato fruit quality," *J. Food. Sci.* 63, 512-515 (1998)] or for assessing the quality or quality changes of biological tissues [Yu Yan, Fritz-Albert Popp*, Sibylle Sigrist, Daniel Schlesinger, Andreas Dolf, Zhongchen Yan, Sophie Cohen, Amodsen Chotia, "Further analysis of delayed luminescence of plants", *Journal of Photochemistry and Photobiology B: Biology* 78, 235-244 (2005)].

It has been reported that UV excitation can further enhance the ultra-weak emission and a method for detecting UV-A-laser-induced ultra-weak photon emission was used to evaluate differences between cancer and normal cells. [H. J. Niggli et al, Laser-ultraviolet-A-induced ultraweak photon emission in mammalian cells, *Journal of Biomedical Optics* 10(2), 024006 (2005)].

Accordingly, in one embodiment of the present invention, upon applying an initiation energy from at least one source to a target structure in a subject in need of treatment, the initiation energy contacts the target structure and induces a predetermined change in said target structure in situ by exposure of the target structure to different wavelengths of UV or visible or infrared irradiation emitted from at least one energy modulation agent in a vicinity of or within the target structure, wherein the predetermined change is the enhancement of energy emission from the target, which then mediates, initiates or enhances a biological activity of other target structures in the subject, or of a second type of target structure (e.g., a different cell type). Here, a first wavelength would induce the predetermined change and a second wavelength would mediates, initiates or enhances a biological activity of other target structures in the subject, or of a second type of target structure (e.g., a different cell type).

In a further embodiment, a biocompatible emitting source, such as a fluorescing metal nanoparticle or fluorescing dye molecule, is selected that emits in the UV-A band. The UV-A emitting source is directed to the site of a disease or condition. The UV-A emitting source may be directed to the site of the disease or condition by systemically administering the UV-A emitting source. Preferably, the UV-A emitting source is concentrated in the target site, such as by physical insertion or by conjugating the UV-A emitting molecule with a specific carrier that is capable of concentrating the UV-A emitting source in a specific target structure, as is known in the art.

In one embodiment, the UV-A emitting source is a gold nanoparticle comprising a cluster of 5 gold atoms, such as a water soluble quantum dot encapsulated by polyamidoamine dendrimers. The gold atom clusters may be produced (for example according to procedures known in the art) through a slow reduction of gold salts (e.g. $HAuCl_4$ or $AuBr_3$) or other encapsulating amines, for example. One advantage of such a gold nanoparticle is the increased Foerster distance (i.e. $R_0$), which may be greater than 100 angstroms.

In one embodiment of this invention, in addition to the UV-A emitting source, a UV-B or UV-C emitting source is directed to the site of a disease or condition to act as a germicide. In one embodiment of this invention, in addition to the UV-A emitting source, a NIR emitting source is directed to the site of a disease or condition to act as an anti-inflammatory or to promote cellular proliferation or to reduce pain. A number of commercially available drugs described below could also be activated by the a NIR emitting source.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Figure 2A:
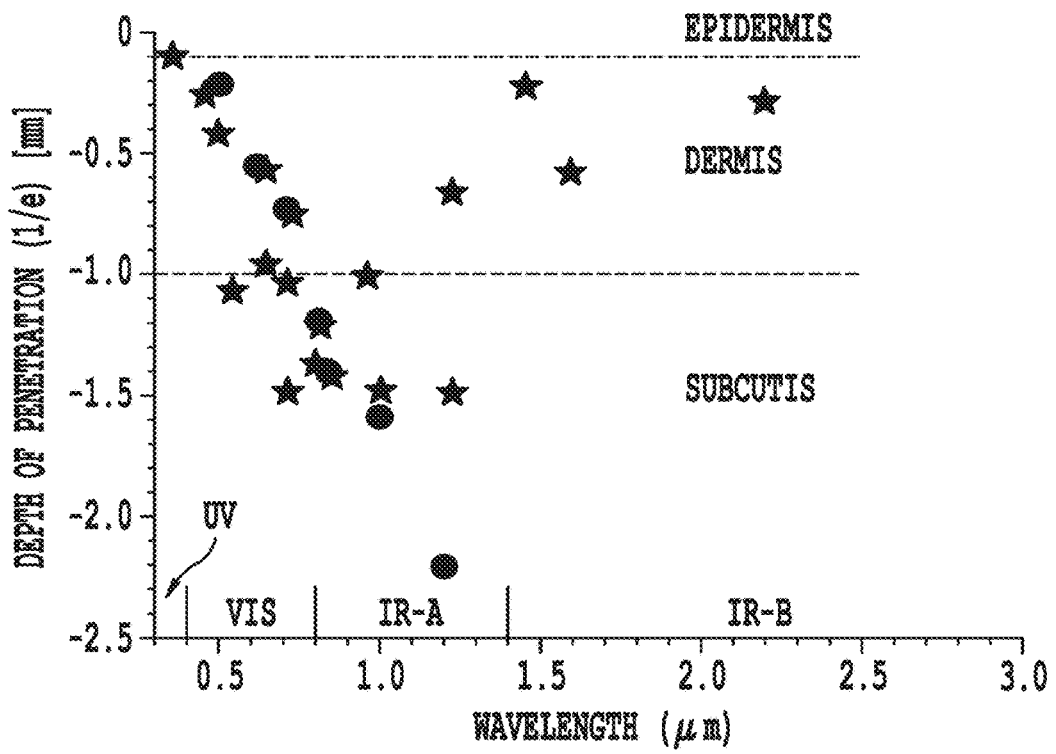
FIG. 2A and FIG. 2B are graphical representations of the depth of penetration of various wavelengths of energy into living tissue
Figure 2B:
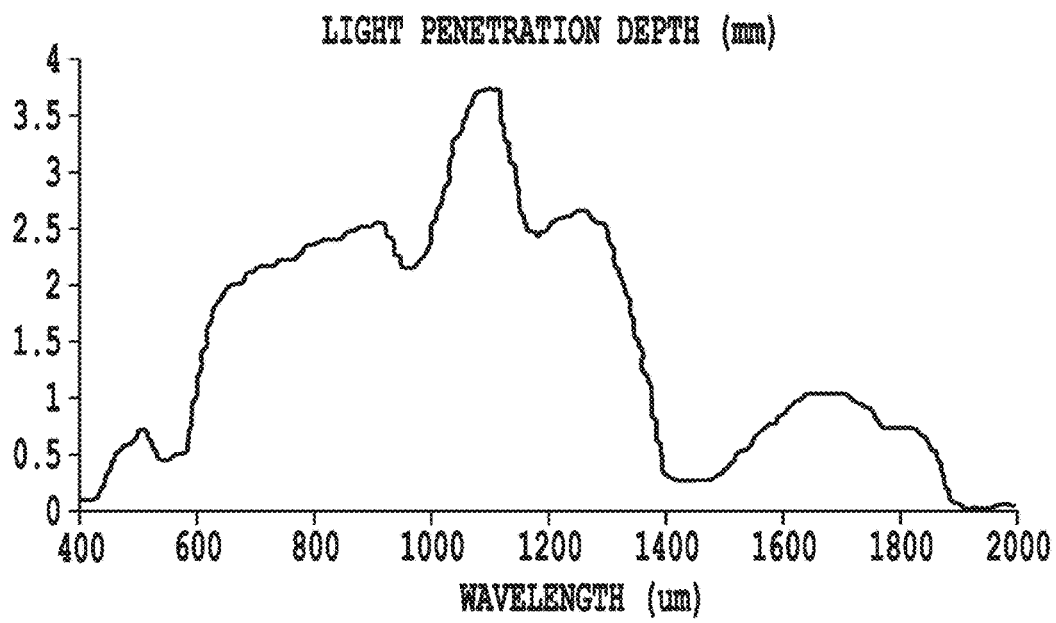

Motexafin lutetium (Lutetium texaphryin) is activated by light in the near infared region (732 nm). Absorption at this wavelength has the advantage of potentially deeper penetration into tissues, compared with the amount of light used to activate other photosensitizers (FIGS. 2A and 2B). Lutetium texaphryin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

While the description of the invention describes specific examples using nanoparticles, the present invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

In one embodiment, similar to that described above, the first wavelength would induce the predetermined change and the second wavelength would mediates, initiates or enhances neuronal spike firing For example, a light-sensitive protein (for example, channelrhodopsin-2 (ChR2) and chloride pump halorhodopsin (NpHR)) can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment for use as either the first or second wavelength, a lanthanide chelate capable of intense luminescence is used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures to irradiate the target structure, after exposure to the lanthanide chelate and a photoactive molecule.

In another embodiment for use as either the first or second wavelength, a biocompatible, endogenous fluorophore emitter is selected to stimulate resonance energy transfer to a photoactivatable molecule. A biocompatible emitter with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

In general, any source for activation of the pharmaceutical agent, such as electrical, chemical and/or radiation, can be used individually or combined into a system for activating an activatable molecule. The process may be a photopheresis process or may be similar to photophoresis. While photophoresis is generally thought to be limited to photonic excitation, such as by UV-light, other forms of radiation may be used as a part of a system to activate an activatable molecule. Radiation includes ionizing radiation which is high energy radiation, such as an X-ray or a gamma ray, which interacts to produce ion pairs in matter. Radiation also includes high linear energy transfer irradiation, low linear energy transfer irradiation, alpha rays, beta rays, neutron beams, accelerated electron beams, and ultraviolet rays. Radiation also includes proton, photon and fission-spectrum neutrons. Higher energy ionizing radiation may be combined with chemical processes to produce energy states favorable for resonance energy transfer, for example. Other combinations and variations of these sources of excitation energy may be combined as is known in the art, in order to stimulate the activation of an activatable molecule, such as 8-MOP. In one example, ionizing radiation is directed at a solid tumor and stimulates, directly or indirectly, activation of 8-MOP, as well as directly damaging the DNA of malignant tumor cells. In this example, either the effect of ionizing radiation or the photophoresis-like activation of 8-MOP may be thought of as an adjuvant therapy to the other.

In one embodiment, the present invention provides a method for treating a condition, disease or disorder mediated by a target structure in a subject, comprising:
 (1) administering to the subject an activatable pharmaceutical agent that is capable of effecting a predetermined change when activated by exposure of the target structure to different wavelengths of UV or visible or infrared irradiation emitted from at least one energy modulation agent in a vicinity of or within the target structure; and
 (2) applying an initiation energy from an initiation energy source to the subject,
 wherein the initiation energy source is a source of energy capable of penetrating completely through the subject, and wherein the applying activates the activatable agent in situ,
  thus causing the predetermined change to occur, wherein occurrence of the predetermined change in the target structure causes an increase in rate or decrease in rate of cell division and/or growth to treat the condition, disease or disorder.

In a further embodiment, the present invention provides a method for treating a condition, disease or disorder mediated by a target structure in a subject, comprising:
 (1) administering to the subject one or more energy modulation agents and an activatable pharmaceutical agent that is capable of effecting a predetermined change in the target structure when activated by exposure of the target structure to different wavelengths of UV or visible or infrared irradiation emitted from at least one energy modulation agent in a vicinity of or within the target structure; and
 (2) applying an initiation energy from an initiation energy source to the subject,
 wherein the one or more energy modulation agents convert the initiation energy applied to UV-A or visible energy, which then activates the activatable agent in situ,
  thus causing the predetermined change to occur, wherein occurrence of the predetermined change causes an increase in rate or decrease in rate of cell division and/or growth to treat the condition, disease or disorder.

In a different embodiment, the activatable pharmaceutical agent can be activated by a single or multiphoton absorption event.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the present invention.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the present invention also provides methods for producing an autovaccine, including: (1) providing a population of targeted cells; (2) treating the cells ex vivo with a psoralen or a derivative thereof; (3) activating the psoralen with an initiation energy source to induce a predetermined change in a target structure in the population of the target cells by exposure of the target structure to different wavelengths of UV or visible or infrared irradiation emitted from at least one energy modulation agent in a vicinity of or within the target structure; and (4) returning the treated cells back to the host to induce an autovaccine effect against the targeted cell, wherein the treated cells cause an autovaccine effect.

In a different embodiment, a method for generating an autovaccine for a subject, comprises:
(1) providing a population of target cells;
(2) treating the target cells ex vivo in an environment separate and isolated from the subject with an activatable pharmaceutical agent capable of activation by a multi photon absorption event;
(3) exposing the treated target cells to an energy source;
(4) activating the activatable pharmaceutical agent with the energy source by the multi photon absorption event to induce a predetermined change in at least one target structure in the target cells by exposure of the target cells to different wavelengths of UV or visible or infrared irradiation emitted from at least one energy modulation agent in a vicinity of or within the target cell; and
(5) returning the thus changed cells back to the subject to induce in the subject an autovaccine effect against the target cells.

In a further embodiment, methods in accordance with the present invention may further include a method for modifying a target structure which mediates or is associated with a biological activity, comprising:
(1) contacting said target structure with at least one activatable pharmaceutical agent that is capable of effecting a predetermined change in a target structure when activated and at least one plasmonics-active agent; and
(2) applying an initiation energy from an initiation energy source to target structure to expose the target structure to different wavelengths of UV or visible or infrared irradiation emitted from at least one energy modulation agent in a vicinity of or within the target structure,
wherein the plasmonics-active agent enhances or modulates the applied initiation energy, such that the enhanced initiation energy activates the activatable agent
thus causing the predetermined change to the target structure to occur, wherein said predetermined change modifies the target structure and modulates the biological activity of the target structure.

In a different embodiment, the predetermined change enhances the expression of, promotes the growth of, or increases the quantity of said target structure; enhances, inhibits or stabilizes the usual biological activity of said target structure compared to a similar untreated target structure, and/or alters the immunological or chemical properties of said target structure. In a different embodiment, said target structure is a compound that is modified by said predetermined change to be more or less antigenic or immunogenic The activatable pharmaceutical agent and derivatives thereof as well as the energy modulation agent, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

In one embodiment of the invention, there is provided a pharmaceutical composition for modifying a target structure. The pharmaceutical composition includes at least one agent selected from the group consisting of energy modulation agents, plasmonics-active agents and combinations thereof. The energy modulation agents includes one or more light emitters capable of emitting at least two different wavelengths of light, each wavelength of light associated with a different biological response, and the different wavelengths capable of activating different biological responses. The pharmaceutical composition preferably includes a pharmaceutically acceptable carrier.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy modulation agent, while in other embodiments the energy modulation agent may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

A further embodiment is the use of the present invention for the treatment of skin cancer. In this example, a photo-activatable agent, preferably psoralen, is given to the patient, and is delivered to the skin lesion via the blood supply. An activation source having limited penetration ability (such as UV or IR) is shined directly on the skin—in the case of psoralen, it would be a UV light, or an IR source. With the use of an IR source, the irradiation would penetrate deeper and generate UV via two single photon events with psoralen. The skin lesion is exposed to different wavelengths of UV or visible or infrared irradiation emitted from at least one energy modulation agent in a vicinity of or within the skin lesion.

In a further embodiment, methods according to this aspect of the present invention further include a step of separating the components of the treated cells into fractions and testing each fraction for autovaccine effect in a host. The components thus isolated and identified may then serve as an effective autovaccine to stimulate the host's immune system to suppress growth of the targeted cells.

In another aspect, the present invention further provides systems and kits for practicing the above described methods.

In one embodiment, a system for producing an autovaccine in a subject, comprises:
  at least one activatable pharmaceutical agent that is capable of activation by a multiphoton absorption event and of inducing a predetermined cellular change via at least one target structure in a target cell in said subject by exposure of the target structure to different wavelengths of UV or visible or infrared irradiation emitted from at least one energy modulation agent in a vicinity of or within the target structure;
  means for placing said at least one activatable pharmaceutical agent in said subject; and
  an initiation energy source to provide initiation energy capable of activating the at least one activatable pharmaceutical agent in said target cell by the multi photon absorption event, wherein activation is either direct or indirect.

Figure 3:
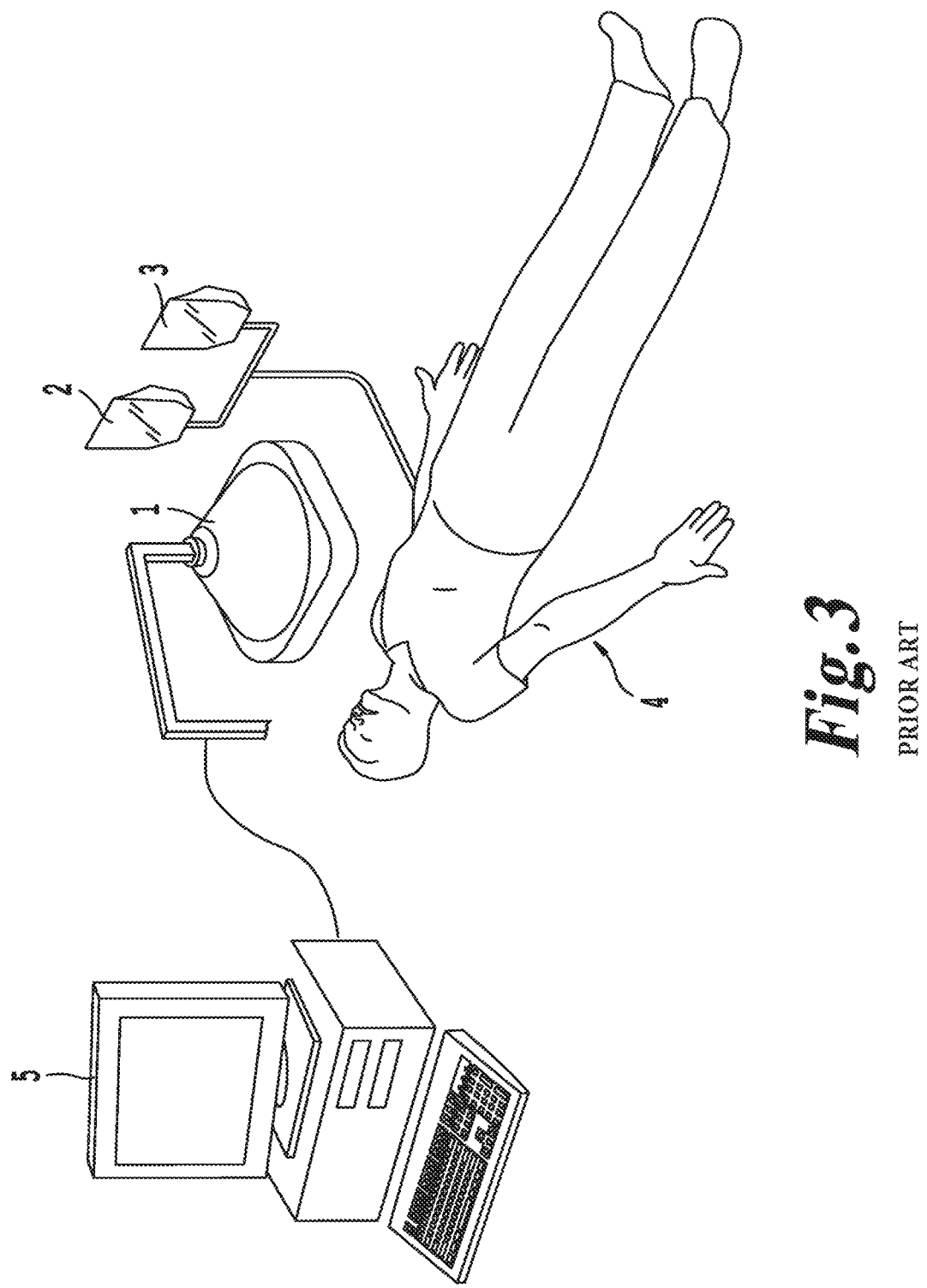
FIG. 3 illustrates a system according to one exemplary embodiment of the present invention.
Figures 1, 3:
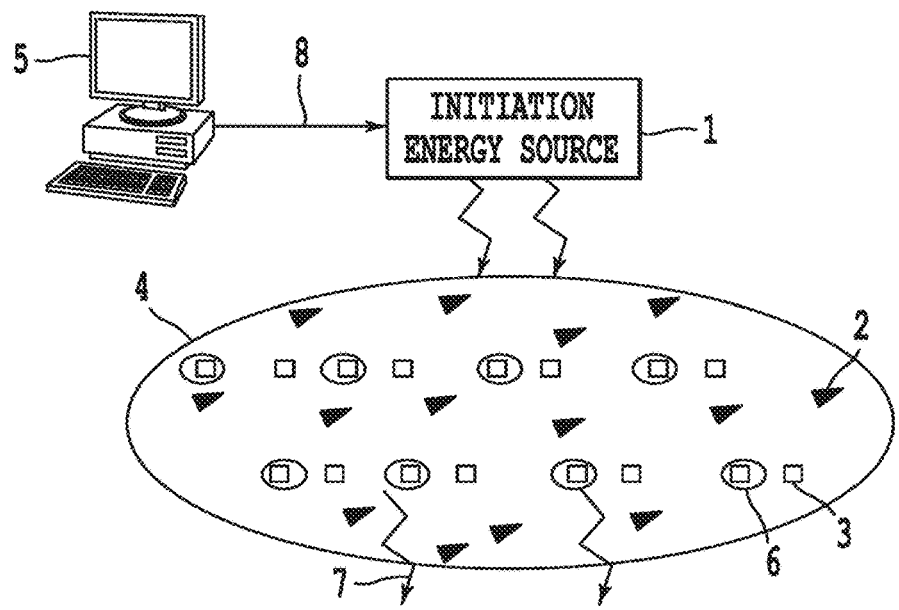

In a different embodiment, a system in accordance with the present invention may include: (1) an initiation energy source; and (2) one or more energy modulation agents. The system may further comprise (3) one or more activatable pharmaceutical agents. In an additional embodiment, the system may comprise only (1) the initiation energy source. In yet another embodiment, the system may comprise (1) an initiation energy source; and (3) one or more activatable pharmaceutical agents. FIG. 3 illustrates a system according to one exemplary embodiment of the present invention. Referring to FIG. 3, an exemplary system according to one embodiment of the present invention may have an initiation energy source 1 directed at the subject 4. An activatable pharmaceutical agent 2 and an energy modulation agent 3 are administered to the subject 4. The initiation energy source may additionally be controlled by a computer system 5 that is capable of directing the delivery of the initiation energy.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site.

In further embodiments, dose calculation and robotic manipulation devices may also be included in the system.

In yet another embodiment, there is also provided a computer implemented system for designing and selecting suitable combinations of initiation energy source, energy transfer agent, and activatable pharmaceutical agent, comprising:
  a central processing unit (CPU) having a storage medium on which is provided:
    a database of excitable compounds;
    a first computation module for identifying and designing an excitable compound that is capable of binding with a target cellular structure or component; and
    a second computation module predicting the different wavelengths of UV or visible or infrared irradiation to be emitted from at least one energy modulation agent in a vicinity of or within the target cellular structure,
  wherein the system, upon selection of a target cellular structure or component, computes an excitable compound that is capable of binding with the target structure followed by a computation to predict the resonance absorption energy of the excitable compound.

Figure 4:
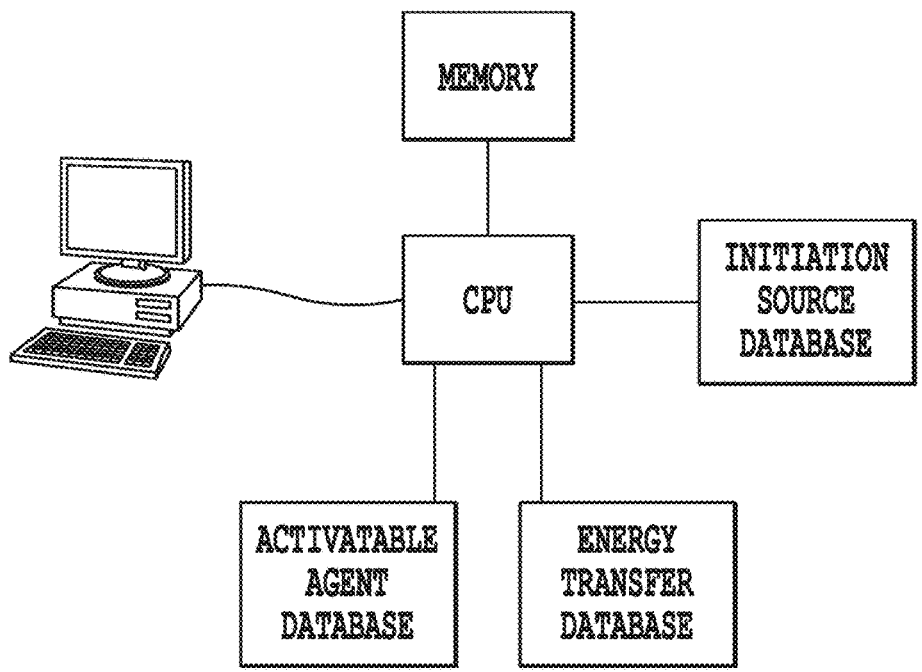
FIG. 4 illustrates an exemplary computer implemented system according to an embodiment of the present invention.

FIG. 4 illustrates an exemplary computer implemented system according to this embodiment of the present invention. Referring to FIG. 4, an exemplary computer-implemented system according to one embodiment of the present invention may have a central processing unit (CPU) connected to a memory unit, configured such that the CPU is capable of processing user inputs and selecting a combination of initiation source, activatable pharmaceutical agent, and energy transfer agent based on an energy spectrum comparison for use in a method of the present invention.

Figure 5:
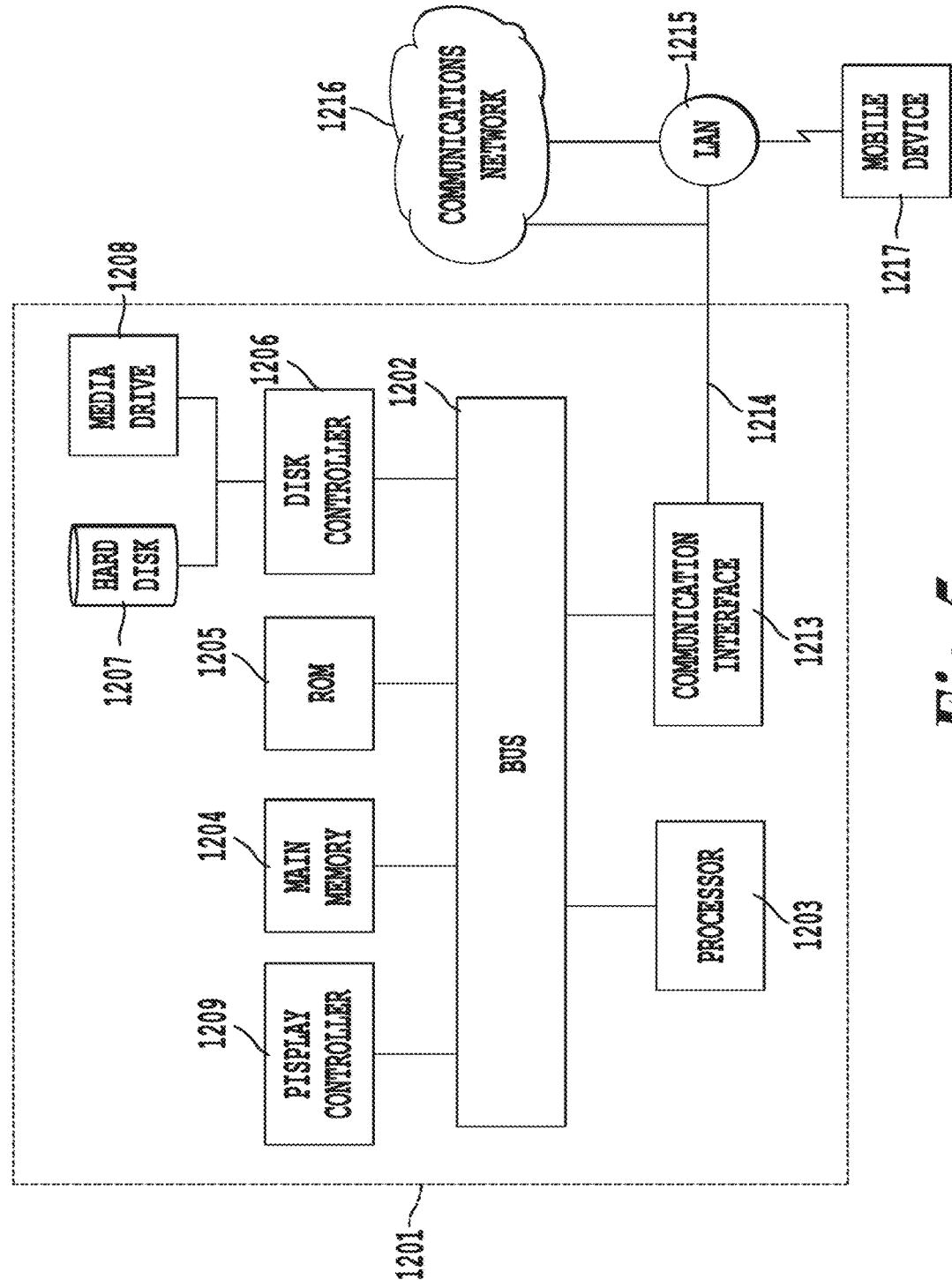
FIG. 5 illustrates an exemplary computer system (1201) for implementing various embodiments of the present invention.
Figure 6A:
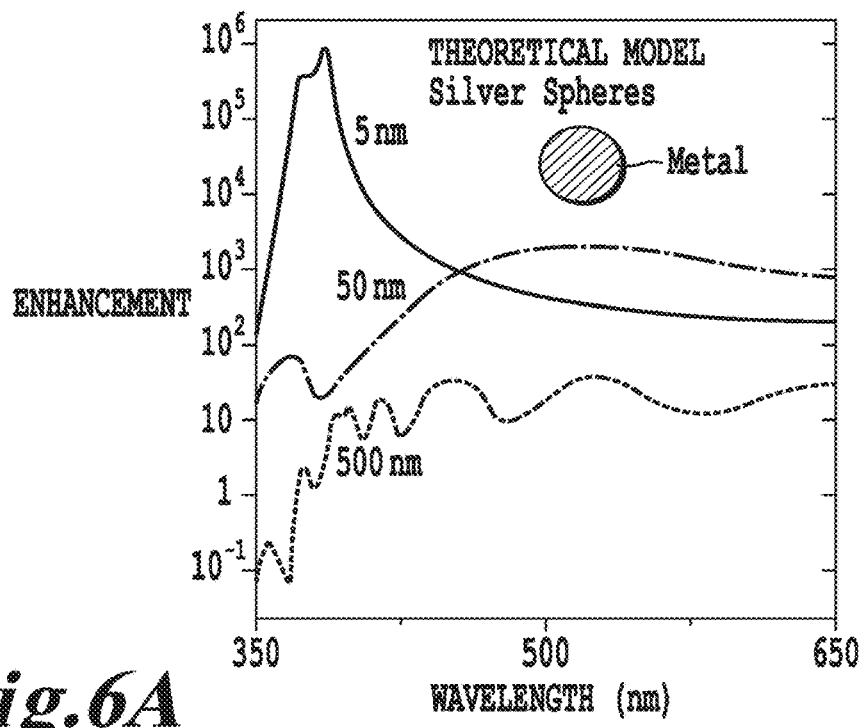
FIGS. 6A-6B are graphical representations of plasmonic nanostructures and their theoretical electromagnetic enhancement at different excitation wavelengths.
Figure 6B:
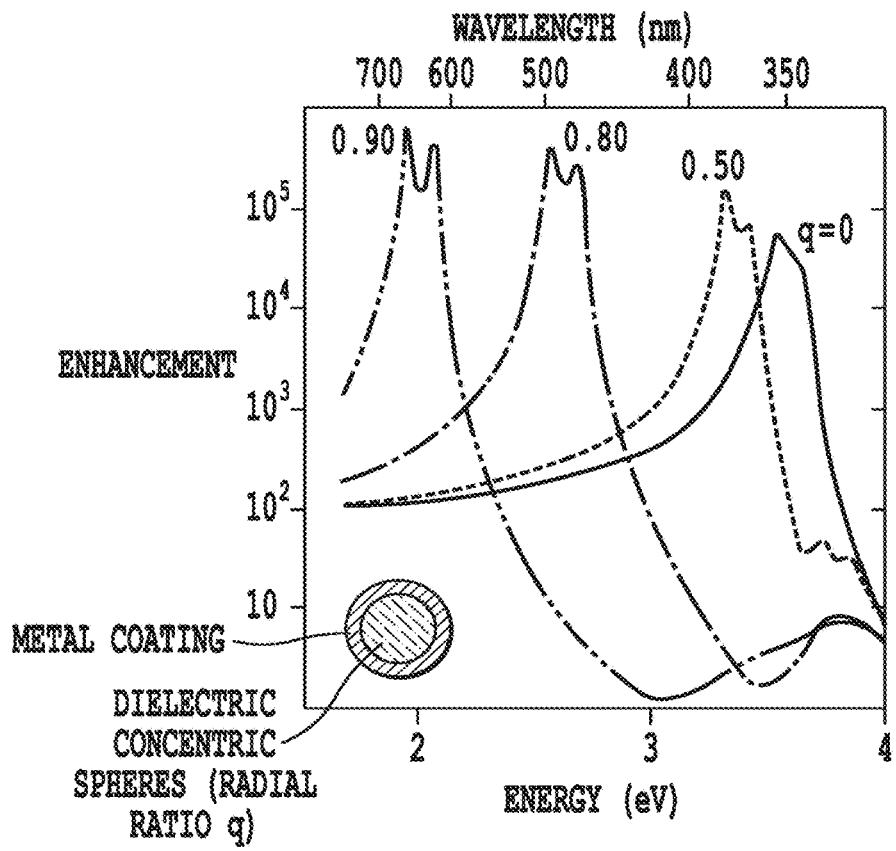

FIG. 5 illustrates a computer system 1201 for implementing various embodiments of the present invention. The computer system 1201 may be used as the controller 55 to perform any or all of the functions of the CPU described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208

(e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention (such as for example those described in relation to FIG. 5) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The exemplary energy spectrum previously noted in FIG. 1 may also be used in this computer-implemented system.

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change upon exposure of a target structure to different wavelengths of UV or visible or infrared irradiation emitted from at least one energy modulation agent in a vicinity of or within the target structure, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

In different aspect of the invention, a kit for modifying a target structure which mediates or is associated with a biological activity, comprising:

at least one agent selected from the group consisting of energy modulation agents, plasmonics-active agents and combinations thereof;

wherein the energy modulation agent, if present, upgrades or downgrades an initiation energy to an activation energy capable of causing, either directly or indirectly, a predetermined change in the target structure upon exposure of the target structure to different wavelengths of UV or visible or infrared irradiation emitted from at least one energy modulation agent in a vicinity of or within the target structure;

wherein the plasmonics-active agent, if present, enhances or modifies the applied initiation energy or the activation energy generated by the energy modulation agent, or both; and one or more containers suitable for storing the agents in stable forms.

In a different embodiment, a kit for performing a condition, disorder or disease treatment, comprises:

at least one energy modulation agent capable of adsorbing, intensifying or modifying an initiation energy into an energy that is capable of causing a predetermined change in a target structure upon exposure of a target structure to different wavelengths of UV or visible or infrared irradiation emitted from at least one energy modulation agent in a vicinity of or within the target structure; and containers suitable for storing the agents in stable form.

In yet another embodiment, the kit may further comprise instructions for administering the at least one energy modulation agent to a subject.

In various embodiments of the present invention, the plasmonics-enhanced spectroscopic properties (spectral absorption, emission, scattering) can be involved in the treatment.

The plasmonics-enhanced spectroscopic (PEPST) principle is based on the enhancement mechanisms of the electromagnetic field effect. There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified emission (luminescence, Raman, etc.) field, which further polarizes the metal particle, thereby acting as an antenna to further amplify the Raman/Luminescence signal.

Electromagnetic enhancements are divided into two main classes: a) enhancements that occur only in the presence of a radiation field, and b) enhancements that occur even without a radiation field. The first class of enhancements is further divided into several processes. Plasma resonances on the substrate surfaces, also called surface plasmons, provide a major contribution to electromagnetic enhancement. An effective type of plasmonics-active substrate comprises nanostructured metal particles, protrusions, or rough surfaces of metallic materials. Incident light irradiating these surfaces excites conduction electrons in the metal, and induces excitation of surface plasmons leading to Raman/luminescence enhancement. At the plasmon frequency, the metal nanoparticles (or nanostructured roughness) become polarized, resulting in large field-induced polarizations and thus large local fields on the surface. These local fields increase the luminescence/Raman emission intensity, which is proportional to the square of the applied field at the molecule. As a result, the effective electromagnetic field experienced by the analyte molecule on these surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if λ is in resonance with the localized surface plasmons, the nanostructures can enhance the observed emission light (Raman or luminescence).

There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified Raman/luminescence field, which further polarizes the metal particle, thereby acting as an antenna to further amplify the Raman/luminescence signal. Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents thus provides a selective and efficient phototherapy strategy. The tunability of the spectral properties of the metal nanoparticles and the biotargeting abilities of the plasmonic nanostructures make the PEPST method promising.

PEPST is based on several important mechanisms:
Increased absorption of the excitation light by the plasmonic metal nanoparticles, resulting in enhanced photoactivation of drug molecules
Increased absorption of the excitation light by the plasmonic metal nanoparticles that serve as more efficient energy modulation agent systems, yielding more light for increased excitation of PA molecules
Increased absorption of the excitation light by the photoactive drug system adsorbed on or near the plasmonic metal nanoparticles
Increased light absorption of the energy modulation agent molecules adsorbed on or near the metal nanoparticles
Amplified light emission from the energy modulation agent molecules adsorbed on or near the metal nanoparticles
Increased absorption of emission light emitted from the energy modulation agent by the PA molecule Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

Design, Fabrication and Operation of PEPST Probes

FIGS. 7A-7G show a number of the various embodiments of PEPST probes that can be designed:
(A) probe comprising PA molecules bound to a metal (gold) nanoparticle;
(B) PA-containing nanoparticle covered with metal nanoparticles;
(C) Metal nanoparticle covered with PA nanocap;
(D) PA-containing nanoparticle covered with metal nanocap;
(E) Metal nanoparticle covered with PA nanoshell;
(F) PA-containing nanoparticle covered with metal nanoshell; and
(G) PA-containing nanoparticle covered with metal nanoshell with protective coating layer.

Figure 8A:
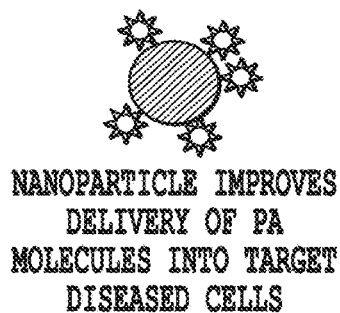

A basic embodiment of the PEPST probe is shown in FIG. 7A. This probe comprises PA molecules bound to a metal (e.g., gold) nanoparticle. FIGS. 8A-8B illustrate the plasmonics-enhancement effect of the PEPST probe. The gold nanoparticles can serve as a drug delivery platform. Gold nanoparticles have been described as a novel technology in the field of particle-based tumor-targeted drug delivery [Giulio F. Paciotti and Lonnie Myer, DavidWeinreich, Dan Goia, Nicolae Pavel, Richard E. McLaughlin, Lawrence Tamarkin, "*Colloidal Gold: A Novel Nanoparticle Vector for Tumor Directed Drug Delivery, Drug Delivery,* 11:169-183, 2004]. Particle delivery systems capable of escaping phagocytic clearance by the reticuloendothelial system (RES) can facilitate targeting cancer therapeutics to solid tumors. Such delivery systems could preferentially accumulate within the tumor microenvironment under ideal conditions. A particle delivery system capable of sequestering a phototherapeutic drug selectively within a tumor may also reduce the accumulation of the drug in healthy organs. Consequently, these delivery systems may increase the relative efficacy or safety of therapy (less radiation energy and intensity), and therefore, will increase the drug's therapeutic efficiency.

Radiation of suitable energy is used to excite the PA drug molecules (e.g., aminolevulinic acid (ALA), porphyrins) and make them photoactive. For example, with the PDT drug ALA, light of a HeNe laser (632.8-nm excitation) can be used for excitation. In this case the metal nanoparticles are designed to exhibit strong plasmon resonance band around 632.8 nm. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes in FIGS. 7B, 7C, 7D, 7E, 7F and 7G. FIGS. 34A-34G show yet another embodiment of plasmonics photo-active probes. FIGS. 35A-35G show yet another embodiment of plasmonics photo-active probes that have a dielectric layer between the metal and the UC materials.

In one embodiment, a method for treating a condition, disorder or disease in accordance with the present invention comprises:
(1) administering to the subject at least one activatable pharmaceutical agent that is capable of effecting a predetermined change in a target structure when activated and at least one plasmonics-active agent; and
(2) applying an initiation energy from an initiation energy source to the subject,
wherein the plasmonics-active agent enhances or modifies the applied initiation energy, such that the enhanced initiation energy activates the activatable agent in situ, thus causing the predetermined change to the target structure to occur, wherein said predetermined change modifies the target structure and treats said condition, disorder, or disease.

In a different embodiment, a method in accordance with the present invention comprises:
(1) contacting said target structure with at least one activatable pharmaceutical agent that is capable of effecting a predetermined change in a target structure when activated and at least one plasmonics-active agent; and
(2) applying an initiation energy from an initiation energy source to target structure to expose the target structure to different wavelengths of UV or visible or infrared irradiation emitted from at least one energy modulation agent in a vicinity of or within the target structure
wherein the plasmonics-active agent enhances or modifies the applied initiation energy, such that the enhanced initiation energy activates the activatable agent
thus causing the predetermined change to the target structure to occur, wherein said predetermined change modifies the target structure and modulates the biological activity of the target structure.

In a different embodiment, at least one energy modulation agent and/or excitation-generating energy modulation agent material may be also added. In one embodiment, the energy modulation agent or excitation-generating energy modulation agent material may adsorb, intensify or modify the initiation energy which is then enhanced by at least one plasmonic agent. In a different embodiment, the energy modulation agent or excitation-generating energy modulation agent material may adsorb, intensify or modify energy enhanced by the at least plasmonics-active agent and emit an energy that is capable to activate the pharmaceutical activatable agent.

In another embodiment, the predetermined change enhances the expression of, promotes the growth of, or increases the quantity of said target structure. In yet, different embodiment, the predetermined change enhances, inhibits or stabilizes the usual biological activity of said target structure compared to a similar untreated target structure. In a different embodiment, the predetermined change alters the immunological or chemical properties of said target structure. In a different embodiment, the target structure is a compound that is modified by said predetermined change to be more or less antigenic or immunogenic.

Structures of Plasmonics-Active Metal Nanostructures

These shells typically comprise a metallic layer over a dielectric core. In one embodiment of the present invention, shells comprising a metallic layer over a dielectric core can be spheroidal shells. The plasmon resonances (both longitudinal and transverse modes) are influenced by both shell thickness and aspect ratio. The present invention also includes prolate and oblate spheroidal shells, which show some interesting qualitative features in their plasmon resonances. The spheroidal shell presents two degrees of freedom for tuning: the shell thickness and the shell aspect ratio.

FIGS. 9A-9J show some of the various embodiments of plasmonics-active nanostructures that can be designed, and are preferred embodiments of the present invention:
(A) Metal nanoparticle;
(B) Dielectric nanoparticle core covered with metal nanocap;
(C) Spherical metal nanoshell covering dielectric spheroid core;
(D) Oblate metal nanoshell covering dielectric spheroid core;
(E) Metal nanoparticle core covered with dielectric nanoshell;
(F) Metal nanoshell with protective coating layer;
(G) Multi layer metal nanoshells covering dielectric spheroid core;
(H) Multi-nanoparticle structures;
(I) Metal nanocube and nanotriangle/nanoprism; and
(J) Metal cylinder.

Figure 10:
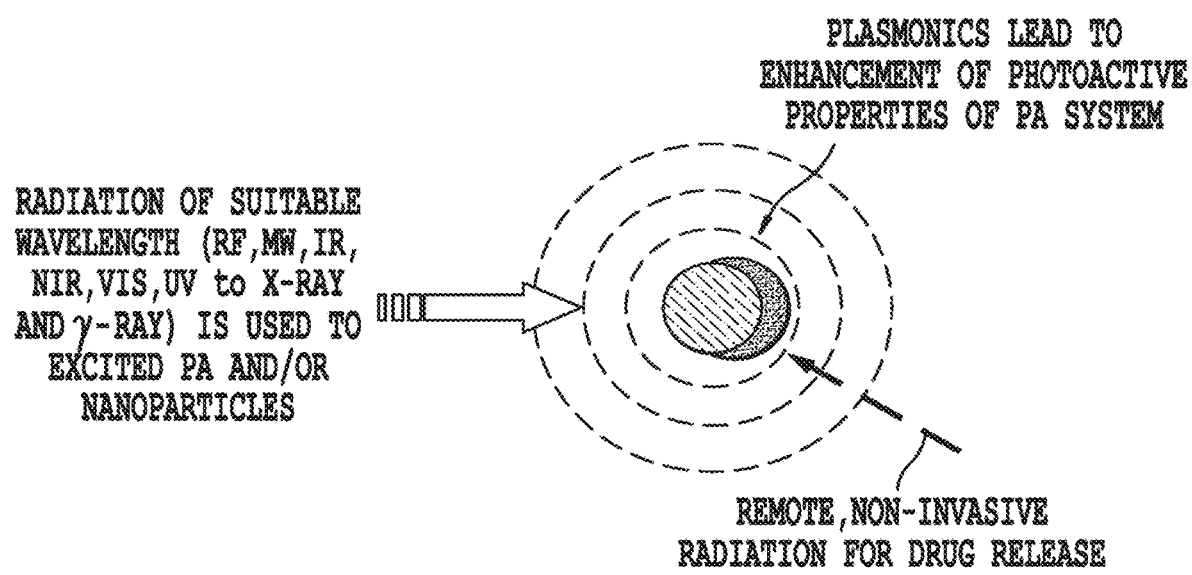
FIG. 10 is a graphical representation of one embodiment of a PEPST probe with remote drug release.

In a further embodiment of the present invention, the PA drug molecules can be incorporated into a material (e.g., biocompatible polymer) that can form a nanocap onto the metal (gold) nanoparticles. The material can be a gel or biocompatible polymer that can have long-term continuous drug release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers. The drug release mechanism can also be triggered by non-invasive techniques, such as RF, MW, ultrasound, photon (FIG. 10).

Figure 11A:
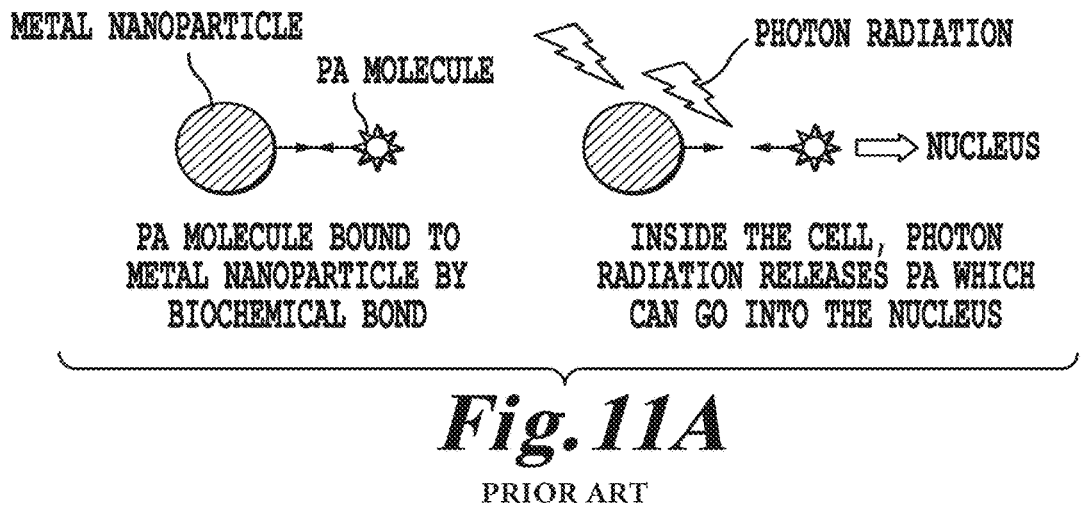
FIGS. 11A-11C are graphical representations of several embodiments of PEPST probes with various linkers for remote drug release.
Figure 11B:
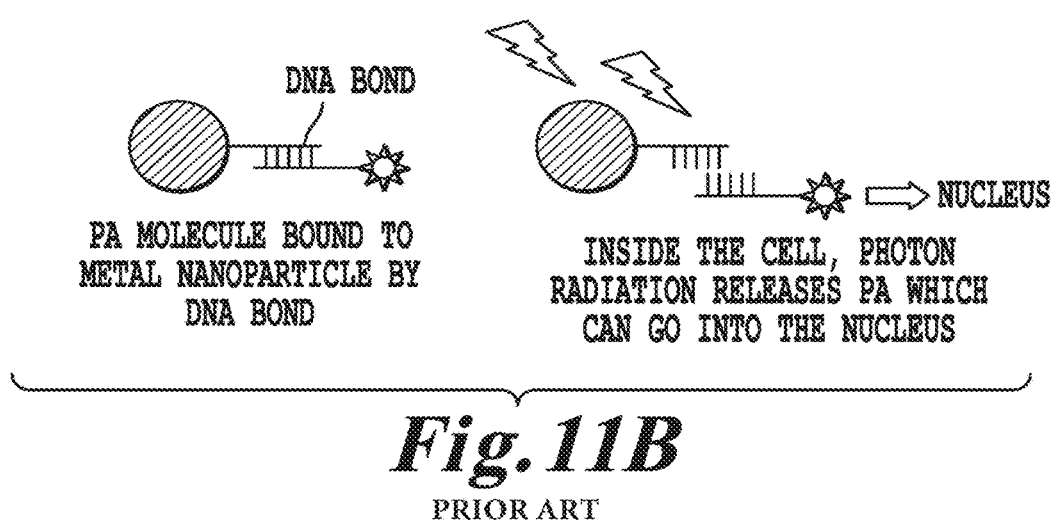
Figure 11C:
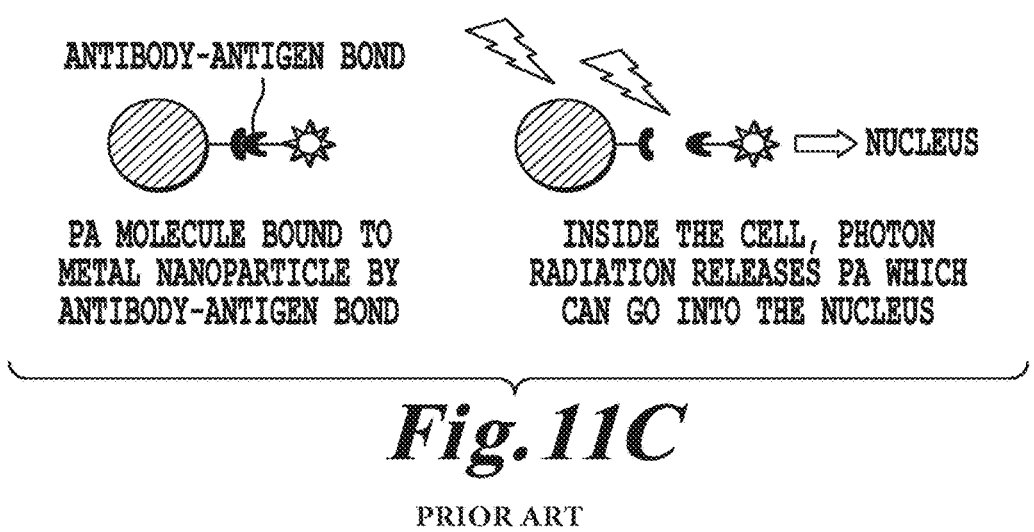

FIGS. 11A-11C show other possible embodiments where the PA drug molecule is bound to the metal nanoparticles via a linker that can be cut by a photon radiation. Such a linker includes, but is not limited to, a biochemical bond (FIG. 11A), a DNA bond (FIG. 11B), or an antibody-antigen bond (FIG. 11C). In another embodiment, the linker is a chemically labile bond that will be broken by the chemical environment inside the cell. These types of probes are useful for therapy modalities where the PA molecules have to enter the nucleus (e.g., psoralen molecules need to enter the nucleus of cells and intercalate onto DNA). Since it is more difficult for metal nanoparticles to enter the cell nucleus than for smaller molecules, it is desirable to PEPST probes that have releasable PA molecules.

Aggregation of metal (such as silver or gold) nanoparticles (nanospheres, nanorods, etc) is often a problem, especially with citrate-capped gold nanospheres, cetyl trimethylammonium bromide (CTAB)-capped gold nanospheres and nanorods and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles). Furthermore, PEGylated nanoparticles are preferentially accumulated into tumor tissues due to the enhanced permeability and retention effect, known as the "EPR." Blood vessels in tumor tissue are more "leaky" than in normal tissue, and as a result, particles, or large macromolecular species or polymeric species preferentially extravasate into tumor tissue. Particles and large molecules tend to stay a longer time in tumor tissue due to the decreased lymphatic system, whereas they are rapidly cleared out in normal tissue. This tumor targeting strategy is often referred to as passive targeting whereas the antibody-targeting strategy is called active targeting.

To specifically target diseased cells, specific genes or protein markers, the drug systems of the present invention can be bound to a bioreceptor (e.g., antibody, synthetic molecular imprint systems, DNA, proteins, lipids, cell-surface receptors, aptamers, etc.). Immunotargeting modalities to deliver PA agents selectively to the diseased cells and tissue provide efficient strategies to achieving specificity, minimizing nonspecific injury to healthy cells, and reducing the radiation intensity used. Biofunctionalization of metal nanoparticles (e.g., gold, silver) can be performed using commonly developed and widely used procedures. There are several targeting strategies that can be used in the present invention: (a) nanoparticles conjugated to antibodies that recognize biomarkers specific to the diseased cells; (b) nanoparticles passivated by poly (ethylene) glycol (PEG), which is used to increase the biocompatibility and biostability of nanoparticles and impart them an increased blood retention time.

Bioreceptors are the key to specificity for targeting disease cells, mutated genes or specific biomarkers. They are responsible for binding the biotarget of interest to the drug system for therapy. These bioreceptors can take many forms and the different bioreceptors that have been used are as numerous as the different analytes that have been monitored using biosensors. However, bioreceptors can generally be classified into five different major categories. These categories include: 1) antibody/antigen, 2) enzymes, 3) nucleic acids/DNA, 4) cellular structures/cells and 5) biomimetic. FIGS. 12A-12G illustrate a number of embodiments of the various PEPSI probes with bioreceptors that can be designed.

Antibody Probes. Antibody based targeting is highly active, specific and efficient. The antibodies are selected to target a specific tumor marker (e.g., anti-epidermal growth factor receptor (EGFR) antibodies targeted against overexpressed EGFR on oral and cervical cancer cells; anti-Her2 antibodies against overexpressed Her2 on breast cancer cells) Antibodies are biological molecules that exhibit very specific binding capabilities for specific structures. This is very important due to the complex nature of most biological systems. An antibody is a complex biomolecule, made up of hundreds of individual amino acids arranged in a highly ordered sequence. For an immune response to be produced against a particular molecule, a certain molecular size and complexity are necessary: proteins with molecular weights greater than 5000 Da are generally immunogenic. The way in which an antigen and its antigen-specific antibody interact may be understood as analogous to a lock and key fit, by which specific geometrical configurations of a unique key enables it to open a lock. In the same way, an antigen-specific antibody "fits" its unique antigen in a highly specific manner. This unique property of antibodies is the key to their usefulness in immunosensors where only the specific analyte of interest, the antigen, fits into the antibody binding site.

DNA Probes. The operation of gene probes is based on the hybridization process. Hybridization involves the joining of a single strand of nucleic acid with a complementary probe sequence. Hybridization of a nucleic acid probe to DNA biotargets (e.g., gene sequences of a mutation, etc) offers a very high degree of accuracy for identifying DNA sequences complementary to that of the probe. Nucleic acid strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e., gene probe) detection methods are very specific to DNA sequences. Factors affecting the hybridization or reassociation of two complementary DNA strands include temperature, contact time, salt concentration, and the degree of mismatch between the base pairs, and the length and concentration of the target and probe sequences.

Biologically active DNA probes can be directly or indirectly immobilized onto a drug system, such as the energy modulation agent system (e.g., gold nanoparticle, a semiconductor, quantum dot, a glass/quartz nanoparticles, etc.) surface to ensure optimal contact and maximum binding. When immobilized onto gold nanoparticles, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. The silanization methods have been used for binding to glass surfaces using 3 glycidoxypropyltrimethoxysilane (GOP) or aminopropyltrimethoxysilane (APTS), followed by covalently linking DNA via amino linkers incorporated either at the 3' or 5' end of the molecule during DNA synthesis.

Enzyme Probes. Enzymes are often chosen as bioreceptors based on their specific binding capabilities as well as their catalytic activity. In biocatalytic recognition mechanisms, the detection is amplified by a reaction catalyzed by macromolecules called biocatalysts. With the exception of a small group of catalytic ribonucleic acid molecules, all enzymes are proteins. Some enzymes require no chemical groups other than their amino acid residues for activity. Others require an additional chemical component called a cofactor, which may be either one or more inorganic ions, such as $Fe^{2+}$, $Mg^{2+}$, $Mn^{2+}$, or $Zn^{2+}$, or a more complex organic or metalloorganic molecule called a coenzyme. The catalytic activity provided by enzymes allows for much lower limits of detection than would be obtained with common binding techniques. The catalytic activity of enzymes depends upon the integrity of their native protein conformation. If an enzyme is denatured, dissociated into its subunits, or broken down into its component amino acids, its catalytic activity is destroyed. Enzyme-coupled receptors can also be used to modify the recognition mechanisms.

In one embodiment, nanoparticles of metal colloid hydrosols are prepared by rapidly mixing a solution of $AgNO_3$ with ice-cold $NaBH_4$. For developing a SMP probes, a DNA segment is bound to a nanoparticle of silver or gold. The immobilization of biomolecules (e.g., DNA, antibodies, enzymes, etc.) to a solid support through covalent bonds usually takes advantage of reactive groups such as amine ($—NH_2$) or sulfide (—SH) that naturally are present or can be incorporated into the biomolecule structure. Amines can react with carboxylic acid or ester moieties in high yield to form stable amide bonds. Thiols can participate in maleimide coupling yielding stable dialkylsulfides.

In one embodiment, silver nanoparticles are used. In one embodiment, the immobilization schemes involving Ag surfaces utilize a prior derivatization of the surface with alkylthiols, forming stable linkages are used. Alkylthiols readily form self-assembled monolayers (SAM) onto silver surfaces in micromolar concentrations. The terminus of the alkylthiol chain can be directly used to bind biomolecules, or can be easily modified to do so. The length of the alkylthiol chain was found to be an important parameter, keeping the biomolecules away from the surface. Furthermore, to avoid direct, non-specific DNA adsorption onto the surface, alkylthiols were used to block further access to the surface, allowing only covalent immobilization through the linker.

Silver/gold surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold.

After SAM formation on silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. In one embodiment, more active intermediate (labile ester) is first formed with the carboxylic acid moiety and in a later stage reacted with the free amine, increasing the coupling yield. Successful coupling procedures include:

The coupling approach used to bind DNA to a silver nanoparticle involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [4]. NHS reacts almost exclusively with primary amine groups. Covalent immobilization can be achieved in as little as 30 minutes. Since $H_2O$ competes with —$NH_2$ in reactions involving these very labile esters, it is important to consider the hydrolysis kinetics of the available esters used in this type of coupling. The derivative of NHS used in FIG. 101, O—(N-succinimidyl)-N,N,N,N'-tetramethyluronium tetrafluoroborate, increases the coupling yield by utilizing a leaving group that is converted to urea during the carboxylic acid activation, hence favorably increasing the negative enthalpy of the reaction.

Photon Excitation in the Therapeutic Window of Tissue

Figure 13:
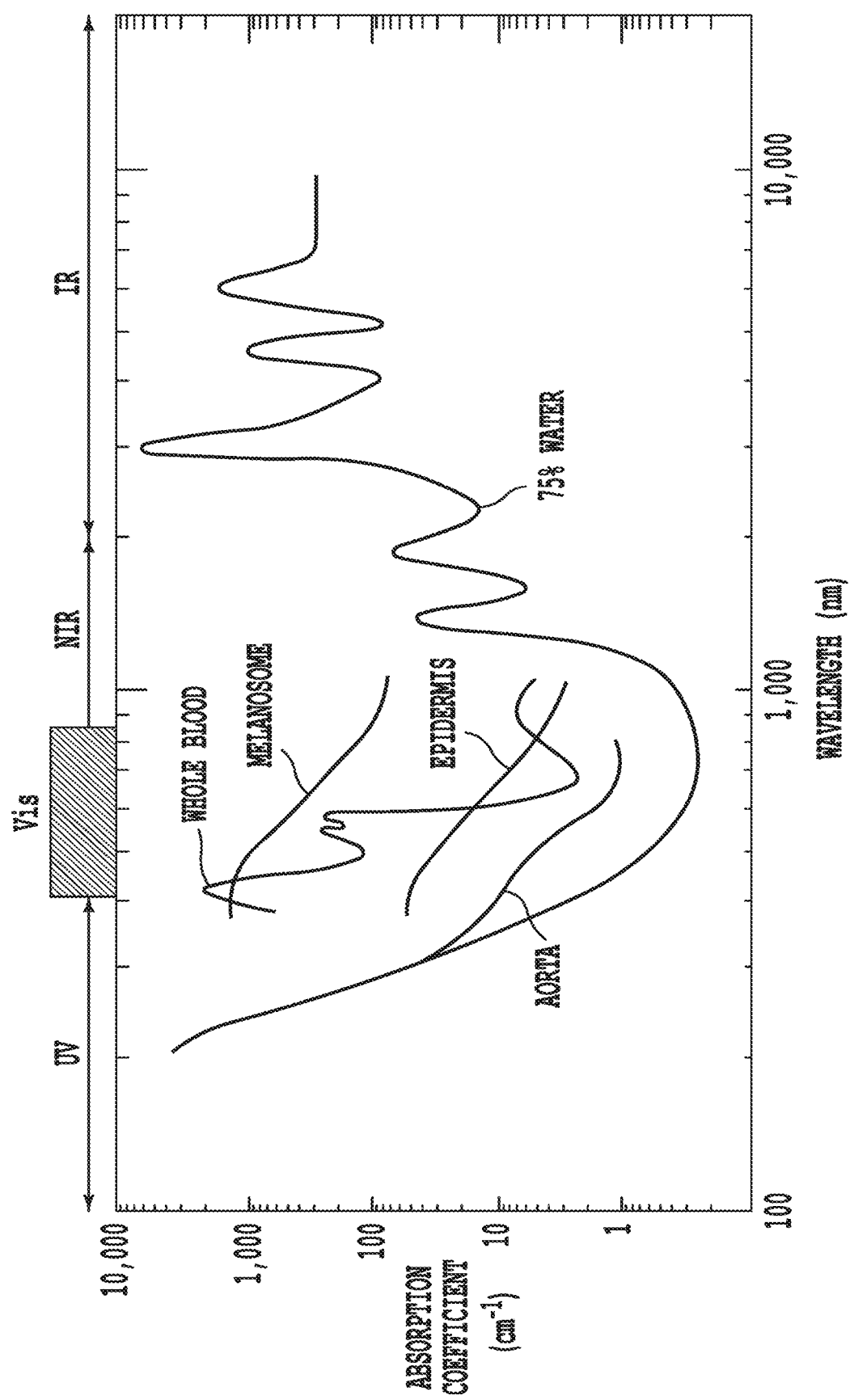
FIG. 13 is a graphical representation of the "therapeutic window" in tissue and absorption spectra of biological components.

There are several methods using light to excite photoactivate compounds non-invasively with the use of light having wavelengths within the so-called "therapeutic window" (700-1300 nm). The ability of light to penetrate tissues depends on absorption. Within the spectral range known as the therapeutic window (or diagnostic window), most tissues are sufficiently weak absorbers to permit significant penetration of light. This window extends from 600 to 1300 nm, from the orange/red region of the visible spectrum into the NIR. At the short-wavelength end, the window is bound by the absorption of hemoglobin, in both its oxygenated and deoxygenated forms. The absorption of oxygenated hemoglobin increases approximately two orders of magnitude as the wavelength shortens in the region around 600 nm. At shorter wavelengths many more absorbing biomolecules become important, including DNA and the amino acids tryptophan and tyrosine. At the infrared (IR) end of the window, penetration is limited by the absorption properties of water. Within the therapeutic window, scattering is dominant over absorption, and so the propagating light becomes diffuse, although not necessarily entering into the diffusion limit. FIG. 13 shows a diagram of the therapeutic window of tissue. The following section discusses the use of one-photon and multi-photon techniques for therapy.

Light Excitation Methods: Single-Photon and Multi-Photon Excitation

Two methods can be used, one-photon or multi-photon excitation. If the two-photon technique is used, one can excite the PA molecules with light at 700-1000 nm, which can penetrate deep inside tissue, in order to excite molecules that absorb in the 350-500 nm spectral region. This approach can excite the psoralen compounds, which absorb in the 290-350 nm spectral region and emit in the visible. With the one-photon method, the photo-activator (PA) drug molecules can directly absorb excitation light at 600-1300 nm. In this case we can design a psoralen-related system (e.g., psoralens having additional aromatic rings or other conjugation to alter the ability to absorb at different wavelengths) or use other PA systems: photodynamic therapy drugs, ALA, etc.

PEPST Modality for Photopheresis Using X Ray Excitation
Need for X-Ray Excitation Photopheresis has been demonstrated to be an effective treatment for a number of diseases. One method for an improved and practical modality for such therapy was described in U.S. Ser. No. 11/935,655, filed Nov. 6, 2007, the entire contents of which are hereby incorporated by reference.

Although X-ray can excite compounds in deep tissue non-invasively, X-ray is not easily absorbed by organic drug compounds. The present invention provides a solution to that problem, by the providing of a molecular system that can absorb the X-ray energy and change that energy into other energies that can be used to activate drug molecules. More specifically, the molecular system that can absorb and change the X-ray energy in the present invention is the PEPST probes comprising nanoparticles.

Figure 14:
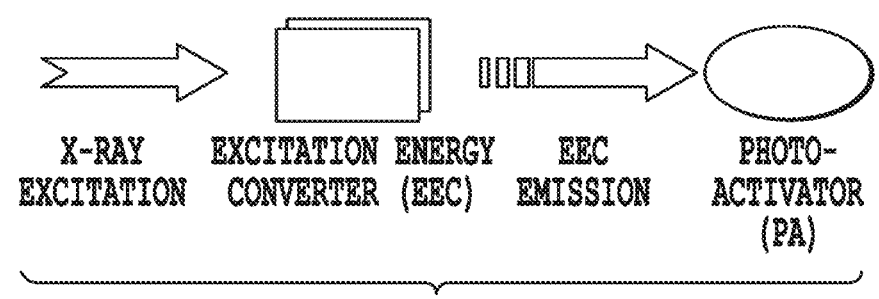
FIG. 14 is a graphical representation of an embodiment of the energy modulation agent(or excitation energy converter/EEC)-photo activator (PA) system of the present invention.

In this embodiment, the present invention uses X-rays for excitation. The advantage is the ability to excite molecules non-invasively since X-ray can penetrate deep in tissue. However, the limitation is the fact that X-ray does not interact with most molecules. In one embodiment of the present invention, the drug molecule (or PA) is bound to a molecular entity, referred to as an "energy modulation agent" that can interact with the X-rays, and then emit light that can be absorbed by the PA drug molecules. (FIG. 14)

PEPST Probes for X Ray Excitation

The dose delivered to a tumor during photon-based radiation therapy can be enhanced by loading high atomic number (Z) materials such as gold (Au, Z=79) into the tumor, resulting in greater photoelectric absorption within the tumor than in surrounding tissues. Thus, gold clearly leads to a higher tumor dose than either iodine or gadolinium. Second, nanoparticles provide a better mechanism than microspheres, in terms of delivering high-Z materials to the tumor, overcoming some of the difficulties found during an earlier attempt using gold microspheres Gold (or metal) complexes with PA ligands: Gold (or metal) complexes with PA can preferably be used in the present invention. The metal can be used as an energy modulation agent system. For example, gold complexes with psoralen-related ligands can be used as a hybrid energy modulation agent-PA system. The gold molecules serve as the energy modulation agent system and the ligand molecules serve as the PA drug system. Gold(I) complexes with diphosphine and bipyridine ligands exhibit X-ray excited luminescence FIGS. 15A-15F show a number of the various embodiments of PEPST probes that can be preferably used for X ray excitation of energy modulation agent-PA system. These probes comprise:

(A) PA molecules bound to energy modulation agent and to plasmonic metal nanoparticle;
(B) Plasmonic metal nanoparticle with energy modulation agent nanocap covered with PA molecules;
(C) PA-covered nanoparticle with plasmonic metal nanoparticles;
(D) Energy modulation agent-containing nanoparticle covered with PA molecules and plasmonic metal nanocap;
(E) Plasmonic metal nanoparticle core with energy modulation agent nanoshell covered with PA molecule; and
(F) PA molecule bound to energy modulation agent (attached to plasmonics metal nanoparticle) nanoparticle by detachable biochemical bond.

Examples of PEPST System Based on Energy Modulation Agent-PA

For purposes of simplification, the following discussion is centered on gold as the metal material and CdS as the energy modulation agent material (which can also be used as DNA stabilized CdS, see Ma et al, *Langmuir,* 23 (26), 12783-12787 (2007)) and psoralen as the PA molecule. However, it is to be understood that many other embodiments of metal material, energy modulation agent and PA molecule are possible within the bounds of the present invention, and the following discussion is for exemplary purposes only. Suitable metals that can be used in plasmon resonating shells or other plasmon resonating structures can be include, but are not limited to, gold, silver, platinum, palladium, nickel, ruthenium, rhenium, copper, and cobalt.

In the embodiment of FIG. 15A, the PEPST system comprises gold nanoparticles, an energy modulation agent nanoparticle (e.g., CdS) linked to a PA drug molecule (e.g., psoralen). X ray is irradiated to CdS, which absorbs X rays and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In the embodiment of FIG. 15B, the PEPST system comprises a plasmonics-active metal (gold) nanoparticle with energy modulation agent nanocap (CdS) covered with PA molecules (e.g., psoralen). X ray is irradiated to CdS, which absorbs X ray and emits XEOL light that is plasmonics-enhanced by the gold nanoparticle. This enhanced XEOL light is used to photoactivate psoralen (PA molecule).

In the embodiment of FIG. 15C, the PEPST system comprises a PA (e.g., psoralen)-covered CdS nanoparticle with smaller plasmonic metal (gold) nanoparticles. X ray is irradiated to CdS, which absorbs X ray and emits XEOL light that is plasmonics-enhanced by the gold nanoparticle. This enhanced XEOL light is used to photoactivate psoralen (PA molecule).

In the embodiment of FIG. 15D, the energy modulation agent core comprises CdS or CsCl nanoparticles covered with a nanocap of gold. X ray is irradiated to CdS or CsCl, which absorbs X ray and emits XEOL light that is plasmonics-enhanced by the gold nanocap structure. This enhanced XEOL light is used to photoactivate psoralen (PA molecule).

Similarly, the embodiment in FIG. 15E comprises a spherical gold core covered by a shell of CdS or CsCl. X ray is irradiated to CdS or CsCl material, which absorbs X ray and emits XEOL light that is plasmonics-enhanced by the gold nanosphere. This enhanced XEOL light is used to photoactivate psoralen (PA molecule).

In the embodiment of FIG. 15F, the PEPST system comprises gold nanoparticles, and an energy modulation agent nanoparticle (e.g., CdS) linked to a PA drug molecule (e.g., psoralen) by a link that can be detached by radiation. X ray is irradiated to CdS, which absorbs X ray and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In alternative embodiments, the metal nanoparticles or single nanoshells are replaced by multi layers of nanoshells In other alternative embodiments the metal nanoparticles are covered with a layer (1-30 nm) of dielectric material (e.g. silica). The dielectric layer (or nanoshell) is designed to prevent quenching of the luminescence light emitted by the energy modulation agent (also referred to as EEC) molecule(s) due to direct contact of the metal with the energy modulation agent molecules. In yet other alternative embodiments, the energy modulation agent molecules or materials are bound to (or in proximity of) a metal nanoparticle via a spacer (linker). The spacer is designed to prevent quenching of the luminescence light emitted by the energy modulation agent molecules or materials.

Other Useable Materials

The energy modulation agent materials can include any materials that can absorb X ray and emit light in order to excite the PA molecule. The energy modulation agent materials include, but are not limited to:

metals (gold, silver, etc);
quantum dots;
semiconductor materials;
scintillation and phosphor materials;
materials that exhibit X-ray excited luminescence (XEOL);
organic solids, metal complexes, inorganic solids, crystals, rare earth materials (lanthanides), polymers, scintillators, phosphor materials, etc.; and
materials that exhibit excitonic properties.

Quantum dots, semiconductor nanostructures. Various materials related to quantum dots, semiconductor materials, etc. can be used as energy modulation agent systems. For example CdS-related nanostructures have been shown to exhibit X-ray excited luminescence in the UV and/or visible region. For example, ZnO nanoparticles or quantum-dots could be used for excited luminescence in the UV and/or visible region.

Scintillator Materials as energy modulation agent systems. Various scintillator materials can be used as energy modulation agents since they absorb X-ray and emit luminescence emission, which can be used to excite the PA system. For example, single crystals of molybdates can be excited by X-ray and emit luminescence around 400 nm Solid Materials as energy modulation agent systems: Various solid materials can be used as energy modulation agents due to their X-ray excited luminescence properties. For example CdS (or CsCl) exhibit luminescence when excited by soft X-ray.

Figure 16A:
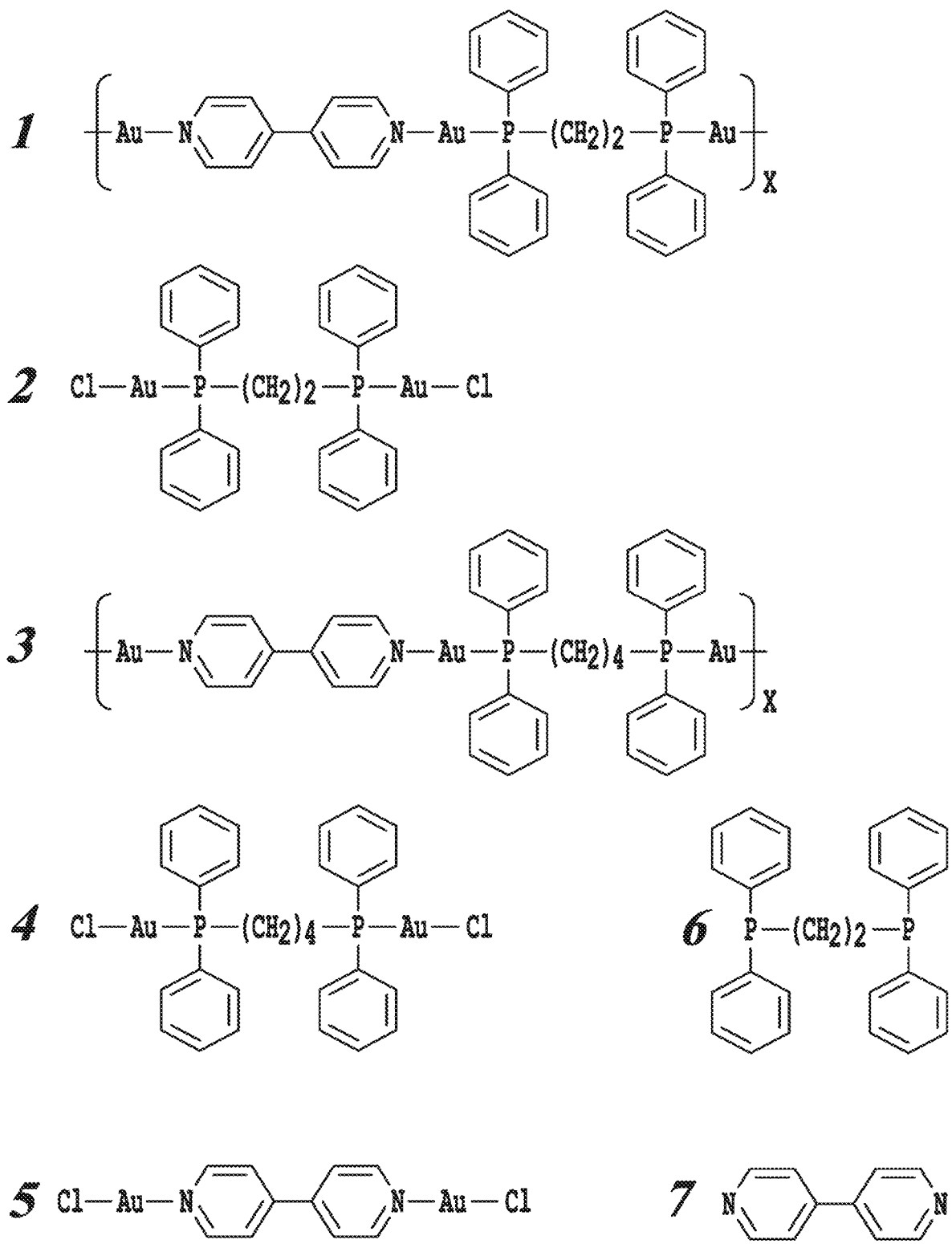
FIGS. 16A-16B show structures of various preferred embodiments of gold complexes exhibiting XEOL.
Figure 16B:
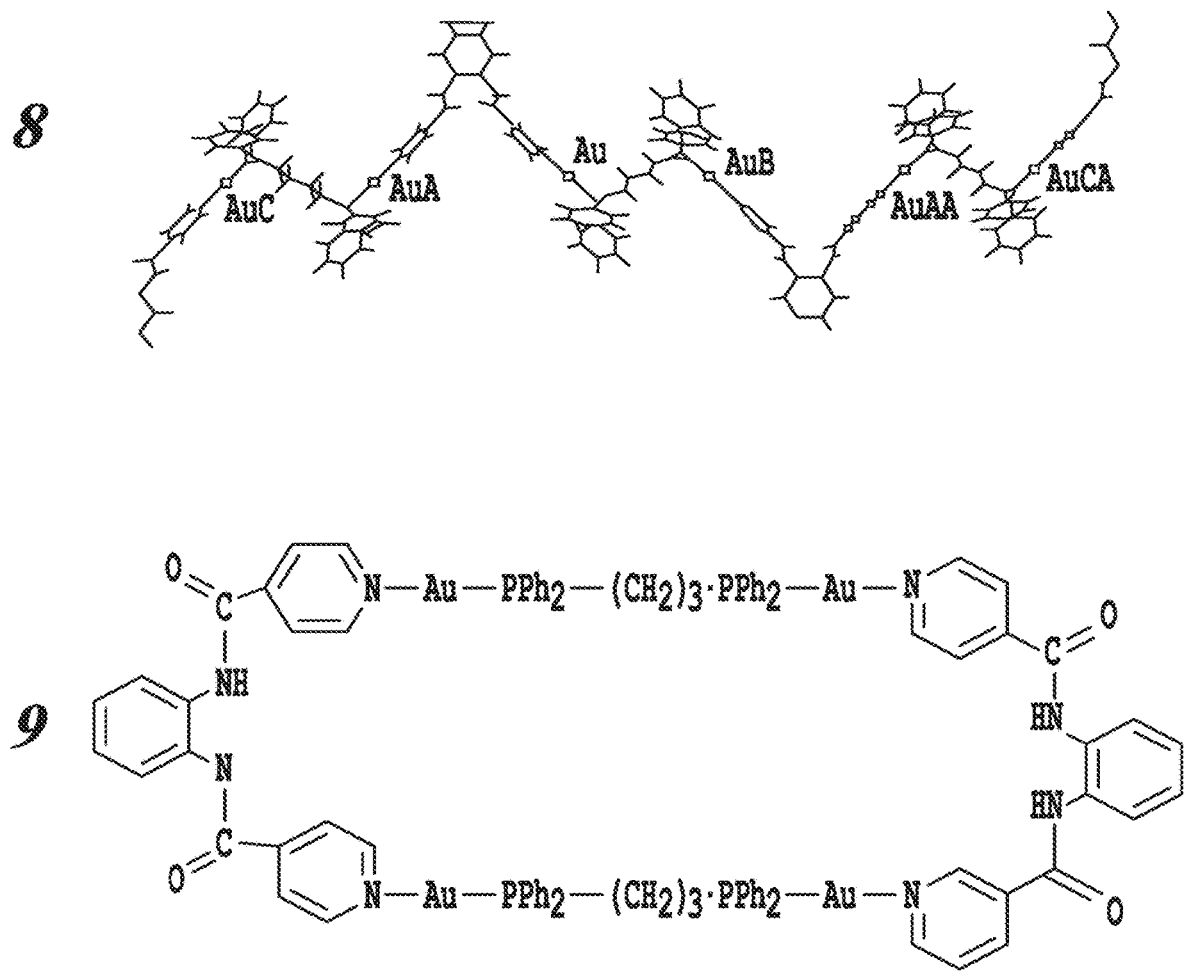
Figure 17:
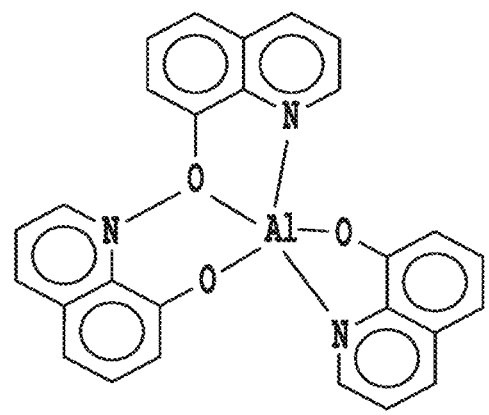
FIG. 17 shows the structure of a further embodiment of compound exhibiting XEOL, namely a tris-8-hydroxyquinoline-aluminum complex.

XEOL materials can include lanthanides or rare earth materials Some examples of metal complexes exhibiting XEOL which can be used as energy modulation agent systems are shown in FIGS. 16A-16B and 17. Such structures can be modified by replacing the metal atom with metal nanoparticles in order to fabricate a plasmonics-enhance PEPST probe. In the present invention, the experimental parameters including size, shape and metal type of the nano structure can be selected based upon the excitation radiation (NIR or X ray excitation), the photoactivation radiation (UVB), and/or the emission process from the energy modulation agent system (visible NIR).

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention.

Further materials suitable as energy modulation agents include, but are not limited to, CdTe, CdSe, ZnO, CdS, $Y_2O_3$, MgS, CaS, SrS and BaS. Such materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnSy$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}By$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional energy modulation materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, ... $0<z<1$, $o<q<1$). Further materials suitable as energy modulation agents include $LaPO_4$: Ce, Tb and $3Ca_3(PO_4)_2$ $Ca(Fl, Cl)_2:Sb^{3+}$, $Mn^{2+}$.

Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er3^+$; $ZnS:Mn^{2+}$; $ZnS:Mn,Er^{3+}$ are known in the art to function for both down-conversion luminescence and upconversion luminescence, and can thus be used in various embodiments of the present invention.

These and the other energy modulation agents described herein can be coated with a passivation or biocompatible material to protect it from its environment (e.g., the biological medium of a human or animal body) and vice versa to protect its environment from the energy modulation agent. In some embodiments, the biocompatible material is a biocompatible, non-toxic layer as shown in FIG. 34. In some embodiments, the biocompatible material covering the energy modulation agents is a biocompatible polymer that can form a nanocap. The biocompatible material can be a gel or biocompatible polymer. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers.

Figure 37:
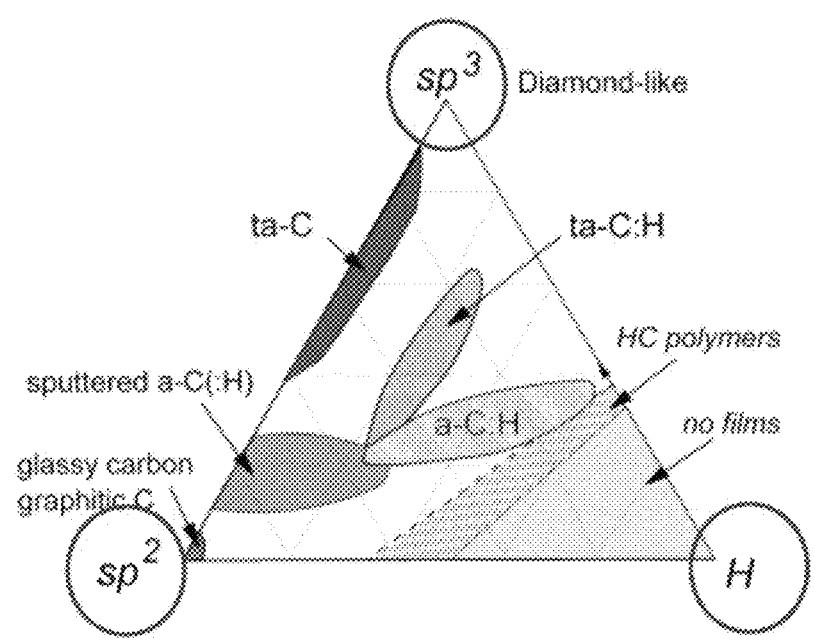
FIG. 37 is a representative phase diagram of a diamond like carbon coating material.

In some embodiments, the biocompatible material can be nano-diamond film or diamond like carbon coating or a highly conductive graphene material. A wide variety of diamond like carbon (DCL) coating materials are known in the art, ranging in $sp^3$ to $sp^2$ concentrations and including a variety of dopants or impurities, especially hydrogen. The range of $sp^3$ to $sp^2$ concentrations and the concentration of dopants or impurities influences the optical, electrical, and mechanical properties of the resulting DLC coating. In the literature, the phase diagram in FIG. 37 is representative.

As demonstration, a variety of these DLC materials for their compatibility as a biocompatible coating and suitable UV transmittance. There appears to be a wide diversity of thicknesses and ranges of H concentration and $sp^3$ to $sp^2$ concentrations, which are suitable here as a coating.

Figure 36:
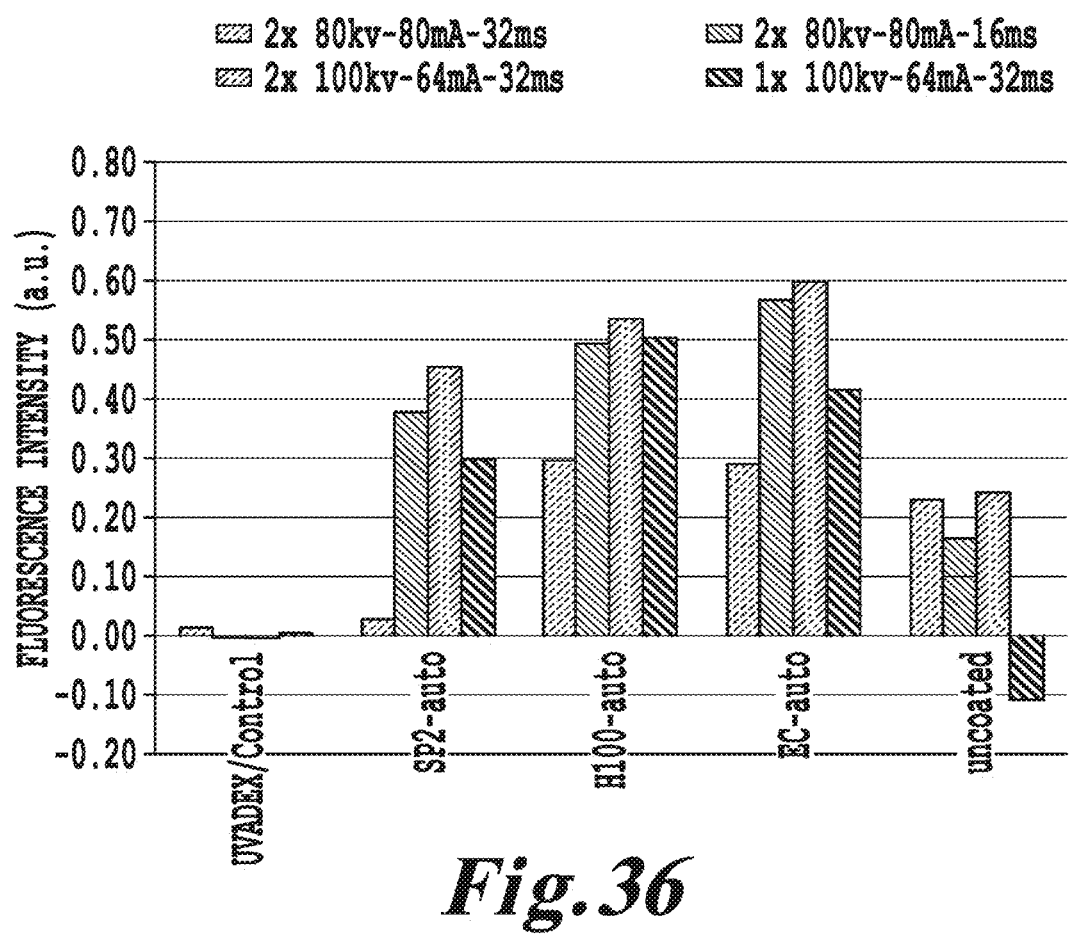
FIG. 36 is a plot of relative cell kill using various coatings on a mixture of two phosphors compared to a control sample having no phosphor.

In one example, a mixture of two phosphors ($LaPO_4$: Ce, Tb and $3Ca_3 (PO_4)_2$ $Ca(Fl, Cl)_2:Sb^{3+}$, $Mn^{2+}$) were coated with ethyl cellulose (EC), coated with a predominantly $sp^2$ DLC (SP2), and were coated with an hydrogenated DLC film (H100). FIG. 36 is a plot of relative cell kill using the various coatings as compared to a control sample having no phosphor. The results show that all of these films had a substantially high fraction of cell kill when exposed to x-ray irradiation at the x-ray peak voltage sand currents listed. On average, all the coated samples seemed to have a higher fractional cell kill than the uncoated phosphors, indicating that the coatings did not substantially obscure the emitted light from the phosphors.

Diamond and Diamond-Like Carbon Energy Modulation Agents

The use of a diamond material (diamond crystals, nano-diamond films, or micron to sub-micron size diamond particles or DLC) as an energy modulation agent is also possible in the present invention.

U.S. Pat. No. 7,927,390 (the entire contents of which are incorporated herein by reference) describes aqueous suspensions of finely divided diamond particles which would be suitable sources of diamond for the present invention. As noted therein, these suspensions could be for example an aqueous suspension liquid of finely divided diamond particles comprising 0.05 to 160 parts by weight of a finely divided diamond particles in 1000 parts of water, with the finely divided diamond particles having an element composition consisting mainly of 72 to 89.5% by weight of carbon, 0.8 to 1.5% of hydrogen, 1.5 to 2.5% of nitrogen, and 10.5 to 25.0% of oxygen. These diamond particles would have diameters in the range of 2 nm to 50 nm in diameters thereof (80% or more by number average, 70% or more by weight average). although larger and smaller diamond particles could be used.

U.S. Pat. No. 5,087,434 (the entire contents of which are incorporated herein by reference) describes compositions of synthetic diamond particles and their synthesis by homogeneous nucleation of seed particles in the gas phase followed by growth of diamond or diamond-like carbon on these seeds. The techniques and diamond particles used in this patent are applicable here for the energy modulation agents of this invention.

Presently fluorescent nanodiamond particles are commercially available from Adamas Nanotechnologies, Inc. of Raleigh, N.C. These materials are suitable for the diamond based energy modulation agents of this invention. The fluoresence of nanodiamond particles is based on color centers incorporated into the diamond lattice. Nitrogen-vacancy centers (N-V) provide red fluorescence and N-V-N (or H3 centers) emit green light. These nanodiamond particles are biocompatibile, permit large diamond surface area (per volume), and permit surface functionalization.

NV centers in ND can be in a number of ways. In on approach, NDs manufactured by static high-pressure, high-temperature (HPHT) synthesis and containing about 100 ppm of substitutional N, are irradiated with 40-keV He+ ions followed by annealing. See Chang, Y.-R. et al. *Nature Nanotechnology*, 2008, 3, 284, the entire contents of which are incorporated herein by reference.

Besides diamond, diamond like carbon is available. U.S. Pat. No. 6,265,068 (the entire contents of which are incorporated herein by reference) describes inorganic phosphor particles having a diamond-like carbon coating and the method of making these particles. In this patent, the inorganic phosphor particles were coated with a diamond-like carbon coating in a plasma system. The coatings and phosphors in that patent are suitable for coating the energy modulation agents of this invention. The coated phosphors of that patent would be suitable as energy modulation agents of this invention.

In various embodiments of this invention, diamond or diamond like carbon excited by deep UV light, x-rays, e-beams, and other energetic particles emits light in the ultraviolet and/or visible range which in turn excites the PA molecules or materials attached (e.g., tethered to) or removed from the diamond.

In early reports of visible luminescence, diamond was made to luminesce in a variety of ways including by irradiating with ultra-violet rays, cathode rays or X-rays or by the action of heat or friction. Workers reported that diamonds, which fluoresced blue in ultra-violet rays, also fluoresced blue in X-rays; but the color in X-rays had less of a violet color. Workers also reported that diamonds not emitting diamonds under UV exposure, nevertheless luminesced under X-rays although weakly. In this invention, the use of ultra-violet rays, cathode rays or X-rays would be more preferred, than that of heat or friction.

Defects in the diamond and impurities in the diamond are known to affect the emitted wavelength. Known defects and/or dopants include nitrogen, boron, hydrogen, oxygen, silicon, phosphorus, nickel, cobalt, sulfur, manganese, tungsten, and iron. Of these, boron dopants can induce blue phosphorescence under UV light exposure. Yellow and green emissions are possible with nickel impurities. A number of "intrinsic" defects (i.e., the displacement of carbon atoms from their normal crystallographic position) have also been recognized.

Figure 34H:
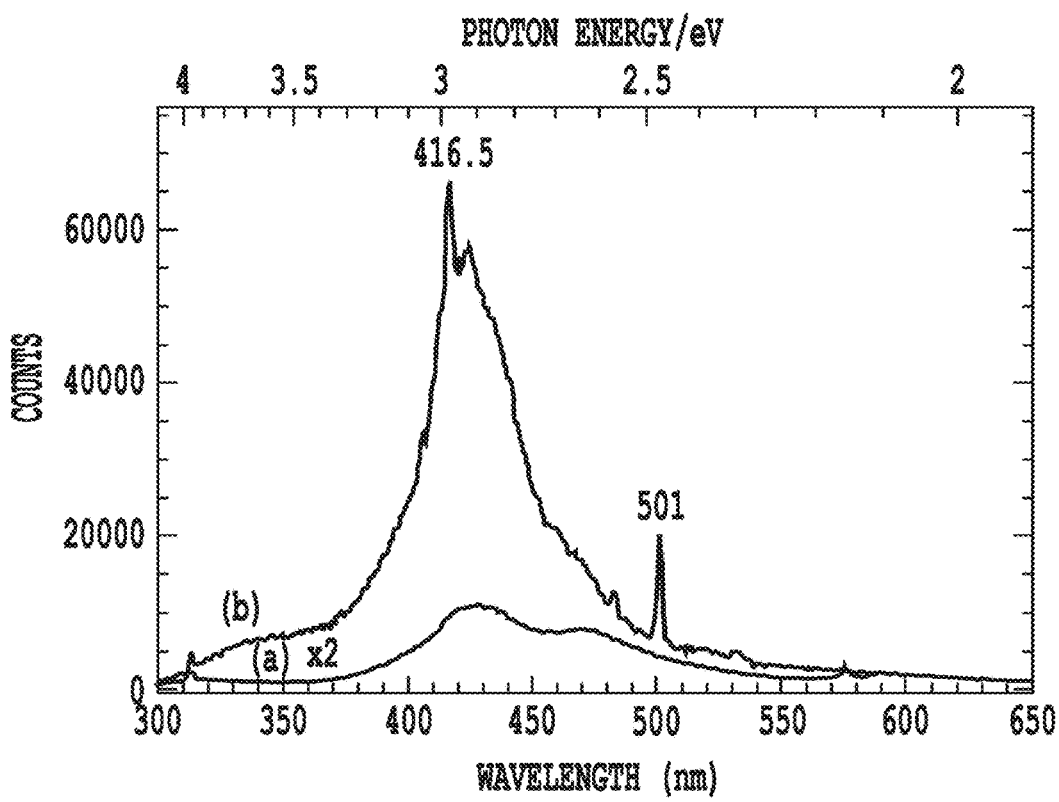
FIGS. 34H-34K show wavelength spectra from diamond or DLC-based materials.

With deep UV excitation at 223 nm, broad emissions are seen at about 428 and 470 nm, corresponding to photon energies 2.90 and 2.64 eV, respectively. As shown in FIG. 34H, the broad emissions extend into the ultraviolet.

Figure 34I:
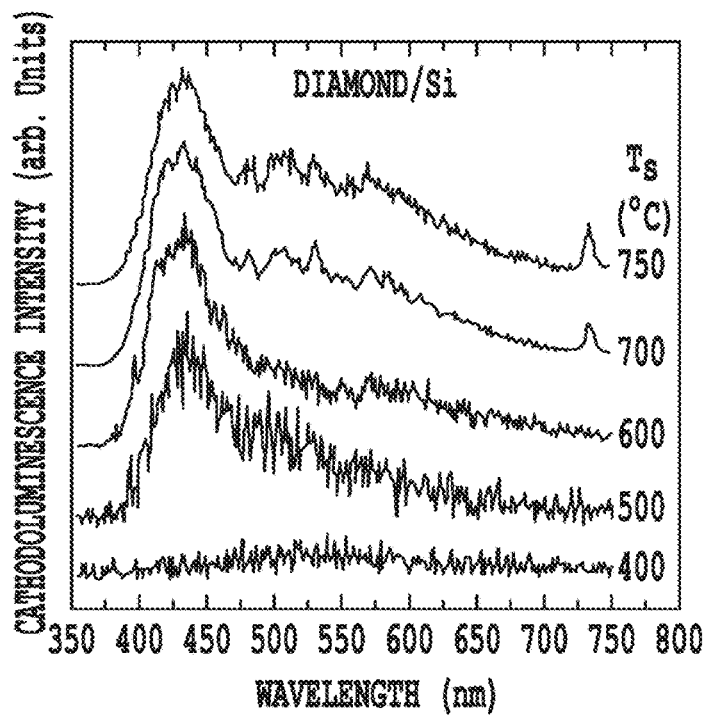
Figure 34J:
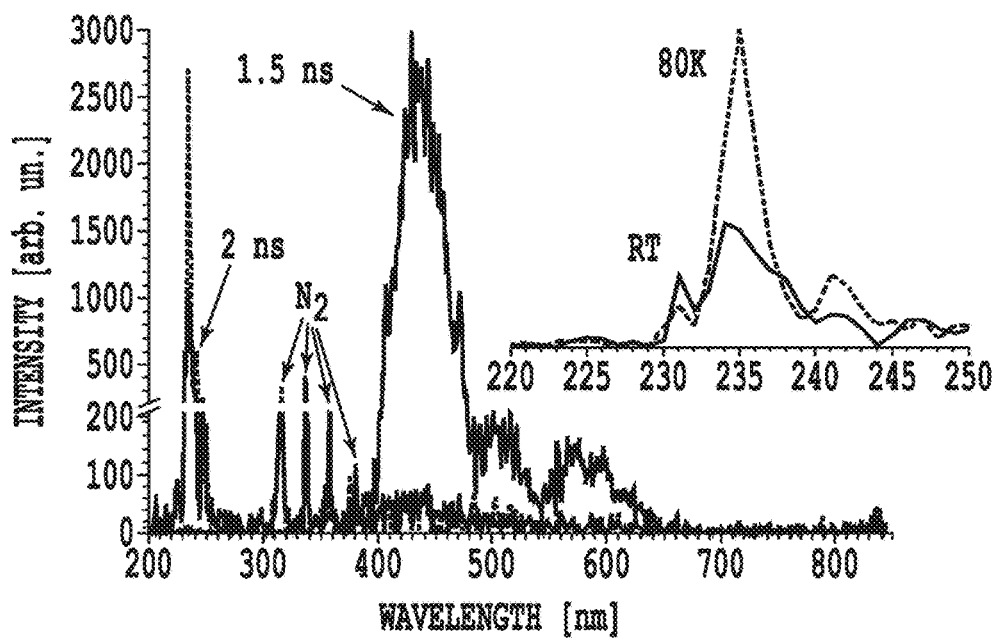
Figure 34K:
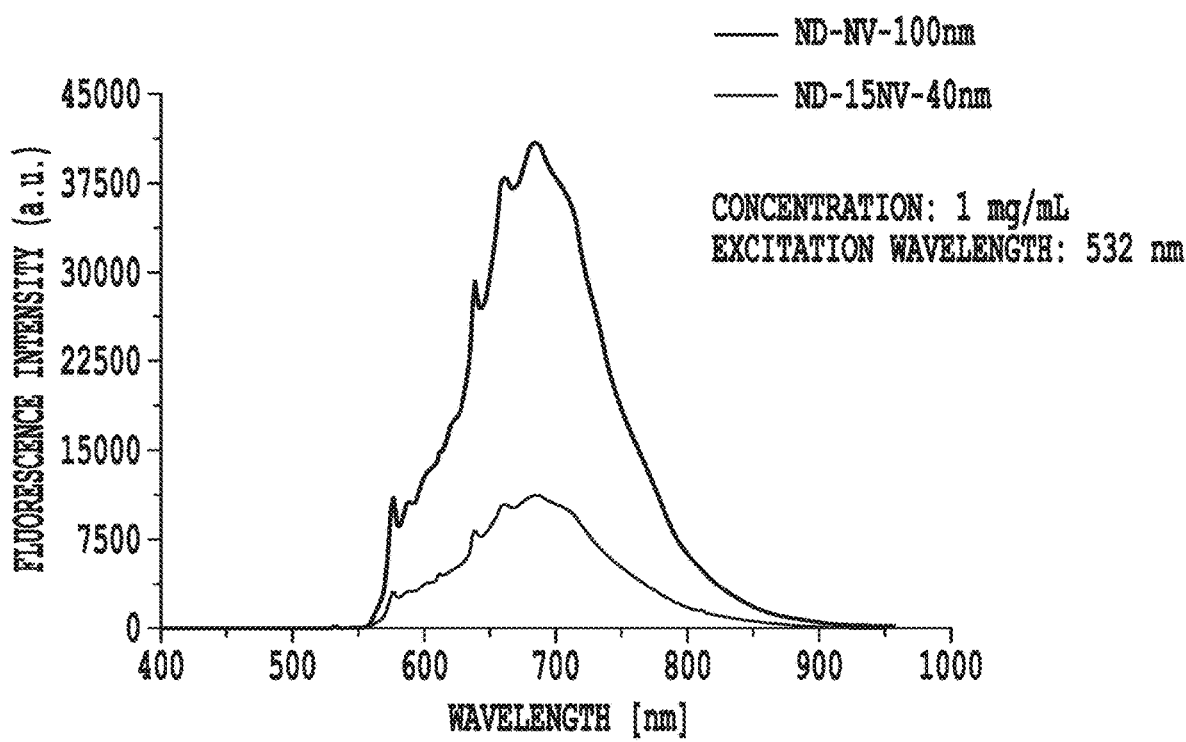

Similar emissions are observed for electron-induced or cathodoluminescence. The observed emissions are dependent on the dopants or impurities in the diamond. Under 20 kV electrons, a number of cathodoluminescent peaks have been observed. A dominant emission is observed at 430 nm and with several weak emissions occurring at 480, 500, 560, and 740 nm. The dominant emission is associated with a nearest neighbor donor acceptor recombination. The emission at 500 and 600 nm is associated with the nitrogen. The emission at 740 nm is associated with silicon. A representative set of spectra of chemical vapor deposited diamond is shown in FIG. 34I. FIG. 34J shows the luminescent spectra obtained from higher energy electron irradiation at 100 kV. A number of deep UV emissions in the 200 to 250 nm range were observed. The nanodiamonds discussed above from Adamas Nanotechnologies have prominent visible emissions depending on the dopant or impurity, and would be expected to have deep UV emission lines also. See FIG. 34K.

Besides the diamond discussed above, there have been reports of diamond-like carbon compounds also showing photoluminescence under deep UV 325 nm excitations. In particular, molybdenum-containing diamond-like carbon (Mo-DLC) thin films have been synthesized which have MoC nanocrystallites with sizes of 1-2 nm embedded in amorphous carbon cross-linked structures. These Mo-DLC films showed a photoluminescence (PL) band in blue with the PL peak divided into two bands with the peak positions at about 405 and 455 nm.

Thus, in various embodiments of the invention, diamond or diamond-like carbon materials can be used as both a coating on the other energy modulation agents or separately as the primary energy modulation agent. For example, the quantum dots noted above can be coated or decorated with diamond or diamond-like carbon material.

In a further embodiment, a diamond or diamond-like carbon material can be used as the energy modulation agent, such that the diamond or diamond-like carbon material has a plurality of defect types present in the same material, such that upon excitation, a single material emits multiple wavelengths of light. Alternatively, a plurality of diamond or diamond-like carbon materials can be used as energy modulation agents, such that the plurality of materials each have different defects present than the other of the plurality of materials, enabling the fine tuning of light emissions in a plurality of wavelengths as desired. This provides the capability to configure unique energy modulation agents where excitation (by electrons, x-rays, or deep UV) of the composite diamond or diamond-like carbon material on or in the presence of others of the energy modulation agents noted above such that a plurality of distinct wavelengths can be emitted from the composite structure. In one embodiment, emissions from either of the diamond or diamond-like carbon material and/or the non-diamond energy modulation agent can produce secondary emissions from each other. In one embodiment, emissions from either of the diamond or diamond-like carbon material and/or the non-diamond energy modulation agent can photoactivate drugs or other agents in the medium about the composite.

Principle of Plasmonics-Enhancement Effect of the PEPST Probe Using X-Ray Excitation One embodiment of the basic PEPST probe embodiment comprises PA molecules bound to an energy modulation agent and to plasmonic metal (gold) nanoparticles. First the metal nanoparticle can serve as a drug delivery platform (see previous discussion). Secondly, the metal nanoparticle can play 2 roles:

(1) Enhancement of the X-ray electromagnetic field
(2) Enhancement of the emission signal of the energy modulation agent system.

The X ray radiation, used to excite the energy modulation agent system, is amplified by the metal nanoparticle due to plasmon resonance. As a result the energy modulation agent system exhibits more emission light that is used to photoactivate the PA drug molecules (e.g., psoralens) and make them photoactive. In this case the metal nanoparticles are designed to exhibit strong plasmon resonance at or near the X ray wavelengths. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes described above.

Figure 18:
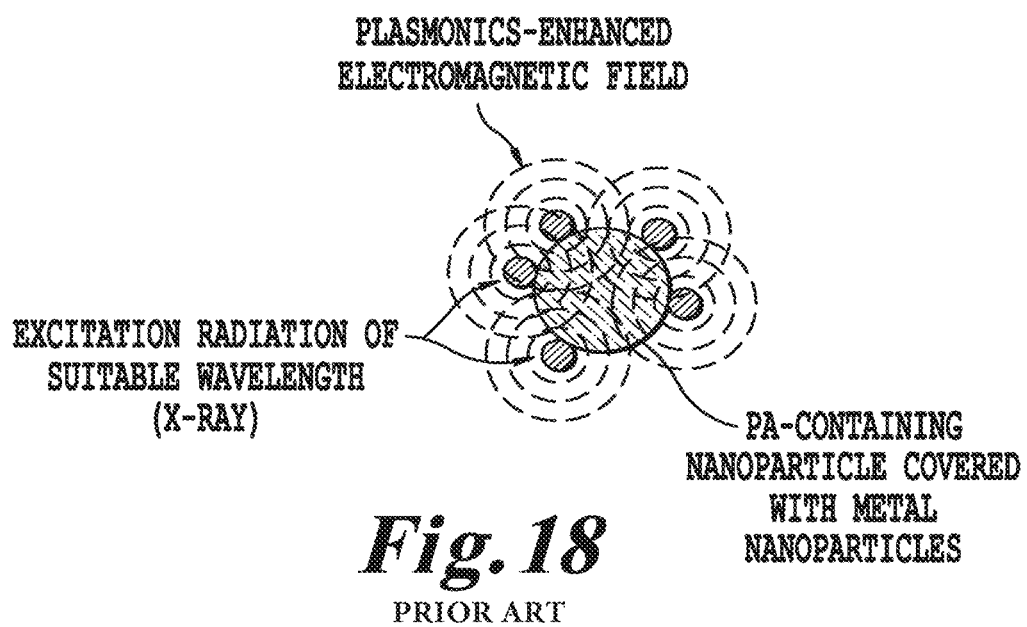
FIG. 18 is a graphical representation of a plasmonics-enhanced mechanism for a photo-active energy modulation agent-PA probe of the present invention.

FIG. 18 illustrates the plasmonics-enhancement effect of the PEPST probe. X-ray used in medical diagnostic imaging has photon energies from approximately 10 to 150 keV, which is equivalent to wavelengths range from 1.2 to 0.0083 Angstroms. [$\lambda$ (Angstrom)=12.4/E (keV)]. Soft X ray can go to 10 nm. The dimension of plasmonics-active nanoparticles usually have dimensions on the order or less than the wavelengths of the radiation used. Note that the approximate atomic radius of gold is approximately 0.15 nanometers. At the limit, for gold the smallest "nanoparticle" size is 0.14 nm (only 1 gold atom). A nanoparticle with size in the hundreds of nm will have approximately $10^6$-$10^7$ gold atoms. Therefore, the range of gold nanoparticles discussed in this invention can range from 1-$10^7$ gold atoms.

Figure 19:
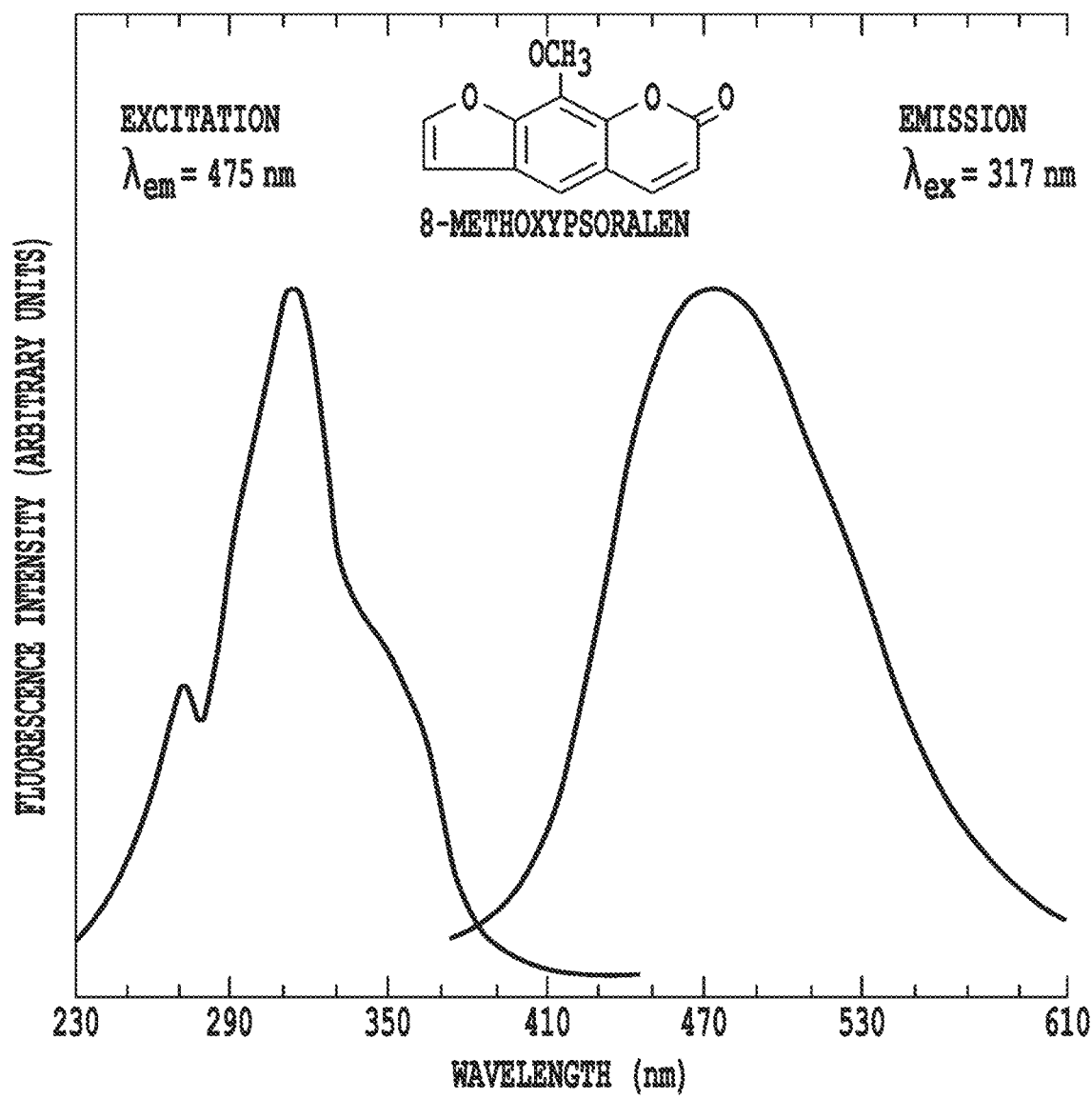
FIG. 19 is a graph showing excitation and emission fluorescence spectra of psoralens.

The gold nanoparticles can also enhance the energy modulation agent emission signal, which is use to excite the PA molecule. For psoralens, this spectral range is in the UVB region (320-400 nm). Silver or gold nanoparticles, nanoshell and nanocaps have been fabricated to exhibit strong plasmon resonance in this region. FIG. 19 shows excitation and emission fluorescence spectra of a psoralen compound (8-methoxypsoralen).

PEPST Energy Modulation Agent-PA Probe with Detachable PA.

Some photoactive drugs require that the PA molecule to enter the nucleus. FIGS. 20A-20C show an embodiment of a PEPST probe where the PA drug molecule is bound to the metal nanoparticles via a linker (FIG. 20A) that can be cut by photon radiation (FIG. 20B). Such a probe is useful for therapy modalities where the PA molecules have to enter the nucleus, e.g., psoralen molecules need to enter the nucleus of cells and intercalate onto DNA (FIG. 20C). Since it is more difficult for metal nanoparticles to enter the cell nucleus than for smaller molecules, it is preferable to use PEPST probes that have releasable PA molecules.

Suitable linkers for linking the PA drug molecule to the metal nanoparticles include, but are not limited to, labile chemical bonds that can be broken by remote energy excitation (from outside the body, e.g., MW, IR, photoacoustic energy, ultrasound energy, etc.), labile chemical bonds that can be broken by the chemical environment inside cells, antibody-antigen, nucleic acid linkers, biotin-streptavidin, etc.

Nanoparticle Chain for Dual Plasmonics Effect

FIG. 21 illustrates an embodiment of the present invention PEPST probe having a chain of metal particles having different sizes and coupled to each other, which could exhibit such dual plasmonics-based enhancement. For example the parameters (size, metal type, structure, etc) of the larger nanoparticle (FIG. 21, left) can be tuned to NIR, VIS or UV light while the smaller particle (FIG. 21, right) can be tuned to X ray. There is also a coupling effect between these particles.

These nanoparticle chains are useful in providing plasmonics enhancement of both the incident radiation used (for example, x-ray activation of CdS) as well as plasmonics enhancement of the emitted radiation that will then activate the PA.

Drug Delivery Platforms

Liposome Delivery of Energy Modulation Agent-PA Systems

The field of particle-based drug delivery is currently focused on two chemically distinct colloidal particles, liposomes and biodegradable polymers. Both delivery systems encapsulate the active drug. The drug is released from the particle as it lyses, in the case of liposomes, or disintegrates, as described for biodegradable polymers. One embodiment of the present invention uses liposomal delivery of energy modulation agent-PA systems (e.g., gold nanoshells) for therapy. An exemplary embodiment is described below, but is not intended to be limiting to the specific lipids, nanoparticles or other components recited, but is merely for exemplary purposes:

Preparation of Liposomes. The liposome preparation method can be adapted from Hölig et. al Hölig, P., Bach, M., Volkel, T., Nande, T., Hoffmann, S., Müller, R., and Kontermann, R. E., *Novel RGD lipopeptides for the targeting of liposomes to integrin-expressing endothelial and melanoma cells*. Protein Engineering Design and Selection, 2004. 17(5): p. 433-441]. Briefly, the lipids PEG-DPPE, PC, and Rh-DPPE are mixed in chloroform in a round bottom flask and evaporated (Hieroglyph Rotary Evaporator, Rose Scientific Ltd., Edmonton, Alberta, Canada) to eliminate chloroform. The dry film is dehydrated into aqueous phase with using PBS solution. A dry lipid film is prepared by rotary evaporation from a mixture of PC, cholesterol, and PEG-DPPE and then hydrated into aqueous phase using PBS. The mixture is vigorously mixed by overtaxing and bath solicited (Instrument, Company) and the suspension extruded through polycarbonate filter using Liposofast apparatus (Avestin Inc., Ottawa, ON, Canada) (pore-size 0.8 µm). Preparation of liposomes is performed as follows; 0.1 mmol of PC is dispersed in 8 ml of chloroform and supplemented with 0.5 mol of PEG-DPPE in 20 ml of chloroform. 0.3 mmol rhodamine-labeled phosphatidylethanolamine (Rh-DPPE) is then incorporated into the liposomes. The organic solvents are then removed by rotary evaporation at 35° C. for 2 h leaving a dry lipid film. Gold nanoshells are encapsulated into liposomes by adding them to the PBS hydration buffer and successively into the dry lipid film. This mixture is emulsified in a temperature controlled sonicator for 30 minutes at 35° C. followed by vortexing for 5 min. Encapsulated gold nanoshells are separated from unencapsulated gold nanoshells by centrifugation for 5 minutes at 2400 r.p.m (1200 g). The resulting multilamellar vesicles suspension is extruded through polycarbonate filter using Liposofast apparatus (Avestin Inc., Ottawa, ON, Canada) (pore-size 0.8 µm). The aqueous mixture is obtained and stored at 4° C.

Fabrication of Gold Nanoparticles: The Frens method [Frens, G., *Controlled nucleation for the regulation of the particle size in monodisperse gold solutions*. Nature (London) Phys Sci, 1973. 241: p. 20-22] can be used in the present invention to synthesize a solution of gold nanoparticles ranging in diameter from 8-10 nm. Briefly, $5.0 \times 10^{-6}$ mol of $HAuCl_4$ is dissolved in 19 ml of deionized water producing a faint yellowish solution. This solution is heated with vigorous stirring in a rotary evaporator for 45 minutes. 1 ml of 0.5% sodium citrate solution is added and the solution is stirred for an additional 30 minutes. The color of the solution gradually changed from the initial faint yellowish to clear, grey, purple and finally a tantalizing wine-red color similar to merlot. The sodium citrate used serves in a dual capacity, first acting as a reducing agent, and second, producing negative citrate ions that are adsorbed onto the gold nanoparticles introducing surface charge that repels the particles and preventing nanocluster formation.

Preparation and Internalization of Liposome-Encapsulated Gold Nanoshells:

Liposome-encapsulated gold nanoshells are incubated with MCF-7 cells grown on partitioned cover-slips for intracellular delivery. This is done by adding 10 µl of liposome-encapsulated gold nanoshells per 1 ml of cell culture medium. This is incubated for 30 minutes in a humidified (86% RH) incubator at 37° C. and 5% CO2. This cell is used for localization studies; to track the rhodamine-DPPE-labeled liposomes into the cytoplasm of the MCF-7 cell. After incubation, the cells grown on cover-slips are washed three times in cold PBS and fixed using 3.7% formaldehyde in PBS. Rhodamine staining by rhodamine-DPPE-labeled liposomes is analyzed using a Nikon Diaphot 300 inverted microscope (Nikon, Inc., Melville, N.Y.).

Use of Ferritin and Apoferritin as Targeted Drug Delivery

Another embodiment to deliver the energy modulation agent-PA drugs involves the use of ferritin and apoferritin compounds. There is increasing interest in ligand-receptor-mediated delivery systems due to their non-immunogenic and site-specific targeting potential to the ligand-specific bio-sites. Platinum anticancer drug have been encapsulated in apoferritin. Ferritin, the principal iron storage molecule in a wide variety of organisms, can also be used as a vehicle for targeted drug delivery. It contains a hollow protein shell, apoferritin, which can contain up to its own weight of hydrous ferric oxide-phosphate as a microcrystalline micelle. The 24 subunits of ferritin assemble automatically to form a hollow protein cage with internal and external diameters of 8 and 12 nm, respectively. Eight hydrophilic channels of about 0.4 nm, formed at the intersections of subunits, penetrate the protein shell and lead to the protein cavity. A variety of species such as gadolinium ($Gd^{3+}$) contrast agents, desferrioxamine B, metal ions, and nanoparticles of iron salts can be accommodated in the cage of apoferritin. Various metals such as iron, nickel, chromium and other materials have been incorporated into apoferritin. Zinc selenide nanoparticles (ZnSe NPs) were synthesized in the cavity of the cage-shaped protein apoferritin by designing a slow chemical reaction system, which employs tetraaminezinc ion and selenourea. The chemical synthesis of ZnSe NPs was realized in a spatially selective manner from an aqueous solution, and ZnSe cores were formed in almost all apoferritin cavities with little bulk precipitation.

A simple method for synthesizing gold nanoparticles stabilized by horse spleen apoferritin (HSAF) is reported using $NaBH_4$ or 3-(N-morpholino)propanesulfonic acid (MOPS) as the reducing agent [Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, Vol. 101, 1719-1729, 2007]. Gold sulfite ($Au_2S$) nanoparticles were prepared in the cavity of the cage-shaped protein, apoferritin. Apoferritin has a cavity, 7 nm in diameter, and the diameter of fabricated $Au_2S$ nanoparticles is about the same size with the cavity and size dispersion was small. [Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, Vol. 35 (2006), No. 10 p. 1192]. Thus, in one embodiment, the PA or energy modulation agent-PA compounds are encapsulated inside the apoferrtin shells.

Use of Ferritin and Apoferritin as Enhanced Targeting Agents

It was reported that ferritin could be internalized by some tumor tissues, and the internalization was associated with the membrane-specific receptors. Previous studies have shown that ferritin-binding sites and the endocytosis of ferritin have been identified in neoplastic. Ferritin receptors have the potential for use in the delivery of anticancer drugs into the brain. In one embodiment, the present invention uses ferritin or apoferritin to both encapsulate PA and energy modulation agent-PA systems and also target tumor cells selectively for enhanced drug delivery and subsequent phototherapy. In this case no additional bioreactors are needed.

FIGS. 22A-22D schematically illustrate the use of encapsulated photoactive agents (FIG. 22A) for delivery into tissue and subsequent release of the photoactive drugs after the encapsulated systems enter the cell. Note the encapsulated system can have a bioreceptor for selective tumor targeting (FIG. 22B). Once inside the cell, the capsule shell (e.g., liposomes, apoferritin, etc.) can be broken (FIG. 22C) using non-invasive excitation (e.g., ultrasound, RF, microwave, IR, etc) in order to release the photoactive molecules that can get into the nucleus and bind to DNA (FIG. 22D).

Non-Invasive Phototherapy Using PEPST Modality

Figure 23B:
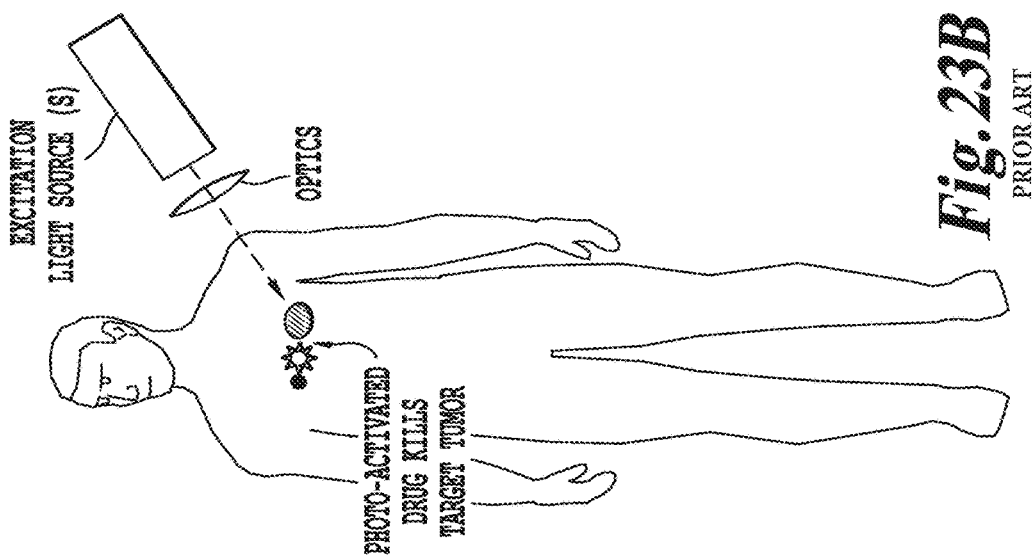
FIGS. 23A-23B are simplified graphical representations of the use of the present invention principle of non-invasive PEPSI modality.
Figure 23A:
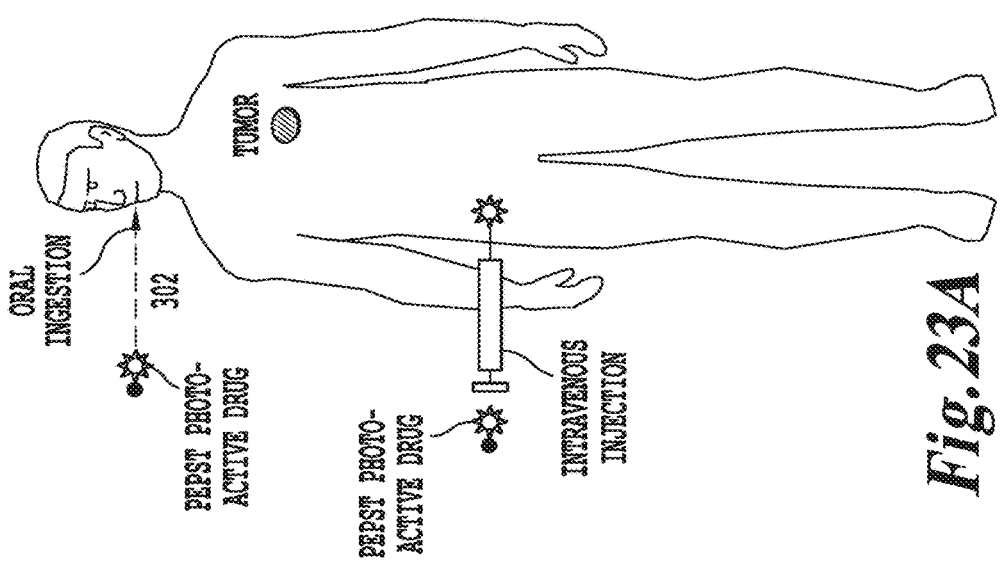

FIGS. 23A-23B illustrate the basic operating principle of the PEPST modality. The PEPST photoactive drug molecules are given to a patient by oral ingestion, skin application, or by intravenous injection. The PEPST drugs travel through the blood stream inside the body towards the targeted tumor (either via passive or active targeting strategies). If the disease is systematic in nature a photon radiation at suitable wavelengths is used to irradiate the skin of the patient, the light being selected to penetrate deep inside tissue (e.g., NIR or X ray). For solid tumors, the radiation light source is directed at the tumor. Subsequently a treatment procedure can be initiated using delivery of energy into the tumor site. One or several light sources may be used as described in the previous sections. One embodiment of therapy comprises sending NIR radiation using an NIR laser through focusing optics. Focused beams of other radiation types, including but not limited to X ray, microwave, radio waves, etc. can also be used and will depend upon the treatment modalities used.

Design, Fabrication and Operation of EIP Probes

Figure 25A:
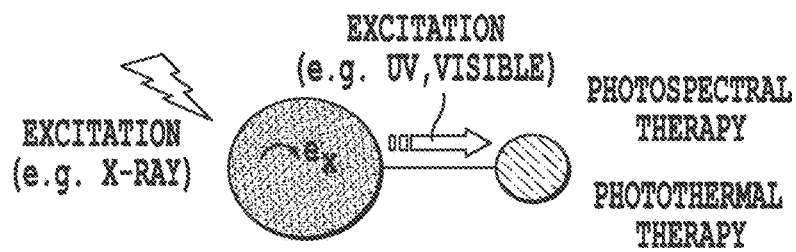
FIGS. 25A-25B show various schematic embodiments of basic EIP probes.
Figure 25B:
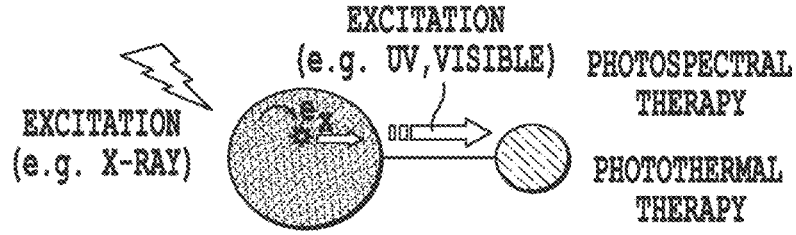
Figure 26A:
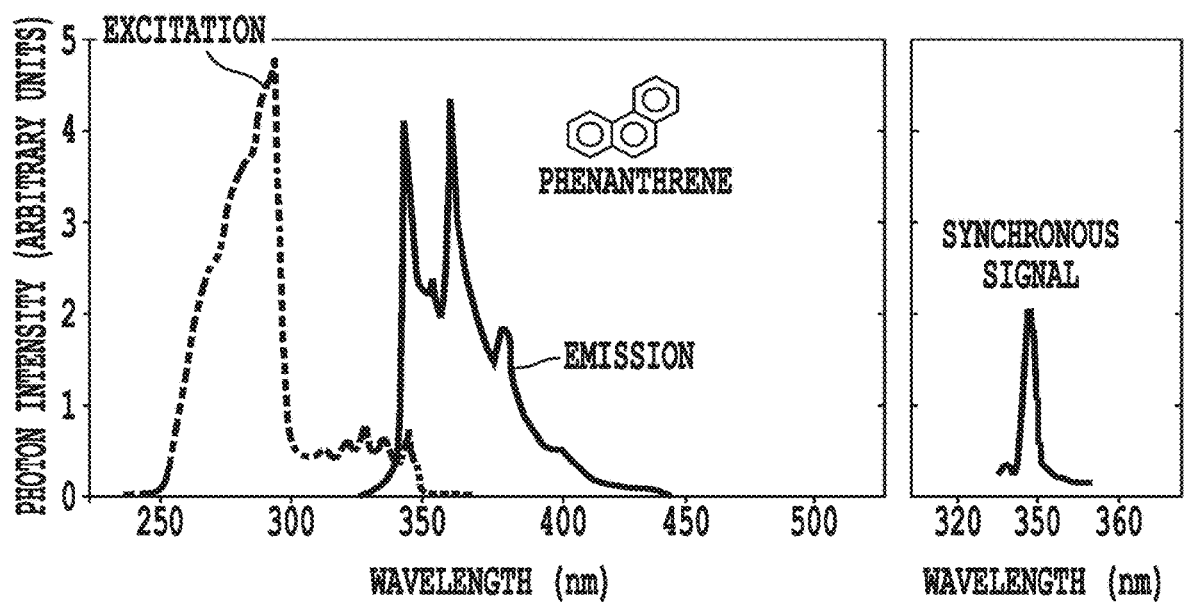
FIGS. 26A-26E are graphical representations of fluorescence spectra of PAH compounds.
Figure 26B:
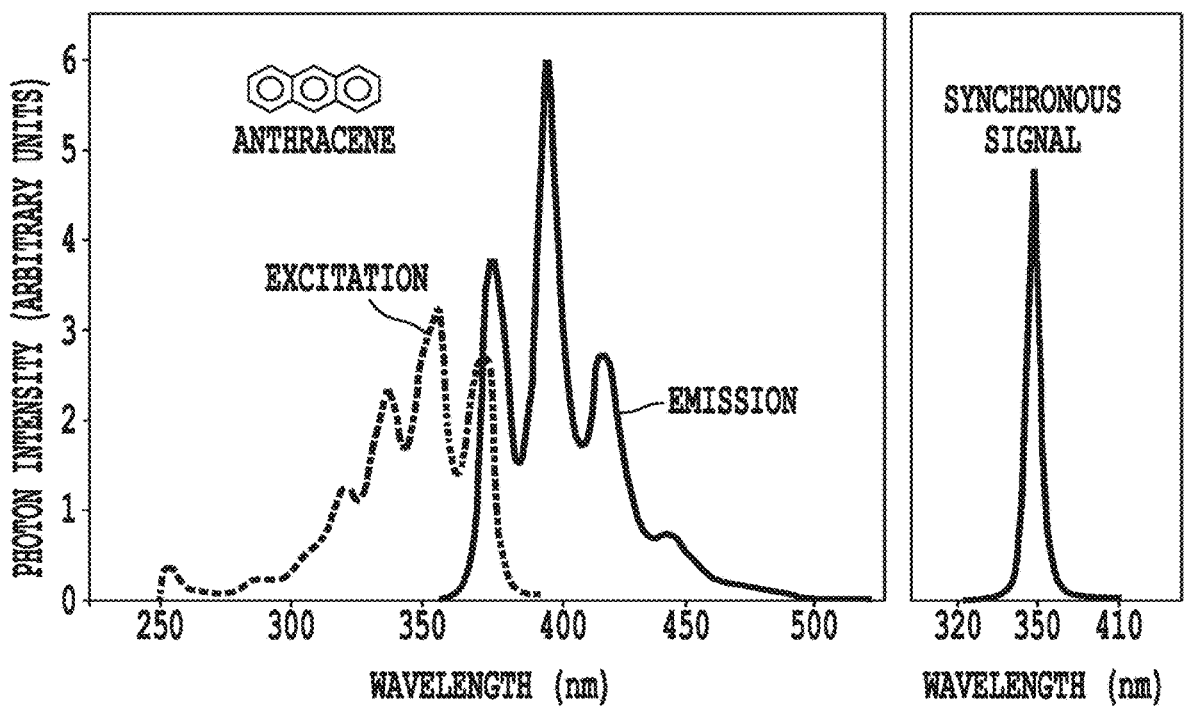
Figure 26C:
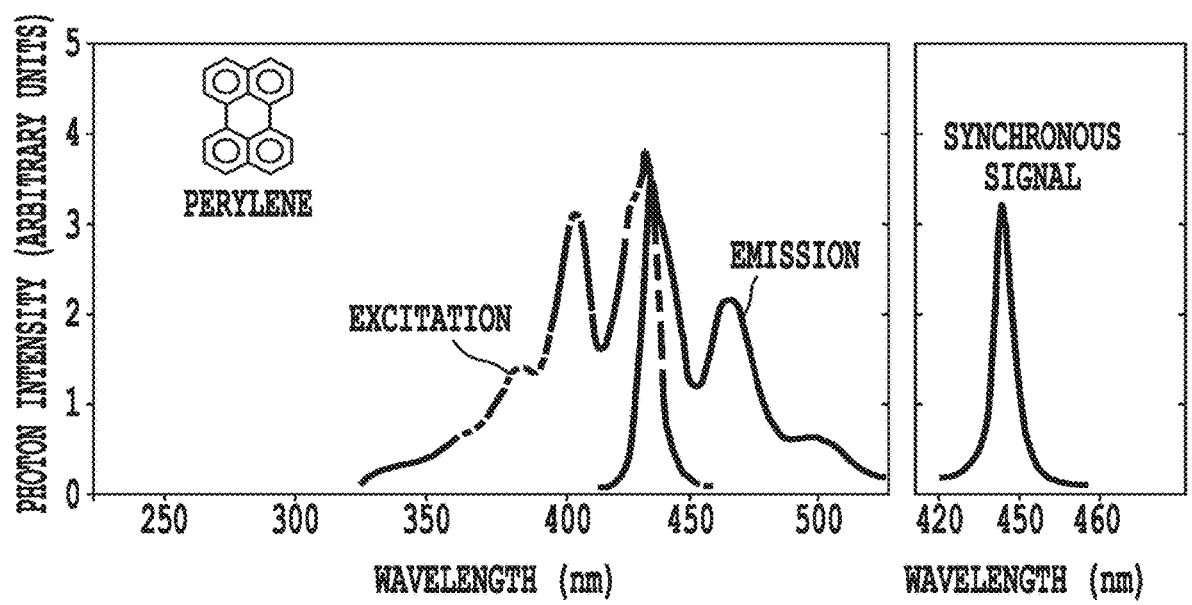
Figure 26D:
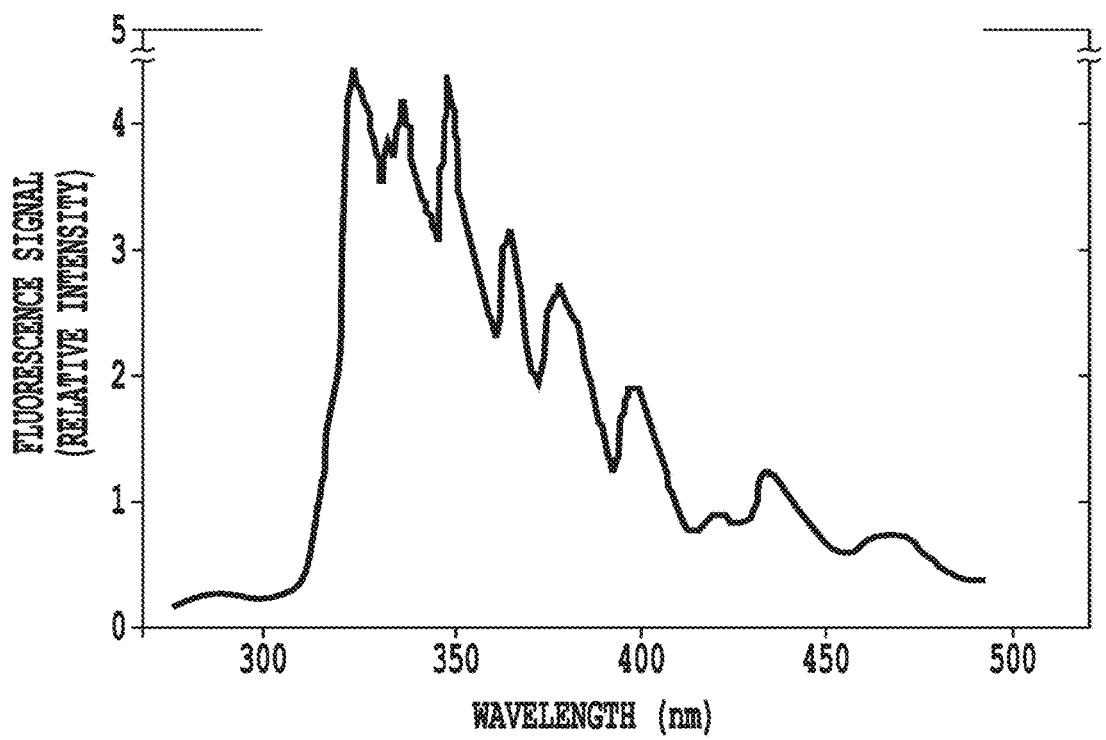
Figure 26E:
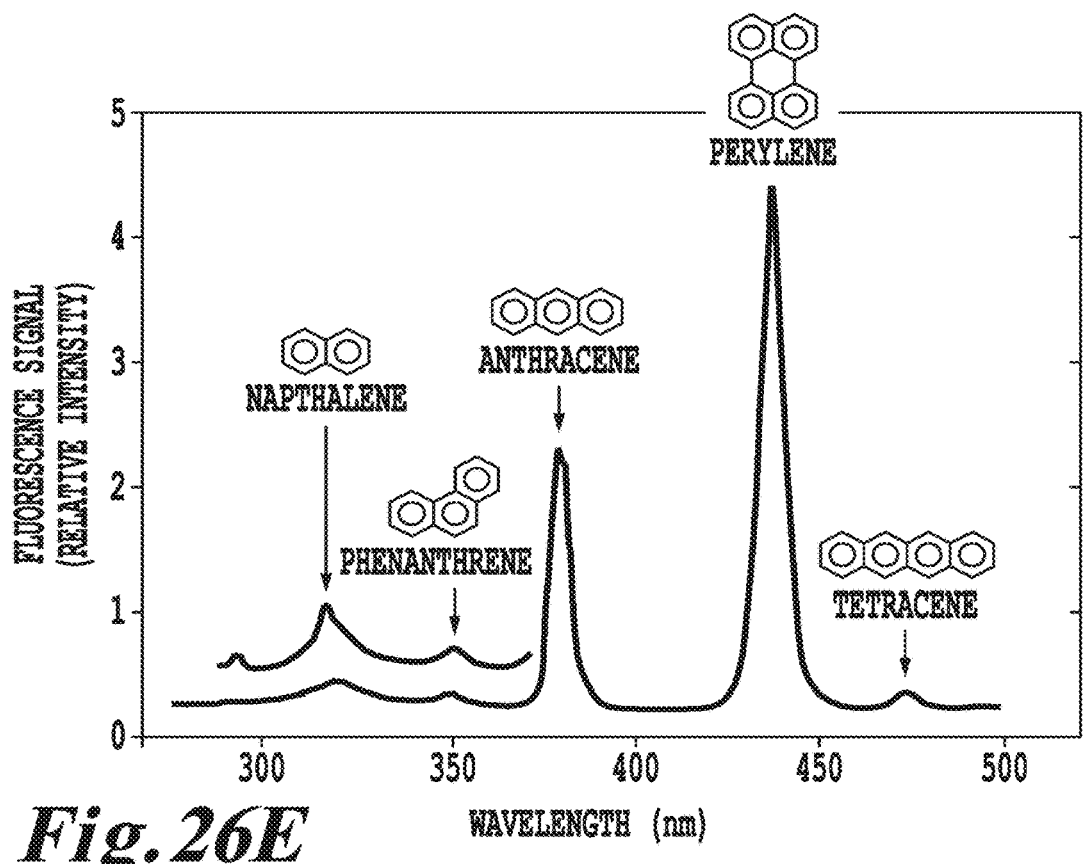

FIGS. 25A-25B show various embodiments of the EIP probes:

(A) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have structural defects that serve as traps for excitons.

(B) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have impurities or dopant molecules that serve as traps for excitons.

(C)

EIP Probes with Tunable Emission:

The embodiment in probes B provide the capability to tune the energy conversion from an X ray excitation source into a wavelength of interest to excite the PA molecules. In 1976, D'Silva et al demonstrated that polynuclear aromatic hydrocarbons (PAH) molecules doped in a frozen n-alkane solids could be excited by X-ray and produce luminescence at visible wavelengths characteristics of their luminescence spectra. [A. P. D'Silva, G. J. Oestreich, and V. A. Fassel, X-ray excited optical luminescence of polynuclear aromatic hydrocarbons, Anal. Chem.; 1976; 48(6) pp 915-917]. Tunable EIP probes can be designed to contain such luminescent dopants such as highly luminescent PAHs exhibiting luminescence emission in the range of 300-400 nm suitable to activate psoralen. A preferred embodiment of the EIP with tunable emission comprises a solid matrix (semiconductors, glass, quartz, conjugated polymers, etc) doped with naphthalene, phenanthrene, pyrene or other compounds exhibiting luminescence (fluorescence) in the 300-400 nm range [T. Vo-Dinh, *Multicomponent analysis by synchronous luminescence spectrometry*, Anal. Chem.; 1978; 50(3) pp 396-401]. See FIGS. 26A-26E. The EEC matrix could be a semiconductor material, preferably transparent at optical wavelength of interest (excitation and emission).

Figure 27:
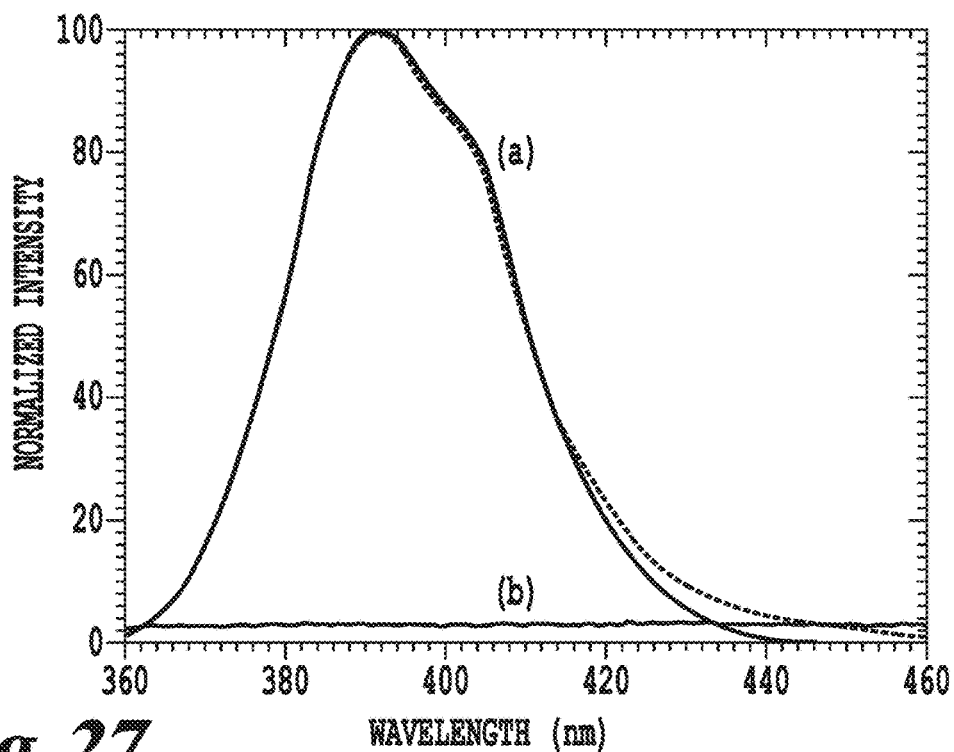
FIG. 27 is a graph showing the XEOL of Eu doped in BaFBr matrix.

Other dopant species such as rare earth materials can also be used as dopants. FIG. 27 shows the X ray excitation optical luminescence (XEOL) of Europium doped in a matrix of BaFBr, emitting at 370-420 nm. U.S. Patent Application Publication No. 2007/0063154 (hereby incorporated by reference) describes these and other nanocomposite materials (and methods of making them) suitable for XEOL.

Figure 28A:
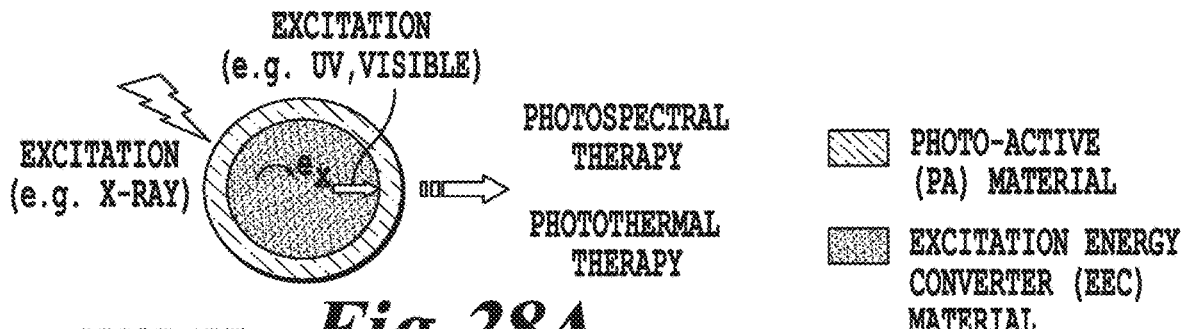
FIGS. 28A-28B provide further embodiments of schematic designs of EIP probes.
Figure 28B:
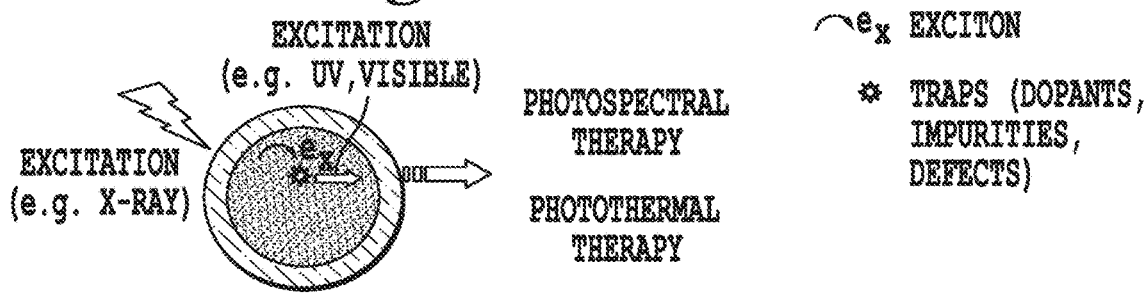

FIGS. 28A-28B show various embodiments of the EIP probes:

(A) probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials has structural defects that serve as traps for excitons.

(B) probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials have impurities or dopant molecules that serve as traps for excitons.

Design, Fabrication and Operation of EPEP Probes

Figure 29A:
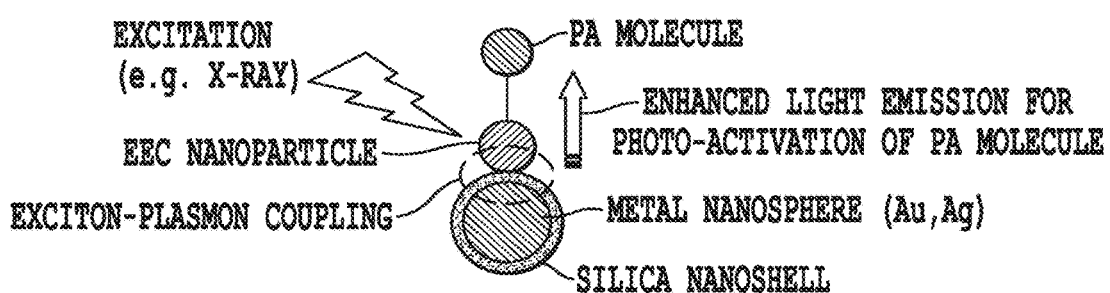
FIGS. 29A-29B are graphical representations of various embodiments of basic EPEP probes.
Figure 29B:
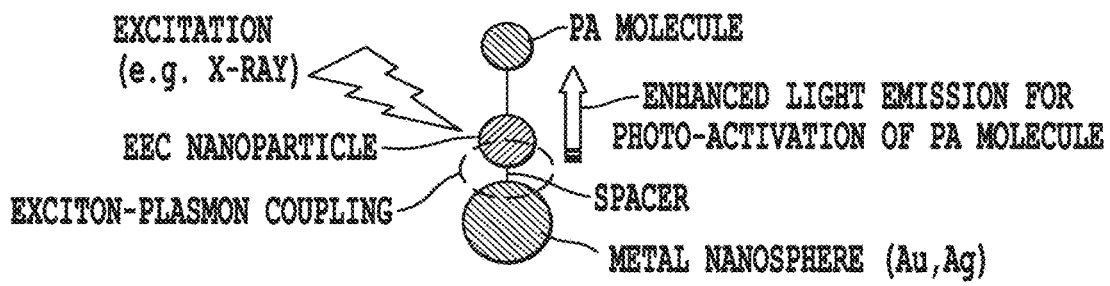

FIGS. 29A-29B show various embodiments of EPEP probes of the present invention showing the exciton-plasmon coupling:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle covered with a nanoshell of silica (or other dielectric material). The silica layer (or nanoshell) (see FIG. 24A and FIG. 24B; layer nanoshell in white between energy modulation material and metal nano structures) is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle via a spacer (linker). The spacer is designed to prevent quenching of the luminescence light emitted by the energy modulation agent particle excited by X-ray.

Figures 30A, 30B, 30C:
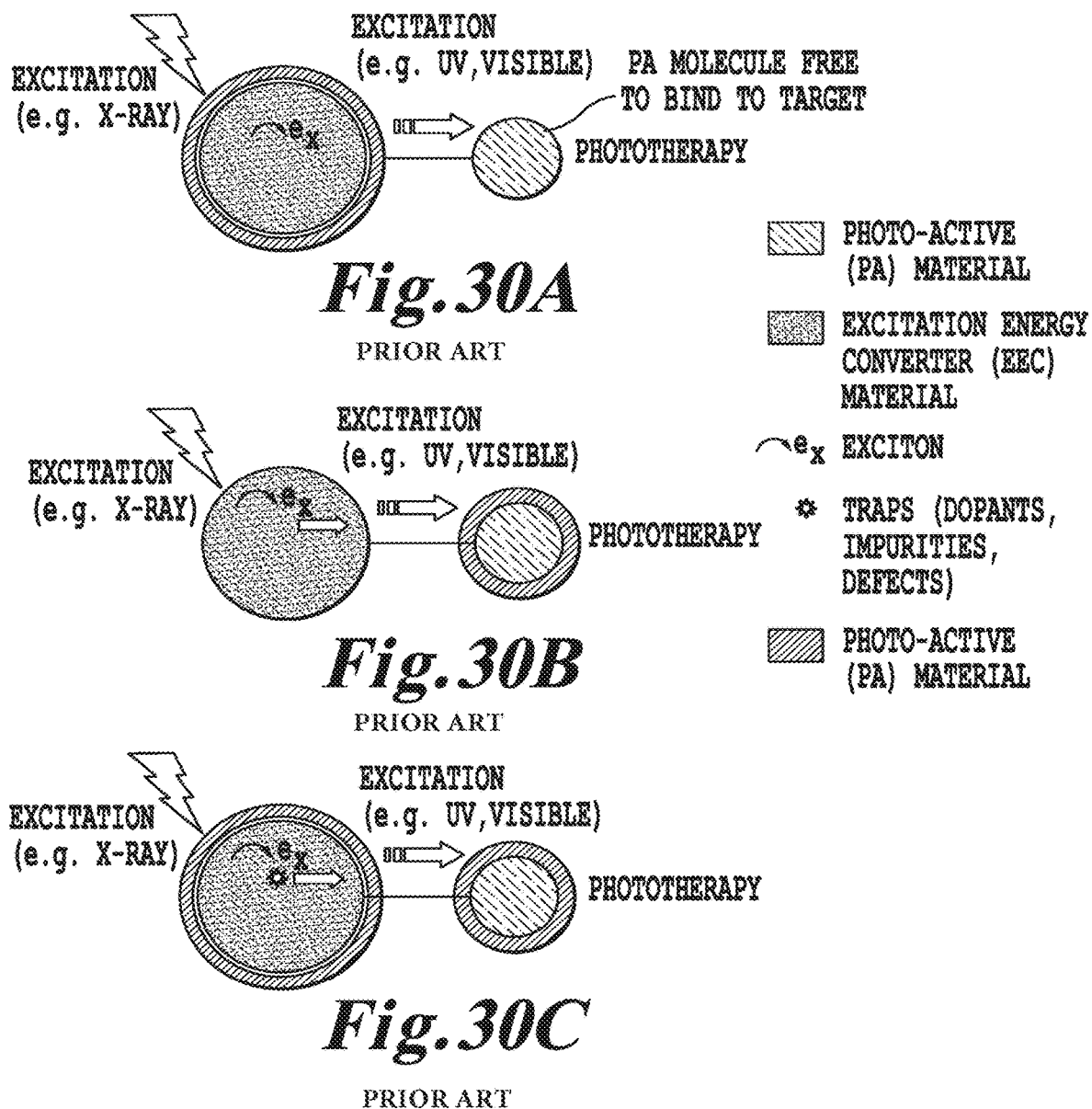
FIGS. 30A-30C are graphical representations of various embodiments of basic EPEP probes.

FIGS. 30A-30C show yet further embodiments of EPEP probes of the present invention:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of separate nanostructures (nano islands, nanorods, nanocubes, etc. . . . ) of metal (Au, Ag). The silica layer (or other dielectric material) is designed to prevent quenching of the luminescence light emitted by the EEC (also referred to as energy modulation agent) particle excited by X-ray. The metal nanostructures (Au, Ag, etc) are designed to induce plasmons that enhance the X ray excitation that subsequently leads to an increase in the EEC light emission, ultimately enhancing the efficiency of photoactivation, i.e. phototherapy. The structure of the nanoparticle can also be designed such that the plasmonics effect also enhance the energy modulation agent emission light. These processes are due to strong coupling between excitons (in the energy modulation agent materials and plasmons in the metal nanostructures).

(B) probe comprising a group of PA molecules in a particle bound (through a linker, which can be fixed or detachable) to an energy modulation agent particle that can produce excitons under radiative excitation at a suitable wavelength (e.g., X-ray). The PA-containing particle is covered with a layer of metallic nanostructures (Au, Ag). The metal nanostructures (Au, Ag, etc) are designed to induce plasmons that enhance the energy modulation agent light emission, ultimately enhancing the efficiency of photoactivation, i.e. phototherapy.

(C) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of metallic nanostructures (Au, Ag). The silica layer (or other dielectric material) is designed to prevent quenching of the luminescence light emitted by the energy modulation agent particle excited by X-ray. The metal nanostructures (Au, Ag, etc) are designed to induce plasmons that enhance the X ray excitation that subsequently leads to an increase in the energy modulation agent light emission, ultimately enhancing the efficiency of photoactivation, i.e. phototherapy. In addition. the PA-containing particle is covered with a layer of metallic nanostructures (Au, Ag). The metal nanostructures (Au, Ag, etc) are designed to induce plasmons that enhance the EEC light emission, ultimately enhancing the efficiency of photoactivation, i.e. phototherapy.

Hybrid EPEP Nano-Superstructures

EPEP probes can also comprise hybrid self-assembled superstructures made of biological and abiotic nanoscale components, which can offer versatile molecular constructs with a spectrum of unique electronic, surface properties and photospectral properties for use in phototherapy.

Figure 31A:
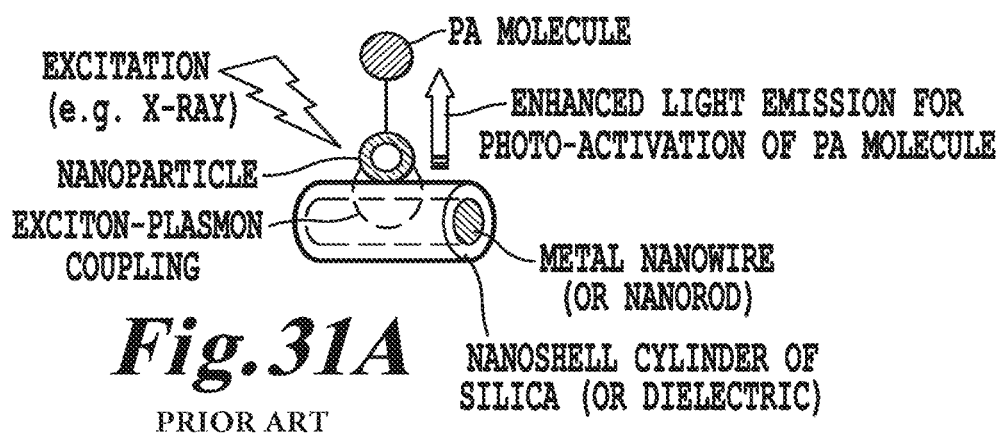
FIGS. 31A-31B are graphical representations of various embodiments of EPEP probes having NPs, NWs and NRs.
Figure 31B:
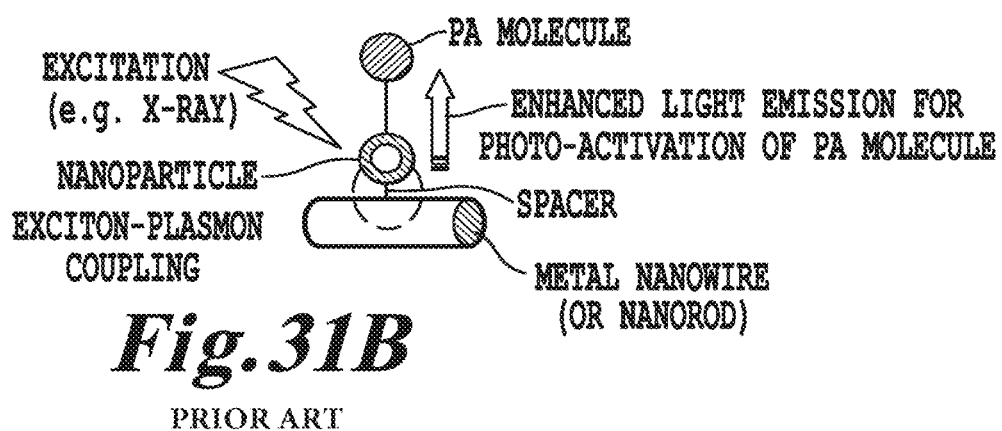

FIGS. 31A-31B show various embodiments of EPEP probes of the present invention comprising superstructures of NPs, NWs and NRs:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanowire (or nanorod) covered with a nanoshell cylinder of silica (or other dielectric material). The silica nanoshells cylinder is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect and/or the exciton-plasmon coupling (EPC) effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticles via a spacer (linker). The spacer is designed to prevent quenching of the luminescence light emitted by the energy modulation agent particle excited by X-ray. Same effect as above in (A)

Figure 32A:
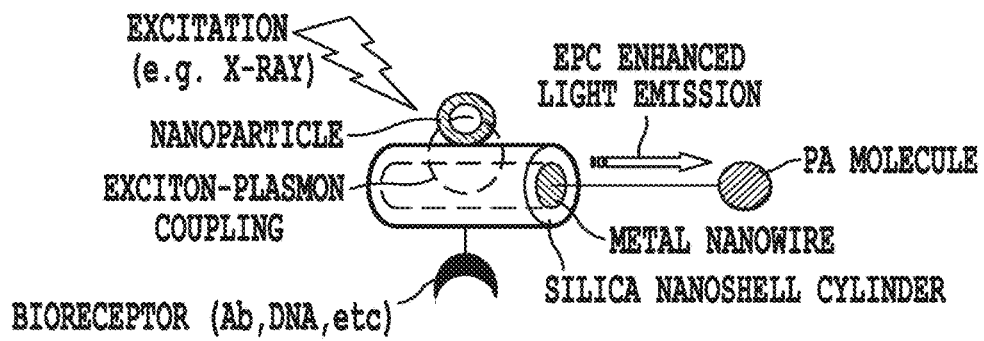
FIGS. 32A-32B are graphical representations of various embodiments of EPEP probes having NPs, NWs, NRs and bioreceptors.
Figure 32B:
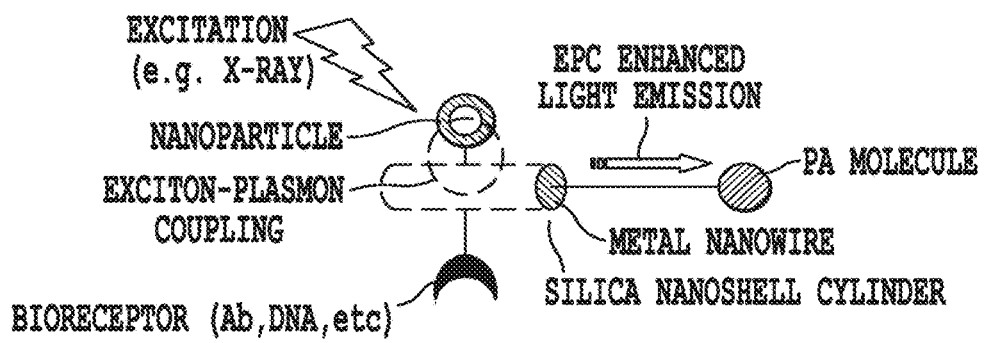

FIGS. 32A-32B show another set of embodiments of EPEP probes of the present invention comprising superstructures of NPs, NWs and NRs and bioreceptors (antibodies, DNA, surface cell receptors, etc.). The use of bioreceptors to target tumor cells has been discussed above in relation to PEPST probes. Note that in this embodiment the PA molecules are attached along the NW axis in order to be excited by the emitting light form the NWs.

Figure 33:
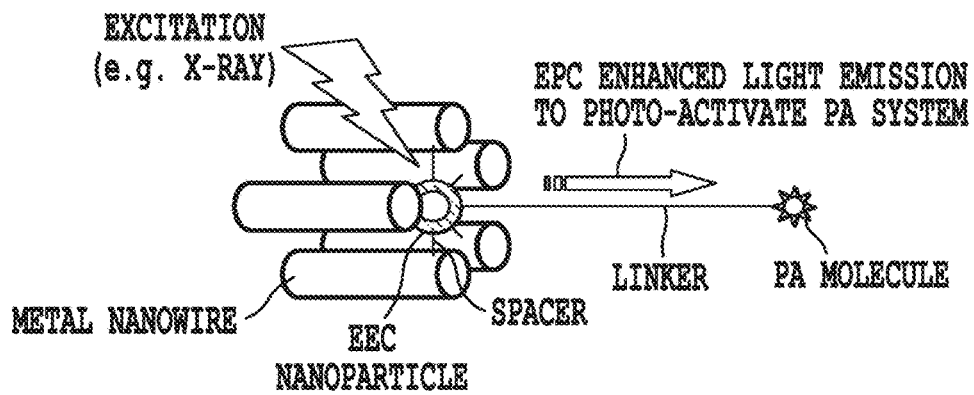
FIG. 33 is a graphical representation of an embodiment of EPEP probes having NPs and multiple NWs.

FIG. 33 shows another embodiment of EPEP probes of the present invention comprising superstructures of NPs linked to multiple NWs.

For some embodiments, by adding metal nanostructures designed to interact specifically with the excitons in the energy modulation agent system, there are significant improvements:

(1) an additional radiative pathway from exciton to photon conversion is introduced (2) the metal nanostructures can be designed to amplify (due to the plasmonics effect) the excitation radiation (e.g., X-ray) and/or the emission radiation (e.g, UV or visible) to excite the photo-active (PA) molecule, thereby enhancing the PA effectiveness.

Various metallic nanostructures that can be used in EPEP probe embodiments of the present invention are the same as those illustrated in FIG. 9 for the PEPST probes.

Experimental Methods

Preparation of Nanoparticles (Ag, Au)

There many methods to prepare metal nanoparticles for EPEP or PEPST probes. Procedures for preparing gold and silver colloids include electroexplosion, electrodeposition, gas phase condensation, electrochemical methods, and solution-phase chemical methods. Although the methodologies for preparing homogeneous-sized spherical colloidal gold populations 2-40 nm in diameter are well known [N. R. Jana, L. Gearheart and C. J. Murphy, *Seeding growth for size control of 5-40 nm diameter gold nanoparticles. Langmuir* 17 (2001), pp. 6782-6786], and particles of this size are commercially available. An effective chemical reduction method for preparing populations of silver particles (with homogeneous optical scattering properties) or gold particles (with improved control of size and shape monodispersity) is based on the use of small-diameter uniform-sized gold particles as nucleation centers for the further growth of silver or gold layers.

One approach involves citrate reduction of a gold salt to produce 12-20 nm size gold particles with a relatively narrow size distribution. One method for producing smaller gold particles was developed by Brust et al [Brust, M.; Walker, M; Bethell, D.; Schiffrin, D. J; Whyman, R. *Chem. Commun.* 1994, 801]. This method is based on borohydride reduction of gold salt in the presence of an alkanethiol capping agent to produce 1-3 nmparticles. Nanoparticle sizes can be controlled between 2 and 5 nm by varying the thiol concentration, [Hostetler, M. J.; Wingate, J. E.; Zhong, C. J.; Harris, J. E.; Vachet, R. W.; Clark, M R.; Londono, J. D.; Green, S. J.; Stokes, J. J; Wignall, G. D.; Glish, G. L.; Porter, M D.; Evans, N. D.; Murray, R. W. *Langmuir* 1998, 14, 17]. Phosphine-stabilized gold clusters have also been produced and subsequently converted to thiol-capped clusters by ligand exchange in order to improve their stability [Schmid, G.; Pfeil, R.; Boese, R.; Bandrmann, F.; Meyer, S.; Calis, G. H. M.; van der Velden, J. W. A. *Chem. Ber.* 1981, 114, 3634; Warner, M. G.; Reed, S. M.; Hutchison, J. E. *Chem. Mater.* 2000, 12, 3316.] and phosphine-stabilized monodispersed gold particles were prepared using a similar protocol to the Brust method [Weare, W. W.; Reed, S. M.; Warner, M G.; Hutchison, J. E. *J. Am. Chem. Soc.* 2000, 122, 12890]. See also recent review: Ziyi Zhong, Benoit[1] Male, Keith B.[1] Luong, John H. T., *More Recent Progress in the Preparation of Au Nanostructures, Properties, and Applications, Analytical Letters;* 2003, Vol. 36 Issue 15, p 3097-3118]

Fabrication of Nanoparticle of Metal coated with nanoshells of dyes

The Fabrication of Metal Nanoparticles Coated with Nanoshells of Dye molecules can be performed using the method described by Masuhara et al [AKITO MASUHARA_, SATOSHI OHHASHIy, HITOSHI KASAI; SHUJI OKADA, FABRICATION AND OPTICAL PROPERTIES OF NANOCOMPLEXES COMPOSED OF METAL NANOPARTICLES AND ORGANIC DYES, *Journal of Nonlinear Optical Physics & Materials* Vol. 13, Nos. 3 & 4 (2004) 587-592]. Nanocomplexes composed of Ag or Au as a core and 3-carboxlymethyl-5-[2-(3-octadecyl-2-benzoselenazolinylidene) ethylidene]rhodanine (MCSe) or copper (II) phthalocyanine (CuPc) as a shell are prepared by the co-reprepicitation method. In the case of Ag-MCSe nanocomplexes, 0.5 mM acetone solution of MCSe are injected into 10 ml of Ag nanoparticle water dispersion, prepared by the reduction of $AgNO_3$ using $NaBH_4$: Au-MCSe nanocomplexes are also fabricated in a similar manner. A water dispersion of Au nanoparticles was prepared by the reduction of $HAuCl_4$ using sodium citrate. Subsequently, 2 M $NH_4OH$ (50 µl) was added and the mixture was thermally treated at 50° C. This amine treatment often stimulates the J-aggregate formation of MCSe.6 Ag-CuPc and Au-CuPc nanocomplexes were also fabricated in the same manner: 1 mM 1-methyl-2-pyrrolidinone (NMP) solution of CuPc (200 µl) was injected into a water dispersion (10 ml) of Ag or Au nanoparticles.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photo activation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology*, Vol 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

In another aspect, the present invention further provides systems and kits for practicing the above described methods.

In one embodiment, a system in accordance with the present invention may include: (1) an initiation energy source; (2) one or more energy modulation agents; and (3) one or more activatable pharmaceutical agents.

In another embodiment, a system in accordance with the present invention may include an initiation energy source and one or more activatable pharmaceutical agents.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site. In other embodiments, endoscopic or laproscopic devices equipped with appropriate energy modulation agents (encapsulated from the biological medium) may be used to provide different wavelengths of UV or visible or infrared irradiation in a vicinity of or within a target structure.

In further embodiments, dose calculation and robotic manipulation devices may also be included in the system.

The reagents and chemicals useful for methods and systems of the present invention may be packaged in kits to facilitate application of the present invention. Such a kit for modifying a target structure would comprise at least one agent selected from the group consisting of energy modulation agents, plasmonics-active agents and combinations thereof. The energy modulation agents would be one or more light emitters capable of emitting at least two different wavelengths of light, each wavelength of light associated with a different biological response, and the different wavelengths capable of activating different biological responses. The kit would preferably include one or more containers suitable for storing the agents in stable forms.

In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, at least one plasmonics agent and containers suitable for storing the agents in stable form, and preferably further comprising instructions for administering the at least one activatable pharmaceutical agent, at least one plasmonics agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Having generally described this invention, a further understanding can be obtained by reference to certain specific examples which are provided herein for purposes of illustration only and are not intended to be limiting unless otherwise specified.

EXAMPLES

Preparation of Silver Nanoparticles

Silver (or gold) colloids were prepared according to the standard Lee-Meisel method: 200 mL of $10^{-3}$ M $AgNO_3$ aqueous solution was boiled under vigorous stirring, then 5 mL of 35-mM sodium citrate solution were added and the resulting mixture was kept boiling for 1 h. This procedure was reported to yield ~$10^{11}$ particles/mL of homogenously sized colloidal particles with a diameter of ~35-50 nm and an absorption maximum at 390 nm. The colloidal solutions were stored at 4° C. and protected from room light. Further dilutions of the colloidal solutions were carried out using distilled water.

Fabrication/Preparation of Metal Nanocaps

One approach has involved the use of nanospheres spin-coated on a solid support in order to produce and control the desired roughness. The nanostructured support is subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex nanospheres are commercially available in a wide variety of sizes. The shapes of these materials are very regular and their size can be selected for optimal enhancement. These materials comprise isolated dielectric nanospheres (30-nm diameter) coated with silver producing systems of half-nanoshells, referred to as nanocaps.

Figure 24:
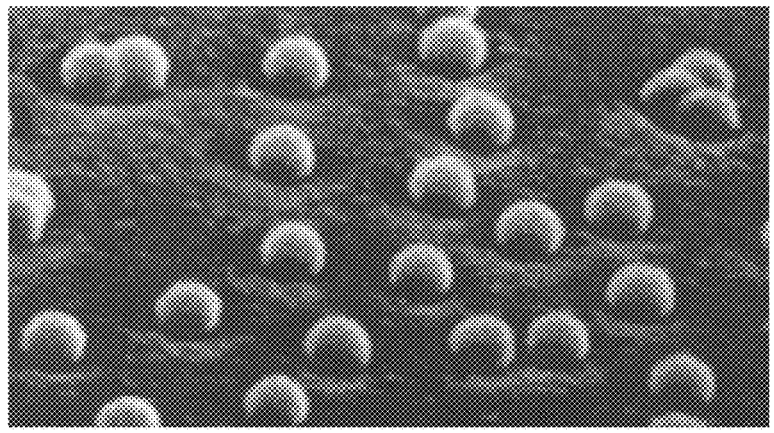
FIG. 24 is an photomicrograph showing nanocaps (half-nanoshells) comprising polystyrene nanospheres coated with silver.

FIG. 24 shows a scanning electron micrograph (SEM) of 300-nm diameter polymer nanospheres covered by a 100-nm thick silver nanocaps (half-nanoshell) coating. The nanoparticles can be sonicated to release them from the underlying substrate. The effect of the sphere size and metal layer thickness upon the SERS effect can be easily investigated. The silver coated nanospheres were found to be among the most plasmonics-active investigated. Gold can also be used instead of silver to coat over nanoparticles comprising PA drug molecules.

Fabrication of Gold Nanoshells

Gold nanoshells have been prepared using the method described by Hirsch et al. [Hirsch L R, Stafford R J, Bankson J A, Sershen S R, Price R E, Hazle J D, Halas N J, West J L (2003) Nanoshell-mediated near infrared thermal therapy of tumors under MR Guidance. Proc Natl Acad Sci 100: 13549-13554] using a mechanism involving nucleation and then successive growth of gold nanoparticles around a silica dielectric core. Gold nanoparticles, the seed, prepared as described above using the Frens method, were used to grow the gold shell. Silica nanoparticles (100 nm) used for the core of the nanoshells were monodispersed in solution of 1% APTES in EtOH. The gold "seed" colloid synthesized using the Frens method were grown onto the surface of silica nanoparticles via molecular linkage of amine groups. The "seed" covers the aminated silica nanoparticle surface, first as a discontinuous gold metal layer gradually growing forming a continuous gold shell. Gold nanoparticles used as the "seed" were characterized using optical transmission spectroscopy (UV-Vis Spectrophotometer, Beckman Coulter, Fullerton, Calif.) and atomic force microscopy (Atomic Force Microscope, Veeco Instruments, Woodbury, N.Y.) while gold nanoshells were characterized using optical transmission spectroscopy and scanning electron microscopy (Scanning Electron Microscope, Hitachi S-4700, Hitachi High Technologies America, Inc. Pleasanton, N.Y.).

Non-Medical Applications

Referring to FIG. 3-1, an exemplary system according to one embodiment of the invention may have an initiation energy source 1 directed at a generic medium 4 (biological or non-biological). Activatable agents 2 and an energy modulation agents 3 (such as the diamond and DLC-based energy modulation agents and/or the other energy modulation agents described above) are dispersed throughout the medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 3-1 as silica encased energy modulation agents. As shown in FIG. 3-1, initiation energy 7 in the form of radiation from the initiation energy source 1 permeated throughout the medium 4. A more thorough discussion of the computer system 5 is provided below in reference to FIGS. 4 and 5. The initiation energy source 1 can be an external energy source or an energy source located at least partially in the medium 4. Activatable agents 2 and/or the energy modulation agents 3 can include plasmonics agents which enhance either the applied energy or the energy emitted from the energy modulation agents 3 so as to directly or indirectly produce a change in the medium.

In various embodiments, the initiation energy source 1 may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.). In other embodiments, the initiation energy source 1 may be commercially available components of X-ray machines or non-medical X-ray machines. X-ray machines that produce from 10 to 150 keV X-rays are readily available in the marketplace. For instance, the General Electric Definium series or the Siemens MULTIX series are but two examples of typical X-ray machines designed for the medical industry, while the Eagle Pack series from Smith Detection is an example of a non-medical X-ray machine. As such, the invention is capable of performing its desired function when used in conjunction with commercial X-ray equipment.

In other embodiments, the initiation energy source 1 can be a radio frequency or microwave source emitting radio waves at a frequency which permeates the medium and which triggers or produces secondary radiant energy emission within the medium by interaction with the energy modulation elements 6 therein. In other embodiments, the initiation energy source 1 can be an ultraviolet, visible, near infrared (NIR) or infrared (IR) emitter emitting at a frequency which permeates the medium 4 and which triggers or produces secondary radiant energy emission within medium 4 by interaction with the energy modulation elements 6 therein.

The energy modulation structures of this invention can be provided on the interior of sealed quartz or glass tubes or can be provided coated on the surface of spheres or tubes, and further encapsulated with a silicate or another passivation layer. It is known that ultraviolet (UV) with a wavelength of 254 nm tends to inactivate most types of microorganisms. The deep UV diamond emission lines shown in FIGS. 34-1 and 34-2 make diamond (and DLC) a suitable choice for inclusion with the other energy modulation structures described herein or as a sole part of the energy modulation structures of this invention.

As on example of a non-medical application, most juices are opaque to UV due to the high-suspended solids in them and hence the conventional UV treatment, usually used for water treatment, cannot be used for treating juices. In order to make the process efficient, a thin film reactor constructed from glass has been used with the juice flowing along the inner surface of a vertical glass tube as a thin film. See "Ultraviolet Treatment of Orange Juice" by Tran et al. published in Innovative Food Science & Emerging Technologies (Volume 5, Issue 4, December 2004, Pages 495-502), the entire contents of which are incorporated herein by reference. Tran et al. reported that decimal reduction doses required for the reconstitute orange juices (OJ; 10.5° Brix) were 87±7 and 119±17 mJ/cm$^2$ for the standard aerobic plate count (APC) and yeast and moulds, respectively. They also reported that the shelf life of fresh squeezed orange juice was extended to 5 days with a limited exposure of UV (73.8 mJ/cm$^2$). The effect of UV on the concentration of Vitamin C was investigated using both HPLC and titration methods of measurements. The degradation of Vitamin C was 17% under high UV exposure of 100 mJ/cm$^2$, which was similar to that usually found in thermal sterilization. Enzyme pectin methylesterase (PME) activity, which is the major cause of cloud loss of juices, was also measured. The energy required for UV treatment of orange juice (2.0 kW h/m$^3$) was much smaller than that required in thermal treatment (82 kW h/m$^3$). The color and pH of the juice were not significantly influenced by the treatment.

The invention described herein offers advantages over this approach in that the energy modulation structures of this invention (including the diamond or DLC materials) can be placed inside fixtures such as quartz or glass (encapsulation structures) within the orange juice (or other fluid medium) and irradiated with x-ray or other high energy source supplied for example to the container to activate the encapsulated structures of the invention in the orange juice.

While discussed with regard to orange juice, any other medium to be sterilized including food products, medical products and cosmetic products could be treated using the technique of the invention described herein.

In one embodiment, the energy modulation structures of this invention (including the diamond or DLC materials) are complexed with other X-ray down converting particles or other energy modulation agents permitting for example X-ray irradiation to also assist in this process.

Sterilization of Blood Products

U.S. Pat. No. 6,087,141 (the entire contents of which are incorporated herein by reference) describes an ultraviolet light activated psoralen process for sterilization of blood transfusion products. The present invention can be applied for the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, anthroquinones, porphycene, rubyrin, rosarin, hexaphyrin, sapphyrin, chlorophyl, chlorin, phthalocynine, porphyrazine, bacteriochlorophyl, pheophytin, texaphyrin macrocyclic-based component, or a metalated derivative thereof. These photoactivatable agents serve as recipients for the secondarily generated light induced by the down conversion or upconversion.

In various embodiments of the invention, the UV or visible light recipients are secondary agents performing other functions. Suitable secondary agents for the invention include secondary emitters, cytotoxic agents, magnetic resonance imaging (MRI) agents, positron emission tomography (PET) agents, radiological imaging agents, or photodynamic therapy (PDT) agents.

These photoactivatable agents (recipients and secondary agents) are introduced into the blood product (or a patient's blood stream). An initiation energy such as x-ray (or other high energy source, deep UV, electrons, gamma rays) is applied to the blood product (dr to the patient). The energy modulation structures of this invention (including the diamond or DLC materials) invention (either included in the blood product or in encapsulated structures) generate secondary light such as UV or visible light which activates the photoactivatable agents in the blood products.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof.

Waste Water Detoxification

Photocatalysis has also been used as tertiary treatment for wastewater to comply with regulatory discharge limits and to oxidize compounds that have not been oxidized in the biological treatment. Photocatalysis has been used to reduce or eliminate several pollutants (e.g., alkanes, alkenes, phenols, aromatics, pesticides) with great success. In many cases, total mineralization of the organic compounds has been observed. Several photocatalysts, such as CdS, $Fe_2O_3$, ZnO, $WO_3$, and ZnS, have been studied, but the best results have been achieved with $TiO_2P_{25}$. These photocatalyst can be used in the invention.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

It is known that photocatalysis can be used for waste water reduction remediation. U.S. Pat. No. 5,118,422 (the entire contents of which are incorporated herein by reference) to Cooper et al. describe an ultraviolet driven photocatalytic post-treatment technique for purifying a water feedstock containing an oxidizable contaminant compound. In this work, the water feedstock was mixed with photocatalytic semiconductor particles (e.g., $TiO_2$, ZnO, CdS, CdSe, $SnO_2$, $SrTiO_3$, $WO_3$, $Fe_2O_3$, and $Ta_2O_5$ particles) having a particle size in the range of about 0.01 to about 1.0 micron and in an amount of between about 0.01% and about 0.2% by weight of the water. The water including the semiconductor mixture is exposed to band-gap photons for a time sufficient to affect an oxidation of the oxidizable contaminant to purify the water. Crossflow membrane filtration was used to separate the purified water from the semiconductor particles. Cooper et al. show that the organic impurity carbon content of simulated reclamation waters at nominal 40 PPM level were reduced to parts per billion using a recirculation batch reactor. Cooper et al. identified that one important aspect of the photocatalytic process is the adsorption of the organic molecules onto the extremely large surface area presented by the finely divided powders dispersed in the water. Cooper et al. further indicated that, in photoelectrochemical applications, advantage is taken of the fact that the solid phase (a metal oxide semiconductor) is also photo-active and that the generated charge carriers are directly involved in the organic oxidation. The adsorption of the band-gap photon by the semiconductor particle results in the formation of an electron ($e^-$)/hole ($h^+$) pair. Cooper et al. explain that the electrons generated in the conduction band react with solution oxygen forming the dioxygen anion ($O_2^-$) species which subsequently undergo further reactions resulting in the production of the powerfully oxidizing hydroxyl radical species, $^-OH$. These powerful oxidants are known to oxidize organic compounds by themselves. Additionally, Cooper et al. explain that the strongly oxidizing holes generated in the valence band have sufficient energy to oxidize all organic bonds.

In the reactor of Cooper et al., turbulence is necessary in order to ensure that the waste water contaminants and the photocatalytic titania particles are exposed to the UV light. Cooper et al. explain that the most basic considerations of photocatalyst light adsorption and its relationship to convective mixing. For a 0.1 wt % photocatalyst loading, experiments have shown that 90% of the light is absorbed within 0.08 cm. This is primarily due to the large UV absorption coefficient of the photocatalyst and therefore, most of the photoelectrochemistry occurs within this illuminated region. By operating the reactor of Cooper et al. with a Reynolds number (Re) of 4000, a significant portion of the photoactive region is ensured of being within the well mixed turbulent zone.

Santos et al. have reported in "Photocatalysis as a tertiary treatment for petroleum refinery wastewaters" published in Braz. J. Chem. Eng. vol. 23, No. 4, 2006 (the entire contents of which are incorporated herein by reference), photocatalysis for tertiary treatment for petroleum refinery wastewaters which satisfactorily reduced the amount of pollutants to the level of the regulatory discharge limits and oxidized persistent compounds that had not been oxidized in the biological treatment. The treatment sequence used by the refinery (REDUC/PETROBRAS, a Brazilian oil refinery) is oil/water separation followed by a biological treatment. Although the process efficiency in terms of biological oxygen demand (BOD) removal is high, a residual and persistent COD and a phenol content remains. The refining capacity of the refinery is 41,000 $m^3$/day, generating 1,100 $m^3$/h of wastewater, which are discharged directly into the Guanabara Bay (Rio de Janeiro). Treating the residual and persistent COD remains a priority.

Santos et al. conducted a first set of experiments carried out in an open 250 mL reactor containing 60 mL of wastewater. In the second set of experiments, a Pyrex® annular reactor containing 550 mL of wastewater was used (De Paoli and Rodrigues, 1978), as shown in FIG. 1. The reaction mixtures inside the reactors were maintained in suspension by magnetic stirring. In all experiments, air was continuously bubbled through the suspensions. A 250 W Phillips HPL-medium pressure mercury vapor lamp (with its outer bulb removed) was used as the UV-light source (radiant flux of 108 $J \cdot m^{-2} \cdot s^{-1}$ at $\lambda > 254$ nm). In one set of experiments, the lamp was positioned above the surface of the liquid at a fixed height (12 cm). In the second set, the lamp was inserted into the well. All experiments by Santos et al. were performed at 25±1° C. The catalyst concentration ranged from 0.5 to 5.5 g $L^{-1}$ and the initial pH ranged from 3.5 to 9.

In one embodiment of the invention described herein, the energy modulation structures of this invention (including the diamond or DLC materials) would be placed inside quartz or glass fixtures within the waste water or would be placed on silica encapsulated structures within the waste water which, like the photocatalytic $TiO_2$, could be entrained in the waste water during the irradiation.

Upon x-ray or other high energy radiation (or other high energy source, deep UV, electrons, gamma rays), the energy modulation structures of this invention (including the diamond or DLC materials) would generate UV light in nearby presence of the photocatalytic agent. In other words for this embodiment, the energy modulation structures of this invention (including the diamond or DLC materials) are mixed along with the photocatalytic semiconductor particles in the waste water fluid stream, and the exterior activation energy source penetrates the container (e.g., a plastic or aluminum container) and irradiates the bulk of the waste water, producing UV light throughout the waste water which in turn drives the photocatalytic reactions.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

Workers have found that UV irradiation could realize an effective graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photo-grafting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of the energy modulation structures of this invention (including the diamond or DLC materials) in dispersion in the fluid medium being used for photostimulation. Upon irradiation, these structures would generate UV light within the NIR penetration depth of the medium and permitting batch or bulk type processing to occur in parallel inside the container. Further, when laser light is used for the NIR, the plastic surface can be "written" onto such that inks would selectively absorb on those regions where surface of the polymer was exposed to the UV generated light.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Wanting to stop the fermentation process is all good in and of itself. But unfortunately, there is really no practical way to successfully stop a fermentation dead in its tracks. Additives such as sulphite and sorbate can be added to stabilize a fermented product and stop additional fermentation. Many winemakers will turn to sulfites such as that found in Sodium Bisulfite or Campden tablets for the answer. But, these two items are not capable of reliably killing enough of the yeast to guarantee a complete stop of the activity—at least not at normal doses that leave the wine still drinkable.

Once the bulk of the sulfites from either of these ingredients dissipate from the wine into the air—as sulfites do—there is a very strong chance that the remaining few live yeast cells will start multiplying and fermenting again if given enough time. This usually happens at a most inconvenient time, like after the wine has been bottled and stowed away.

Potassium sorbate is another ingredient that many winemakers consider when trying to stop a wine from fermenting any further. There is a lot of misunderstanding surrounding this product. It is typically called for by home wine making books when sweetening a wine. This is a situation where the fermentation has already completed and is ready for bottling. One adds the potassium sorbate along with the sugar that is added for sweetening.

The potassium sorbate stops the yeast from fermenting the newly added sugar. So, many winemakers assume potassium sorbate can stop an active fermentation as well, but, potassium sorbate does not kill the yeast at all, but rather it makes the yeast sterile. In other words, it impairs the yeast's ability to reproduce itself. But, it does not hinder the yeast's ability to ferment sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above could be used for the application described here. For non-liquid products, energy modulation agents with little and preferably no toxicity (e.g. Fe oxides or titanium oxides) could be added. Here, the concentration of these additives would likely be limited by any unexpected changes in taste.

In one embodiment, the energy modulation structures of this invention (including the diamond or DLC materials) are included in the yeast containing media, and with for example X-ray irradiation (or other high energy source, deep UV, electrons, gamma rays) stops the fermenting process.

Photoactivated Cross-Linking and Curing of Polymers

In this application, the energy modulation structures of this invention (including the diamond or DLC materials) are provided and distributed into an uncured polymer based medium for the activation of photosensitive agents in the medium to promote cross-linking and curing of the polymer based medium. In one embodiment, the diamond or DLC materials structures of the invention are complexed with other down-converting luminescent particles or other energy modulation agents prior to being added to the polymer.

For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the upconverter structures of the invention are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with, for example, carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silicone resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of the invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolamine-benzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4, 6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis (ηsup.5-2,4-cyclopentadien-1-yl)-bis[2,6-difluoro-3-(1H-pyrrol-1-yl)phenyl]titanium). Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm², a mean particle size of 70 microns, and a particle size range of 10-150 um. Other Q-CEL products are shown below in tabular form. Another commercially available hollow glass microsphere is sold by Kish under the trade name SPHERICEL. SPHEREICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCHLITE tradename. In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescing particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are the energy modulation structures of this invention (including the diamond or DLC materials). These compositions can then be applied to surfaces of objects to be fixed together or to surfaces where a hard coating is desired or cast in a curable form for the production of molded objects. These compositions upon activation will produce radiant light for photoactivated cure of the luminescing particle containing polymer composition. The density of the energy modulation structures (including the diamond or DLC materials) in these compositions will depend on the "light transparency" of the luminescing particle containing composition. Where these compositions contain a significant amount of the inorganic filler as discussed above, the concentration of the upconverter structures can be reduced for example as compared to a composition with a black color pigment where the light transparency will be significantly reduced.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the energy modulation structures of this invention (including the diamond or DLC materials) are added to these Bach et al. compositions. Due to the fact that the exterior energy source penetrates deeper into the entirety of the Bach et al. compositions, thicker surface coatings can be realized. Further, the coatings can be applied to intricate surfaces having for example been prepared with recesses or protrusions.

Moreover, in one embodiment of the invention, an external energy source of the initiation energy (x-rays or other high energy source, deep UV, electrons, gamma rays) can be directed to a structural element in which a gap (or crack) therein was filled with an uncured radiation-curable medium (such as those described above). The internally generated light will cure the uncured radiation-curable medium in the gap (or crack) thereby providing a repair to the structure being irradiated.

Presently, there is available commercial epoxy systems which utilize epoxy resin injection for the structural restoration of concrete. Epoxy injection is very often the only alternative to complete replacement of a structure. It therefore results in great cost savings. Besides filling the cracks, epoxy injection is known to protect rebar in the concrete and to stop water leakage. Commercially, the epoxy injection resin provides a system for welding cracks which restores the original strength and loading originally designed into the concrete. Typically, low viscosity resins are pressure injected into the cracks. Often holes are drilled near or into the cracks to provide a conduit for pumping the resin into the cracks.

It, however, takes time for the resin to penetrate into the thinner, even hair line cracks. Unfortunately, time is limited in the present commercial systems due to the fact that the resins are premixed with hardeners whose time to cure sets an upper limit for how long the low viscosity resin can flow into the cracks. Furthermore, time to complete repair is an issue in many industrial repairs as the hardener is usually present in a concentration high enough to have the resin set for example in twenty four (24) hours. Moreover, with traditional resin methods, it is not possible to induce curing at specific regions of interest since all the areas of the resin will be cured The present invention offers a number of advantages. Firstly, the resin of the present invention will be a photo-activated resin which will not substantially cure until the x-ray source generates internal light to activate the photoinitiators. This provides more flexibility in pumping and waiting for complete crack fill. Secondly, once the photoactivatable resin is in place, its cure is then activated, and the cure occurs at a rate not controlled by the convention hardening reaction. Thirdly, the x-ray penetration through the concrete and the crack region will provide a more uniform mechanism for cure of the resins, with the deep cracks being as likely to fully cure as the narrow cracks which may extend deeper into the material. Furthermore, the present invention allows the possibility to cure only the specific areas of interest, i.e., where the X-ray is irradiated.

In another embodiment of the present invention, the external energy source (x-rays or other high energy source, deep UV, electrons, gamma rays) can be a directed or focused beam of the initiation energy which cures an uncured radiation-curable medium to produce a patterned element. In this embodiment, the structure holding or at least partially enclosing the uncured radiation-curable medium can be a structure opaque to visible light. In this manner, the uncured radiation-curable medium (which normally would be photoactivated upon exposure to ambient light) can be transported without premature curing. In this embodiment, the curing would be activated for example by directed one or several focused beams of x-rays whose overlap generates regions in the structure holding or at least partially enclosing the uncured radiation-curable medium where the generated UV or visible light from the energy modulation agents in the medium would be of sufficient intensity to activate the photoinitiators. In this manner, precise three-dimensional and two-dimensional patterning can be performed.

As an example in another embodiment, a patterned element such as a device (such as plug to close a specific internal hole or path ways) can be fabricated (e.g., cured) inside structures (e.g., building materials, man-made or natural underground storage tank, internal organs of human body, etc) using energy excitation (e.g., X ray) from the outside of such structures. Another application of this technique would involve the fabrication of orthopedic structures inside the body, where the curable resin was introduced locally at the point of the orthopedic structure to be formed and a directed or focused x-ray beam cured the structure. In one embodiment, the procedure simultaneously or sequentially sterilizes the orthopedic structure (or other medical implant) in place. In one embodiment, the irradiation procedure can be repeated from time to time to re-sterilize the orthopedic structure (or other medical implant devices). In one embodiment, the diamond and diamond like converters as used to generate deep UV for sterilization, while other of the above-described energy modulation generate UV or visible light designed for polymerization.

Accordingly, in another embodiment of the present invention, there is provided a method (and associated system) for producing a patterned element inside a structure. The method places inside the structure a radiation curable medium including at least one of a plasmonics agent and an energy modulation agent such as the diamond or DLC based energy modulation agent. The energy modulation agent is configured to emit light into the medium upon interaction with an initiation energy. The method applies to the medium the initiation energy from a directed or focused energy source. The applied initiation energy interacts with the plasmonics agent or the energy modulation agent to generate light at local regions inside the structure to cure locally the radiation curable medium.

As noted above, this method can form for the patterned element a plug to close a hole or pathway in the structure such as for example holes or pathways in a building material, a man-made or natural underground storage tank, or an internal organ in a human or animal body. The method can form for the patterned element a prosthetic device at a local point in the body of a human or animal.

Additional modifications and variations of the present invention are possible in light of the above teachings. It is therefore to be understood that within the scope of the appended claims, the invention may be practiced otherwise than as specifically described herein.

The invention claimed is:

1. A method for effecting a predetermined change in biological activity to a target structure, comprising:
   providing within close proximity to or within the target structure one or more light emitters, each capable of emitting at least two different wavelengths of light, each wavelength of light associated with a different biological response, wherein the one or more light emitters comprise at least one energy modulation agent which adsorbs, intensifies or modifies an applied initiation energy into an energy that effects the predetermined change in said target structure;

applying the initiation energy from at least one source to the target structure, activating plural biological responses in the target structure depending on the different wavelengths of light provided internally within the target structure by the one or more light emitters, wherein the different wavelengths activate different biological responses simultaneously.

2. The method of claim 1, wherein activating plural biological responses comprises activating a first biological response with a first wavelength of light and a second biological response with a second wavelength of light.

3. The method of claim 2, wherein activating the first biological response comprises activating psoralen.

4. The method of claim 3, wherein activating the second biological response comprises generating a reactive oxygen species.

5. The method of claim 2, wherein activating the first biological response comprises at least one of photoactivating a drug, sterilizing the target structure, photoactivating psoralen, generating a reactive oxygen species, inducing an autoimmune response, exciting a DNA strand of a cancer cell, redirecting a metabolic pathway, up-regulating genes, down-regulating genes, secreting cytokines, altering cytokine receptor responses, releasing metabolites, or combinations thereof.

6. The method of claim 2, wherein activating the second biological response comprises at least one of photoactivating a drug, sterilizing the target structure, photoactivating psoralen, generating a reactive oxygen species, inducing an autoimmune response, exciting a DNA strand of a cancer cell, redirecting a metabolic pathway, up-regulating genes, down-regulating genes, secreting cytokines, altering cytokine receptor responses, releasing metabolites, or combinations thereof.

7. The method of claim 2, wherein activating the first biological response comprises bonding a pharmaceutical agent to a cellular structure.

8. The method of claim 7, wherein the bonding comprises bonding the pharmaceutical agent to at least one of nuclear DNA, mRNA, rRNA, ribosome, or mitochondrial DNA.

9. The method of claim 2, wherein at least one of said activating the first biological response and said activating the second biological response comprises altering a cellular response or a metabolic rate of the target structure.

10. The method of claim 2, wherein activating the first biological response comprises emitting ultraviolet light to act as a germicide, and wherein activating the second biological response comprises emitting near infrared light to act as an anti-inflammatory.

11. The method of claim 2, wherein activating the first biological response comprises emitting ultraviolet light to act as a germicide, and wherein activating the second biological response comprises emitting near infrared light to promote cellular proliferation.

12. The method of claim 2, wherein activating the first biological response comprises emitting ultraviolet light to act as a germicide, and wherein activating the second biological response comprises emitting near infrared light to reduce pain.

13. The method of claim 2, wherein activating the first biological response comprises photoactivating a pharmaceutical agent, and wherein activating the second biological response comprises heating a local area of the target structure.

14. The method of claim 1, wherein the predetermined change modifies the target structure or modulates the biological activity of the target structure.

15. The method of claim 1, further comprising contacting the target structure with at least one activatable pharmaceutical agent (PA) that is capable of effecting said predetermined change in the target structure when activated by one or more of the different wavelengths of light provided internally within the target structure.

16. The method of claim 1, wherein said at least one energy modulation agent comprises at least one of a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

17. The method of claim 1, wherein said at least one energy modulation agent decreases a wavelength of the initiation energy.

18. The method of claim 17, wherein said at least one energy modulation agent comprises inorganic materials selected from the group consisting of: metal oxides; metal sulfides; doped metal oxides; and mixed metal chalcogenides.

19. The method of claim 17, wherein said at least one energy modulation agent comprises at least one member selected from the group consisting of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS, and alkali lead silicate compositions which contain one or more of $SiO_2$, $B_2O_3$, $Na_2O$, $K_2O$, PbO, MgO, or Ag.

20. The method of claim 17, wherein said at least one energy modulation agent comprises at least one of ZnSeS: Cu, Ag, Ce, Tb; CaS: Ce, Sm; $La_2O_2S$:Tb; $Y_2O_2S$:Tb; $Gd_2O_2S$:Pr, Ce, F; $LaPO_4$.

21. The method of claim 17, wherein said at least one energy modulation agent comprises at least one of ZnS:Ag, ZnS:Cu, Pb, and alloys of the ZnSeS.

22. The method of claim 17, wherein said at least one energy modulation agent comprises at least one of sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3Tb$), gadolinium oxysulphide:europium ($Gd_2O_2S$:Eu), lanthanum oxysulphide:europium ($La_2O_2S$: Eu), and gadolinium oxysulphide:promethium, cerium, fluorine ($Gd_2O_2S$:Pr,Ce,F), $YPO_4$:Nd, $LaPO_4$:Pr, $(Ca,Mg)SO_4$: Pb, $YBO_3$:Pr, $Y_2SiO_5$:Pr, $Y_2Si_2O_7$:Pr, $SrLi_2SiO_4$:Pr,Na, and $CaLi_2SiO_4$:Pr.

23. The method of claim 17, wherein said at least one energy modulation agent comprises at least one of $KSrPO_4$: $Eu^{2+}$, $Pr^{3+}$, $NaGdF_4$:Eu, $Zn_2SiO_4$:$Tb^{3+}$, $Yb^{3+}$, β-$NaGdF_4$ co-doped with $Ce^{3+}$ and $Tb^{3+}$ ions, and $Gd_2O_2S$:Tm or $BaYF_5$:$Eu^{3+}$.

24. The method of claim 1, wherein said at least one energy modulation agent increases a wavelength of the initiation energy.

25. The method of claim 24, wherein said at least one energy modulation agent at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

26. The method of claim 1, wherein said predetermined change results in destruction, lysis or inactivation of the target structure.

27. The method of claim 1, wherein said predetermined change does not result in destruction or inactivation of the target structure.

28. The method of claim 1, wherein said predetermined change enhances an activity of the target structure.

29. The method of claim 1, wherein the target structure is a eukaryotic cell.

30. The method of claim 1, wherein the target structure is a prokaryotic cell.

31. The method of claim 1, wherein the target structure is a subcellular structure.

32. The method of claim 31, wherein the subcellular structure is a cell membrane, a nuclear membrane, cell nucleus, nucleic acid, mitochondria, ribosome, or other cellular organelle or component.

33. The method of claim 1, wherein the target structure is an extracellular structure.

34. The method of claim 1, wherein the target structure is a virus or prion.

35. The method of claim 1, wherein the target structure is a cellular tissue.

36. The method of claim 1, wherein the predetermined change results in treatment of a condition, disorder or disease in said subject.

37. The method of claim 36, wherein said condition, disorder or disease is cancer.

38. The method of claim 36, wherein said condition, disorder or disease occurs in a soft tissue and/or cartilage.

39. The method of claim 36, wherein said condition, disorder or disease occurs in bone tissue.

40. The method of claim 36, wherein said condition, disorder or disease is chronic pain.

41. The method of claim 36, wherein said condition, disorder or disease is at least one autoimmune disease.

42. The method of claim 36, wherein said predetermined change comprises wound healing.

43. The method of claim 36, wherein said predetermined change comprises enhancement of tissue growth, nerve regeneration or sensory regeneration/restoration.

44. The method of claim 36, wherein said condition, disorder or disease is a prion, viral, bacterial, fungal, or parasitic infection.

45. The method of claim 36, wherein said predetermined change comprises reduction or removal of fat deposits.

46. The method of claim 36, wherein said condition, disorder, or disease is characterized by varicose veins.

47. The method of claim 36, wherein said condition, disorder, or disease is characterized by an enlarged prostate.

48. The method of claim 36, wherein said condition, disorder, or disease is characterized by retinal injuries and other ocular diseases.

49. The method of claim 36, wherein said condition, disorder, or disease is Parkinson's disease.

50. The method of claim 36, wherein said condition, disorder, or disease is characterized by a behavioral, perceptional and/or cognitive disorder.

51. The method of claim 1, wherein said predetermined change comprises stimulation or modulation of brain cell activity with light.

52. The method of claim 1, wherein said predetermined change comprises modulation of cell death.

53. The method of claim 1, wherein said predetermined change comprises modulating cell growth and division.

54. The method of claim 1, wherein said predetermined change comprises modulation of an activity, quantity, or number of intracellular components in a cell.

55. The method of claim 1, wherein said predetermined change comprises modulation of an activity, quantity, or number of extracellular components produced by, excreted by, or associated with a cell.

56. The method of claim 1, wherein the initiation energy is UV radiation, visible light, IR radiation, x-rays, gamma rays, an electron beam, microwaves or radio waves.

57. The method of claim 1, wherein the different wavelengths of the light provided internally within the subject are generated in-situ in the subject.

58. The method of claim 57, wherein the different wavelengths of the light provided internally within the subject are generated from a distal end of a catheter inserted into the subject.

59. The method of claim 57, wherein the different wavelengths of the light provided internally within the subject are generated from energy modulation agents disposed at the distal end of the catheter.

60. The method of claim 57, wherein the different wavelengths of the light provided internally within the subject are generated from down converting materials disposed at the distal end of the catheter.

61. The method of claim 57, wherein the different wavelengths of the light provided internally within the subject are generated from up converting materials disposed at the distal end of the catheter.

62. The method of claim 1, wherein a plasmonics-active agent is further applied which enhances or modifies the initiation energy, such that enhanced initiation energy causes the predetermined change in said target structure by the plasmonics-active agent with or without an energy modulation agent.

63. The method of claim 1, wherein a plasmonics-active agent is further applied which enhances or modifies the initiation energy, such that enhanced initiation energy is absorbed, intensified or modified by an energy modulation agent into the energy that affects the predetermined change in said target structure.

64. The method of claim 1, providing at least one plasmonics-active agent within close proximity to or within the target structure.

65. The method of claim 64, wherein the plasmonics-active comprises plasmonics-active metal nanostructures.

66. The method of claim 65, wherein the metal nanostructures are nanospheres, nanorods, nanocubes, nanopyramids, nanoshells, multi-layer nanoshells and combinations thereof.

67. The method of claim 1, wherein said predetermined change modifies the target structure and modulates biological activity of the target structure thus treating a condition, disorder or disease affecting the target structure.

68. The method of claim 67, wherein said condition, disorder, or disease is mediated by abnormal cellular proliferation and said predetermined change ameliorates the abnormal cellular proliferation.

69. The method of claim 68, wherein said abnormal cellular proliferation is higher than that of cells from a subject not having said condition, disorder or disease.

70. The method of claim 68, wherein said abnormal cellular proliferation is lower than that of cells from a subject not having said condition, disorder or disease.

71. The method of claim 67, wherein said condition, disorder, or disease is not significantly mediated by abnormal cellular proliferation and said predetermined change does not substantially affect cellular proliferation.

72. The method of claim 67, wherein the initiation energy is x-rays, gamma rays, an electron beam, UV radiation, visible light, or infrared radiation.

73. The method of claim 67, wherein the initiation energy has the capability of penetrating completely through the subject.

74. The method of claim 67, wherein the condition, disorder, or disease is a cell proliferation disorder that is at least one member selected from the group consisting of cancer, bacterial infection, viral infection, parasitic infection, prion infection, fungal infection, immune rejection response, autoimmune disorders, aplastic conditions, and combinations thereof.

75. The method of claim 67, wherein said condition, disorder, or disease is selected from the group consisting of cardiac ablasion, photoangioplastic conditions, intimal hyperplasia, arteriovenous fistula, macular degeneration, psoriasis, acne, hopecia areata, portwine spots, hair removal, autoimmune diseases, rheumatoid and inflammatory arthritis, behavioral and cognitive disorders/conditions, joint conditions, Parkinson's disease, retinal injuries and other ocular diseases, enlarged prostate, varicose veins, reduction or removal of fat deposits, nerve regeneration, sensory regeneration/restoration, wound healing, chronic pain, conditions occurring in bone tissue, conditions occurring in a soft tissue and/or cartilage, and lymph node conditions.

76. The method of claim 67, wherein activating comprises activating a pharmaceutical agent which is photoactivatable.

77. The method of claim 76, wherein the pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

78. The method of claim 76, wherein the pharmaceutical agent is a psoralen, a coumarin, a porphyrin or a derivative thereof.

79. The method of claim 76, wherein the pharmaceutical agent is 8-MOP or AMT.

80. The method of claim 76, wherein the pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

81. The method of claim 76, wherein the pharmaceutical agent is coupled to a carrier that is capable of binding to a receptor site on or near the target structure.

82. The method of claim 81, wherein the carrier is one selected from insulin, interleukin, thymopoietin or transferrin.

83. The method of claim 81, wherein the pharmaceutical agent is coupled to the carrier by a covalent bond.

84. The method of claim 81, wherein the pharmaceutical agent is coupled to the carrier by non-covalent bond.

85. The method of claim 81, wherein the receptor site is one selected from nucleic acids of nucleated cells, antigenic sites on nucleated cells, or epitopes.

86. The method of claim 76, wherein the pharmaceutical agent has an affinity for the target structure.

87. The method of claim 76, wherein the target structure is a target cell and the at least one activatable pharmaceutical agent is capable of being preferentially absorbed by the target cell.

88. The method of claim 76, wherein the target structure is a target cell and the predetermined change is apoptosis in the target cell.

89. The method of claim 76, wherein the pharmaceutical agent, upon activation, causes an auto-vaccine effect in the subject that reacts with the target structure.

90. The method of claim 76, wherein the pharmaceutical agent is a DNA intercalator or a halogenated derivative thereof.

91. The method of claim 76, wherein the pharmaceutical agent comprises a light-sensitive protein that upon exposure to said initiation energy source modulates a signaling event in the brain.

92. The method of claim 76, wherein said predetermined change enhances the expression of, promotes the growth of, or increases the quantity of said target structure.

93. The method of claim 76, wherein said predetermined change enhances, inhibits or stabilizes the usual biological activity of said target structure compared to a similar untreated target structure.

94. The method of claim 76, wherein said predetermined change alters the immunological or chemical properties of said target structure.

95. The method of claim 94, wherein said target structure is a compound that is modified by said predetermined change to be more or less antigenic or immunogenic.

96. The method of claim 1, wherein the one or more light emitters comprise at least one of a diamond light emitter or a diamond-like carbon light emitter.

97. The method of claim 1, wherein the one or more light emitters comprise one or more coated energy modulation agents.

98. The method of claim 1, wherein the one or more coated energy modulation agents have a biocompatible coating.

99. The method of claim 1, wherein the biocompatible coating comprises at least one of poly(esters) based on polylactide (PLA), polyglycolide (PGA), polycarpolactone (PCL), poly(hydroxyalkanoate)s of the PHB-PHV class, poly(ester)s, natural polymers, modified poly(saccharide)s, starch, cellulose, chitosan, polyethylene oxides, poly(ether) (ester) block copolymers, and ethylene vinyl acetate copolymers.

100. The method of claim 1, wherein the biocompatible coating comprises at least one of a silica, a silicate, nanodiamond film, a diamond like carbon coating, or a graphene material.

101. A method for effecting a predetermined change in biological activity to a target structure, comprising:
providing within close proximity to or within the target structure one or more diamond or diamond-like carbon light emitters capable, upon exposure to an applied initiation energy, of emitting one or more wavelengths of light corresponding to respective one or more biological responses;

applying the initiation energy from at least one source to the target structure, thereby activating the one or more biological responses in the target structure depending on the emitted one or more wavelengths of light provided internally within the target structure from the one or more diamond or diamond-like carbon light emitters.

102. The method of claim 101, wherein the initiation energy contacts the target structure, activates the one or more biological responses, and induces the predetermined change in the target structure.

103. The method of claim 101, wherein the activating biological responses comprises at least one of 1) activating a first biological response with a first wavelength of light and 2) activating a second biological response with a second wavelength of light.

104. The method of claim 103, wherein activating the first biological response comprises activating psoralen.

105. The method of claim 104, wherein activating the second biological response comprises generating a reactive oxygen species.

106. The method of claim 103, wherein activating the first biological response comprises at least one of photoactivating a drug, sterilizing the target structure, photoactivating psoralen, generating a reactive oxygen species, inducing an autoimmune response, exciting a DNA strand of a cancer cell, redirecting a metabolic pathway, up-regulating genes, down-regulating genes, secreting cytokines, altering cytokine receptor responses, releasing metabolites, or combinations thereof.

107. The method of claim 103, wherein activating the second biological response comprises at least one of photoactivating a drug, sterilizing the target structure, photoactivating psoralen, generating a reactive oxygen species, inducing an autoimmune response, exciting a DNA strand of a cancer cell, redirecting a metabolic pathway, up-regulating genes, down-regulating genes, secreting cytokines, altering cytokine receptor responses, releasing metabolites, or combinations thereof.

108. The method of claim 103, wherein activating the first biological response comprises bonding a pharmaceutical agent to a cellular structure.

109. The method of claim 108, wherein the bonding comprises bonding the pharmaceutical agent to at least one of nuclear DNA, mRNA, rRNA, ribosome, or mitochondrial DNA.

110. The method of claim 103, wherein at least one of said activating the first biological response and said activating a second biological response comprises altering a cellular response or a metabolic rate of the target structure.

111. The method of claim 103, wherein activating the first biological response comprises emitting ultraviolet light to act as a germicide, and wherein activating the second biological response comprises emitting near infrared light to act as an anti-inflammatory.

112. The method of claim 103, wherein activating the first biological response comprises emitting ultraviolet light to act as a germicide, and wherein activating the second biological response comprises emitting near infrared light to promote cellular proliferation.

113. The method of claim 103, wherein activating the first biological response comprises emitting ultraviolet light to act as a germicide, and wherein activating the second biological response comprises emitting near infrared light to reduce pain.

114. The method of claim 103, wherein activating the first biological response comprises photoactivating a pharmaceutical agent, and wherein activating the second biological response comprises heating a local area of the target structure.

115. The method of claim 101, wherein the predetermined change modifies the target structure or modulates the biological activity of the target structure.

116. The method of claim 101, further comprising
contacting the target structure with at least one activatable pharmaceutical agent (PA) that is capable of effecting said predetermined change in the target structure when activated the different wavelengths of light provided internally within the target structure.

117. The method of claim 101, wherein said initiation energy generates light that induces the predetermined change in the target structure with or without an energy modulator or a photoactive agent.

118. The method of claim 101, further comprising administering to said subject at least one energy modulation agent which adsorbs, intensifies or modifies said initiation energy into an energy that in conjunction with light from the one or more diamond or diamond-like carbon light emitters effects the predetermined change in said target structure.

119. The method of claim 118, wherein said at least one energy modulation agent comprises at least one of a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

120. The method of claim 118, wherein said at least one energy modulation agent decreases a wavelength of the initiation energy.

121. The method of claim 120, wherein said at least one energy modulation agent comprises inorganic materials selected from the group consisting of: metal oxides; metal sulfides; doped metal oxides; and mixed metal chalcogenides.

122. The method of claim 120, wherein said at least one energy modulation agent comprises at least one member selected from the group consisting of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS, and alkali lead silicate compositions which contain one or more of $SiO_2$, $B_2O_3$, $Na_2O$, $K_2O$, PbO, MgO, or Ag.

123. The method of claim 120, wherein said at least one energy modulation agent comprises at least one of ZnSeS: Cu, Ag, Ce, Tb; CaS: Ce,Sm; $La_2O_2S$:Tb; $Y_2O_2S$:Tb; $Gd_2O_2S$:Pr, Ce, F; $LaPO_4$.

124. The method of claim 120, wherein said at least one energy modulation agent comprises at least one of ZnS:Ag, ZnS:Cu, Pb, and alloys of the ZnSeS.

125. The method of claim 120, wherein said at least one energy modulation agent comprises at least one of sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride (BaYF$_5$, BaY$_2$F$_8$), gadolinium oxysulfide (Gd$_2$O$_2$S), calcium tungstate (CaWO$_4$), yttrium oxide:terbium (Yt$_2$O$_3$Tb), gadolinium oxysulphide:europium (Gd$_2$O$_2$S:Eu), lanthanum oxysulphide:europium (La$_2$O$_2$S:Eu), and gadolinium oxysulphide:promethium, cerium, fluorine (Gd$_2$O$_2$S:Pr,Ce,F), YPO$_4$:Nd, LaPO$_4$:Pr, (Ca,Mg)SO$_4$:Pb, YBO$_3$:Pr, Y$_2$SiO$_5$:Pr, Y$_2$Si$_2$O$_7$:Pr, SrLi$_2$SiO$_4$:Pr,Na, and CaLi$_2$SiO$_4$:Pr.

126. The method of claim 120, wherein said at least one energy modulation agent comprises at least one of KSrPO$_4$: Eu$^{2+}$, Pr$^{3+}$, NaGdF$_4$:Eu, Zn$_2$SiO$_4$:Tb$^{3+}$, Yb$^{3+}$, β-NaGdF$_4$ co-doped with Ce$^{3+}$ and Tb$^{3+}$ ions, and Gd$_2$O$_2$S:Tm or BaYF$_5$:Eu$^{3+}$.

127. The method of claim 118, wherein said at least one energy modulation agent increases a wavelength of the initiation energy.

128. The method of claim 127, wherein said at least one energy modulation agent at least one of Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$ or alloys or layers thereof.

129. The method of claim 101, wherein said predetermined change results in destruction, lysis or inactivation of the target structure.

130. The method of claim 101, wherein said predetermined change does not result in destruction or inactivation of the target structure.

131. The method of claim 101, wherein said predetermined change enhances an activity of the target structure.

132. The method of claim 101, wherein the target structure is a eukaryotic cell.

133. The method of claim 101, wherein the target structure is a prokaryotic cell.

134. The method of claim 101, wherein the target structure is a subcellular structure.

135. The method of claim 134, wherein the subcellular structure is a cell membrane, a nuclear membrane, cell nucleus, nucleic acid, mitochondria, ribosome, or other cellular organelle or component.

136. The method of claim 101, wherein the target structure is an extracellular structure.

137. The method of claim 101, wherein the target structure is a virus or prion.

138. The method of claim 101, wherein the target structure is a cellular tissue.

139. The method of claim 101, wherein the predetermined change results in treatment of a condition, disorder or disease in said subject.

140. The method of claim 139, wherein said condition, disorder or disease is cancer.

141. The method of claim 139, wherein said condition, disorder or disease occurs in a soft tissue and/or cartilage.

142. The method of claim 139, wherein said condition, disorder or disease occurs in bone tissue.

143. The method of claim 139, wherein said condition, disorder or disease is chronic pain.

144. The method of claim 139, wherein said condition, disorder or disease is at least one autoimmune disease.

145. The method of claim 139, wherein said predetermined change comprises wound healing.

146. The method of claim 139, wherein said predetermined change comprises enhancement of tissue growth, nerve regeneration or sensory regeneration/restoration.

147. The method of claim 139, wherein said condition, disorder or disease is a prion, viral, bacterial, fungal, or parasitic infection.

148. The method of claim 139, wherein said predetermined change comprises reduction or removal of fat deposits.

149. The method of claim 139, wherein said condition, disorder, or disease is characterized by varicose veins.

150. The method of claim 139, wherein said condition, disorder, or disease is characterized by an enlarged prostate.

151. The method of claim 139, wherein said condition, disorder, or disease is characterized by retinal injuries and other ocular diseases.

152. The method of claim 139, wherein said condition, disorder, or disease is Parkinson's disease.

153. The method of claim 139, wherein said condition, disorder, or disease is characterized by a behavioral, perceptional and/or cognitive disorder.

154. The method of claim 101, wherein said predetermined change comprises stimulation or modulation of brain cell activity with light.

155. The method of claim 101, wherein said predetermined change comprises modulation of cell death.

156. The method of claim 101, wherein said predetermined change comprises modulating cell growth and division.

157. The method of claim 101, wherein said predetermined change comprises modulation of an activity, quantity, or number of intracellular components in a cell.

158. The method of claim 101, wherein said predetermined change comprises modulation of an activity, quantity, or number of extracellular components produced by, excreted by, or associated with a cell.

159. The method of claim 118, wherein said one or more diamond or diamond-like carbon light emitters are provided as a coating on at least a portion of a surface of the energy modulation agent.

160. The method of claim 159, wherein said one or more diamond or diamond-like carbon light emitters form a coating on all of the surface of the energy modulation agent.

161. The method of claim 101, wherein said one or more diamond or diamond-like carbon light emitters comprise a plurality of defects in the diamond or diamond-like carbon light emitter such that upon excitation, a plurality of wavelengths of light are emitted.

162. The method of claim 161, wherein said one or more diamond or diamond-like carbon light emitters is a single diamond or diamond-like carbon light emitter having the plurality of defects present.

163. The method of claim 161, wherein said one or more diamond or diamond-like carbon light emitters are a plurality of types of diamond or diamond-like carbon light emitters each of the plurality of types has a different defect than the others of the plurality of types.

* * * * *